United States Patent
Abarzúa et al.

(10) Patent No.: US 8,043,834 B2
(45) Date of Patent: Oct. 25, 2011

(54) UNIVERSAL REAGENTS FOR ROLLING CIRCLE AMPLIFICATION AND METHODS OF USE

(75) Inventors: Patricio Abarzúa, West Caldwell, NJ (US); Natalia Smelkova, Hamden, CT (US); Jason Sparkowski, West Hartford, CT (US)

(73) Assignee: Qiagen GmbH, Hilden (DE)

( * ) Notice: Subject to any disclaimer, the term of this patent is extended or adjusted under 35 U.S.C. 154(b) by 478 days.

(21) Appl. No.: 10/405,822

(22) Filed: Mar. 31, 2003

(65) Prior Publication Data

US 2004/0191784 A1     Sep. 30, 2004

(51) Int. Cl.
    C12P 19/34     (2006.01)
(52) U.S. Cl. .................... 435/91.2; 435/91.21
(58) Field of Classification Search .......... 435/6
    See application file for complete search history.

(56) References Cited

U.S. PATENT DOCUMENTS

| | | |
|---|---|---|
| 2,264,423 A | 8/1939 | Wingenroth |
| 3,654,090 A | 4/1972 | Wilhelmus et al. |
| 3,687,808 A | 8/1972 | Merigan et al. |
| 3,921,105 A | 11/1975 | Brgetz |
| 3,983,421 A | 9/1976 | Yogore |
| 3,995,018 A | 11/1976 | Sjoquist |
| 4,299,916 A | 11/1981 | Litman et al. |
| 4,469,863 A | 9/1984 | Ts'o |
| 4,476,301 A | 10/1984 | Imbach et al. |
| 4,748,111 A | 5/1988 | Dattagupat et al. |
| 4,816,567 A | 3/1989 | Cabilly et al. |
| 4,837,003 A | 6/1989 | Nicolotti |
| 4,845,205 A | 7/1989 | Huynh Dinh et al. |
| 4,883,750 A | 11/1989 | Whiteley et al. |
| 4,937,183 A | 6/1990 | Ultee et al. |
| 4,940,670 A | 7/1990 | Rhodes |
| 4,965,188 A | 10/1990 | Mullis et al. |
| 4,981,957 A | 1/1991 | Lebleu et al. |
| 4,984,957 A | 1/1991 | Noguchi et al. |
| 4,994,373 A | 2/1991 | Stavrianopoulos et al. |
| 4,994,557 A | 2/1991 | Kassis et al. |
| 5,001,050 A | 3/1991 | Blanco et al. |
| 5,023,243 A | 6/1991 | Tullis |
| 5,034,506 A | 7/1991 | Summerton et al. |
| 5,043,272 A | 8/1991 | Hartley |
| 5,106,727 A | 4/1992 | Hartley et al. |
| 5,118,800 A | 6/1992 | Smith et al. |
| 5,130,238 A | 7/1992 | Malek et al. |
| 5,130,302 A | 7/1992 | Spielvogel et al. |
| 5,134,066 A | 7/1992 | Rogers et al. |
| 5,137,806 A | 8/1992 | LeMaistre et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,187,060 A | 2/1993 | Cerutti et al. |
| 5,188,897 A | 2/1993 | Suhadolnik et al. |
| 5,198,543 A | 3/1993 | Blanco et al. |
| 5,214,134 A | 5/1993 | Weis et al. |
| 5,216,141 A | 6/1993 | Benner |
| 5,235,033 A | 8/1993 | Summerton et al. |
| 5,242,794 A | 9/1993 | Normal et al. |
| 5,262,311 A | 11/1993 | Pardee et al. |
| 5,264,423 A | 11/1993 | Cohen et al. |
| 5,264,562 A | 11/1993 | Matteuci |
| 5,264,564 A | 11/1993 | Matteuci |
| 5,264,567 A | 11/1993 | Numata et al. |
| 5,268,486 A | 12/1993 | Waggoner et al. |
| 5,273,638 A | 12/1993 | Konard et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,328,824 A | 7/1994 | Ward et al. |
| 5,334,711 A | 8/1994 | Sproat et al. |
| 5,354,668 A | 10/1994 | Auerbach |
| 5,359,044 A | 10/1994 | Cook et al. |
| 5,367,066 A | 11/1994 | Urdea et al. |
| 5,367,069 A | 11/1994 | Beck et al. |

(Continued)

FOREIGN PATENT DOCUMENTS

AU        84173/91        2/1992

(Continued)

OTHER PUBLICATIONS

Ausubel et al. *Current Protocols in Molecular Biology*, John Wiley & Sons, 1:1.6.1-1.6.6 (1988).
Barbato et al. Solid Phase Syntheses of Cyclic Oligodeoxyribonucleotides. *Tetrahedron Letters*. 28(46):5727-2728 (1987).
Bryant et al. Phosphorothioate substrates for T4 RNA ligase. *Biochemistry*. 21(23):5877-5885 (1982).
Capobianco et al. One pot solution synthesis of cyclic oligodeoxyribonudeotides. *Nucleic Acids Research*, 18(9):2661-2669 (1990).
Cheung et al. Whole genome amplification using a degenerate oligonucleotide primer allows hundreds of genotypes to be performed on less than one nanogram of genomic DNA. *Proc Natl Acad Sci USA*. 93:14676-14679 (1996).

(Continued)

*Primary Examiner* — Gary Benzion
*Assistant Examiner* — Cynthia B Wilder
(74) *Attorney, Agent, or Firm* — Ballard Spahr LLP

(57) ABSTRACT

Disclosed are compositions and methods useful for labeling and detection of analytes. The compositions generally are associations of three components: reporter binding agents, amplification target circles, and DNA polymerase. The compositions are assembled prior to their use in a rolling circle amplification reaction and can be stored and transported prior to use without substantial loss of activity. The reporter binding agents generally are composed of a specific binding molecule and a rolling circle replication primer. The specific binding molecule can be specific for a target molecule. The rolling circle replication primer has sequence complementary to the amplification target circle. The DNA polymerase can interact with the rolling circle replication primer and amplification target circle. For use as a general reagent, the specific binding molecule is not bound to the target molecule until the composition is used in an assay.

66 Claims, 1 Drawing Sheet

U.S. PATENT DOCUMENTS

| | | | |
|---|---|---|---|
| 5,393,878 A | 2/1995 | Leumann | |
| 5,399,676 A | 3/1995 | Froehler | |
| 5,405,938 A | 4/1995 | Summerton et al. | |
| 5,405,939 A | 4/1995 | Suhadolnik | |
| 5,409,818 A | 4/1995 | Davey et al. | |
| 5,412,087 A | 5/1995 | McGall et al. | |
| 5,427,930 A | 6/1995 | Birkenmeyer et al. | |
| 5,429,807 A | 7/1995 | Matson et al. | |
| 5,432,272 A | 7/1995 | Benner | |
| 5,434,257 A | 7/1995 | Matteuci et al. | |
| 5,443,986 A | 8/1995 | Haughland | |
| 5,445,934 A | 8/1995 | Fodor et al. | |
| 5,446,137 A | 8/1995 | Maag et al. | |
| 5,451,067 A | 9/1995 | Pieper | |
| 5,451,203 A | 9/1995 | Lamb | |
| 5,453,496 A | 9/1995 | Caruthers et al. | |
| 5,455,166 A | 10/1995 | Walker | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,427 A | 12/1995 | Fujima | |
| 5,476,786 A | 12/1995 | Huston | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,500,341 A | 3/1996 | Spears | |
| 5,502,177 A | 3/1996 | Matteucci et al. | |
| 5,510,270 A | 4/1996 | Fodor et al. | |
| 5,514,785 A | 5/1996 | Van Ness et al. | |
| 5,516,134 A | 5/1996 | Crawford et al. | |
| 5,516,663 A | 5/1996 | Backman et al. | |
| 5,516,664 A | 5/1996 | Hyman | |
| 5,519,126 A | 5/1996 | Hecht | |
| 5,519,134 A | 5/1996 | Acevedo et al. | |
| 5,521,065 A | 5/1996 | Whiteley et al. | |
| 5,523,204 A | 6/1996 | Singer et al. | |
| 5,525,711 A | 6/1996 | Hawkins et al. | |
| 5,536,821 A | 7/1996 | Agrawal et al. | |
| 5,538,871 A | 7/1996 | Nuovo et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,547,843 A | 8/1996 | Studier et al. | |
| 5,550,111 A | 8/1996 | Suhadolnik et al. | |
| 5,552,540 A | 9/1996 | Haralambidis | |
| 5,556,748 A | 9/1996 | Douglas | |
| 5,556,771 A | 9/1996 | Shen et al. | |
| 5,556,772 A | 9/1996 | Sorge et al. | |
| 5,561,045 A | 10/1996 | Dorval et al. | |
| 5,561,225 A | 10/1996 | Maddry et al. | |
| 5,563,037 A | 10/1996 | Sutherland et al. | |
| 5,563,253 A | 10/1996 | Agrawal et al. | |
| 5,563,912 A | 10/1996 | Yasunaga et al. | |
| 5,565,339 A * | 10/1996 | Bloch et al. | 435/91.2 |
| 5,567,811 A | 10/1996 | Misiura et al. | |
| 5,571,799 A | 11/1996 | Tkachul et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,609 A | 1/1997 | Auerbach | |
| 5,591,722 A | 1/1997 | Montgomery et al. | |
| 5,593,836 A | 1/1997 | Niemiec et al. | |
| 5,594,121 A | 1/1997 | Froehler et al. | |
| 5,596,086 A | 1/1997 | Matteucci et al. | |
| 5,596,091 A | 1/1997 | Switzer et al. | |
| 5,597,909 A | 1/1997 | Urdea et al. | |
| 5,599,695 A | 2/1997 | Pease et al. | |
| 5,599,921 A | 2/1997 | Sorge et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,389 A | 3/1997 | Auerbach | |
| 5,614,390 A | 3/1997 | McCaslin et al. | |
| 5,614,617 A | 3/1997 | Cook et al. | |
| 5,618,704 A | 4/1997 | Sanghui et al. | |
| 5,623,070 A | 4/1997 | Cook et al. | |
| 5,625,050 A | 4/1997 | Beaton et al. | |
| 5,627,053 A | 5/1997 | Usman et al. | |
| 5,629,158 A | 5/1997 | Uhlen | |
| 5,629,179 A | 5/1997 | Mierendoft et al. | |
| 5,633,360 A | 5/1997 | Bischofberger et al. | |
| 5,635,602 A | 6/1997 | Cantor et al. | |
| 5,639,599 A | 6/1997 | Ryder et al. | |
| 5,639,873 A | 6/1997 | Barascut et al. | |
| 5,646,265 A | 7/1997 | McGee | |
| 5,648,213 A | 7/1997 | Reddy et al. | |
| 5,648,245 A | 7/1997 | Fire et al. | |
| 5,654,413 A | 8/1997 | Brenner | |
| 5,658,873 A | 8/1997 | Bentsch-Frank et al. | |
| 5,663,312 A | 9/1997 | Chaturvedula | |
| 5,665,539 A | 9/1997 | Sano et al. | |
| 5,670,633 A | 9/1997 | Cook et al. | |
| 5,677,437 A | 10/1997 | Wies et al. | |
| 5,677,439 A | 10/1997 | Weis et al. | |
| 5,679,509 A | 10/1997 | Wheeler et al. | |
| 5,681,941 A | 10/1997 | Cook et al. | |
| 5,683,985 A | 11/1997 | Chu et al. | |
| 5,691,136 A | 11/1997 | Lupski et al. | |
| 5,695,933 A | 12/1997 | Schalling et al. | |
| 5,700,920 A | 12/1997 | Altmann et al. | |
| 5,710,028 A | 1/1998 | Eyal et al. | |
| 5,712,100 A | 1/1998 | Nakahama et al. | |
| 5,714,320 A | 2/1998 | Kool | |
| 5,714,331 A | 2/1998 | Buchardt et al. | |
| 5,719,262 A | 2/1998 | Buchardt et al. | |
| 5,728,526 A | 3/1998 | George et al. | |
| 5,733,733 A | 3/1998 | Auerbach | |
| 5,736,365 A | 4/1998 | Walker et al. | |
| 5,744,305 A | 4/1998 | Fodor et al. | |
| 5,766,891 A | 6/1998 | Shuman | |
| 5,770,408 A | 6/1998 | Sato | |
| 5,795,714 A | 8/1998 | Cantor et al. | |
| 5,800,992 A | 9/1998 | Fodor et al. | |
| 5,800,994 A | 9/1998 | Martinelli et al. | |
| 5,807,674 A | 9/1998 | Tyagi | |
| 5,817,529 A | 10/1998 | Wu | |
| 5,821,084 A | 10/1998 | Olmsted et al. | |
| 5,824,517 A | 10/1998 | Cleuziat et al. | |
| 5,830,711 A | 11/1998 | Barany et al. | |
| 5,849,544 A | 12/1998 | Harris et al. | |
| 5,854,033 A * | 12/1998 | Lizardi | 435/91.2 |
| 5,856,096 A | 1/1999 | Windle et al. | |
| 5,866,329 A | 2/1999 | Demetriou et al. | |
| 5,866,336 A | 2/1999 | Nazarenko et al. | 435/6 |
| 5,871,697 A | 2/1999 | Rothberg et al. | |
| 5,871,914 A | 2/1999 | Nathan | |
| 5,871,921 A | 2/1999 | Landgren et al. | |
| 5,871,928 A | 2/1999 | Fodor et al. | |
| 5,874,260 A | 2/1999 | Cleuziat et al. | |
| 5,876,924 A | 3/1999 | Zhang et al. | 435/5 |
| 5,876,932 A | 3/1999 | Fischer | |
| 5,876,992 A | 3/1999 | De Rosier et al. | |
| 5,880,473 A | 3/1999 | Ginestet | |
| 5,882,912 A | 3/1999 | Sandstrom et al. | |
| 5,882,935 A | 3/1999 | Hirai et al. | |
| 5,888,731 A | 3/1999 | Yager et al. | |
| 5,891,636 A | 4/1999 | Van Gelder et al. | |
| 5,909,132 A | 6/1999 | Trofimenkoff et al. | |
| 5,912,124 A | 6/1999 | Kumar | |
| 5,912,148 A | 6/1999 | Eggerding | |
| 5,914,229 A | 6/1999 | Loewy | |
| 5,925,517 A | 7/1999 | Tyagi et al. | |
| 5,942,391 A | 8/1999 | Zhang et al. | 435/6 |
| 5,942,609 A | 8/1999 | Hunkapiller et al. | |
| 5,945,312 A | 8/1999 | Goodman et al. | |
| 5,955,933 A | 9/1999 | Nishihara et al. | |
| 5,959,095 A | 9/1999 | Martinelli et al. | |
| 5,962,223 A | 10/1999 | Whiteley et al. | |
| 5,968,743 A | 10/1999 | Matsunaga et al. | |
| 5,976,806 A | 11/1999 | Mahajan et al. | |
| 5,985,639 A | 11/1999 | Christianson et al. | |
| 5,998,175 A | 12/1999 | Akhavan-Tafti | |
| 6,007,994 A | 12/1999 | Ward et al. | |

| | | |
|---|---|---|
| 6,008,373 A | 12/1999 | Waggoner et al. |
| 6,013,431 A | 1/2000 | Soderlund et al. |
| 6,013,444 A | 1/2000 | Dau et al. |
| 6,017,703 A | 1/2000 | Kinders et al. |
| 6,020,138 A | 2/2000 | Akhavan-Tafti |
| 6,025,139 A | 2/2000 | Yager et al. |
| 6,027,889 A | 2/2000 | Barany et al. |
| 6,027,923 A | 2/2000 | Wallace |
| 6,033,881 A | 3/2000 | Himmler et al. |
| 6,037,130 A | 3/2000 | Tyagi et al. |
| 6,054,274 A | 4/2000 | Sampson et al. |
| 6,057,105 A | 5/2000 | Hoon et al. |
| 6,064,274 A | 5/2000 | Nayebi et al. |
| 6,077,668 A | 6/2000 | Kool |
| 6,077,674 A | 6/2000 | Schleifer et al. |
| 6,087,133 A | 7/2000 | Dattagupta et al. |
| 6,087,476 A | 7/2000 | Kenten et al. |
| 6,096,880 A | 8/2000 | Kool ............................ 536/25.3 |
| 6,117,635 A | 9/2000 | Nazarenko et al. ................ 435/6 |
| 6,124,120 A | 9/2000 | Lizardi |
| 6,132,728 A | 10/2000 | Beachy et al. |
| 6,140,055 A | 10/2000 | Todd et al. |
| 6,143,495 A | 11/2000 | Lizardi et al. |
| 6,169,816 B1 | 1/2001 | Ravkin |
| 6,183,960 B1 | 2/2001 | Lizardi |
| 6,197,533 B1 | 3/2001 | Dawkes et al. |
| 6,203,984 B1 | 3/2001 | Hu et al. |
| 6,210,884 B1 | 4/2001 | Lizardi |
| 6,214,587 B1 | 4/2001 | Dattagupta et al. |
| 6,221,603 B1 | 4/2001 | Mahtani ............................ 435/6 |
| 6,225,636 B1 | 5/2001 | Ginestet |
| 6,235,502 B1 | 5/2001 | Weissman et al. |
| 6,242,188 B1 | 6/2001 | Dattagupta et al. |
| 6,248,535 B1 | 6/2001 | Dandenberg et al. |
| 6,255,082 B1 | 7/2001 | Lizardi et al. |
| 6,255,636 B1 | 7/2001 | Cochran, II et al. |
| 6,259,807 B1 | 7/2001 | Ravkin |
| 6,274,320 B1 | 8/2001 | Rothberg et al. |
| 6,277,607 B1 | 8/2001 | Tyagi et al. |
| 6,280,949 B1 | 8/2001 | Lizardi |
| 6,287,765 B1 | 9/2001 | Cubicciotti |
| 6,287,768 B1 | 9/2001 | Chenchik et al. |
| 6,287,776 B1 | 9/2001 | Hefti |
| 6,287,824 B1 | 9/2001 | Lizardi |
| 6,288,220 B1 | 9/2001 | Kambara et al. |
| 6,291,183 B1 | 9/2001 | Pirrung et al. |
| 6,291,187 B1 | 9/2001 | Kingsmore et al. ............... 435/6 |
| 6,291,193 B1 | 9/2001 | Khodadoust |
| 6,291,669 B1 | 9/2001 | Kwiatkowski et al. |
| 6,294,664 B1 | 9/2001 | Ravikumar et al. |
| 6,297,006 B1 | 10/2001 | Drmanac et al. |
| 6,300,073 B1 | 10/2001 | Zhao et al. |
| 6,312,902 B1 | 11/2001 | Shultz et al. |
| 6,316,229 B1 | 11/2001 | Lizardi et al. |
| 6,323,009 B1 | 11/2001 | Lasken et al. ................. 435/91.1 |
| 6,329,150 B1 | 12/2001 | Lizardi et al. |
| 6,344,329 B1 | 2/2002 | Lizardi |
| 6,355,431 B1 | 3/2002 | Chee et al. |
| 6,361,940 B1 | 3/2002 | Van Ness et al. |
| 6,365,729 B1 | 4/2002 | Tyagi et al. |
| 6,368,801 B1 | 4/2002 | Faruqi |
| 6,403,319 B1 | 6/2002 | Lizardi et al. |
| 6,417,340 B1 | 7/2002 | Mirkin et al. |
| 6,440,707 B1 | 8/2002 | Kwoh et al. |
| 6,458,544 B1 | 10/2002 | Miller |
| 6,458,556 B1 | 10/2002 | Hayashizaki |
| 6,472,185 B2 | 10/2002 | McCasky Feazel et al. |
| 6,475,736 B1 | 11/2002 | Stanton |
| 6,479,235 B1 | 11/2002 | Schumm et al. |
| 6,479,242 B1 | 11/2002 | Guo et al. |
| 6,479,244 B1 | 11/2002 | Belouchi et al. |
| 6,498,023 B1 | 12/2002 | Abarzua |
| 6,506,563 B1 | 1/2003 | Ward et al. |
| 6,531,283 B1 | 3/2003 | Kingsmore et al. |
| 6,573,051 B2 | 6/2003 | Alsmadi et al. |
| 6,617,137 B2 | 9/2003 | Dean et al. |
| 6,632,609 B2 | 10/2003 | Lizardi |
| 6,635,425 B2 | 10/2003 | Bandaru et al. |
| 6,642,034 B2 | 11/2003 | Lizardi |
| 6,670,126 B2 | 12/2003 | Kingsmore et al. |
| 6,686,157 B2 | 2/2004 | Ward et al. |
| 6,703,228 B1 | 3/2004 | Landers et al. |
| 6,703,885 B1 | 3/2004 | Fan et al. |
| 6,706,519 B1 | 3/2004 | Kellogg et al. |
| 6,713,257 B2 | 3/2004 | Shoemaker et al. |
| 6,777,183 B2 | 8/2004 | Abarzua |
| 6,797,474 B2 | 9/2004 | Lizardi |
| 6,811,986 B2 | 11/2004 | Bandaru et al. |
| 6,830,884 B1 | 12/2004 | Hafner et al. |
| 6,861,222 B2 | 3/2005 | Ward et al. |
| 6,861,231 B2 | 3/2005 | Shao |
| 6,921,642 B2 | 7/2005 | Kingsmore et al. |
| 6,977,148 B2 | 12/2005 | Dean et al. |
| 6,977,153 B2 | 12/2005 | Kumar et al. |
| RE39,007 E | 3/2006 | Dattagupta et al. |
| 7,041,480 B2 | 5/2006 | Abarzua |
| 7,074,600 B2 | 7/2006 | Dean et al. |
| 7,297,485 B2 | 11/2007 | Bornarth et al. |
| 7,358,047 B2 | 4/2008 | Hafner et al. |
| 7,553,619 B2 | 6/2009 | Kumar et al. |
| 7,618,776 B2 | 11/2009 | Lizardi |
| 2001/0041340 A1 | 11/2001 | Kingsmore et al. |
| 2002/0009716 A1 | 1/2002 | Abarzua |
| 2002/0119465 A1* | 8/2002 | Zhao et al. .................... 435/6 |
| 2002/0120409 A1 | 8/2002 | Cao et al. |
| 2002/0192649 A1 | 12/2002 | Lizardi |
| 2002/0192658 A1 | 12/2002 | Ward et al. |
| 2002/0197694 A1 | 12/2002 | Shao |
| 2003/0008313 A1 | 1/2003 | Wiltshire |
| 2003/0022167 A1 | 1/2003 | Alsmadi et al. |
| 2003/0032024 A1 | 2/2003 | Lizardi |
| 2003/0059786 A1 | 3/2003 | Ward et al. |
| 2003/0092901 A1 | 5/2003 | Farooqui et al. |
| 2003/0108902 A1 | 6/2003 | Abarzua |
| 2003/0121338 A1 | 7/2003 | Yates |
| 2003/0143613 A1 | 7/2003 | Kingsmore et al. |
| 2003/0152932 A1 | 8/2003 | Kumar et al. |
| 2003/0165948 A1* | 9/2003 | Alsmadi et al. .................. 435/6 |
| 2003/0175788 A1 | 9/2003 | Alsmadi et al. |
| 2003/0207267 A1 | 11/2003 | Lasken et al. |
| 2003/0207323 A1 | 11/2003 | Bandaru et al. |
| 2003/0235849 A1 | 12/2003 | Lizardi |
| 2004/0063144 A1 | 4/2004 | Lizardi |
| 2004/0091857 A1 | 5/2004 | Nallur et al. |
| 2004/0121338 A1 | 6/2004 | Alsmadi et al. |
| 2004/0126770 A1 | 7/2004 | Kumar et al. |
| 2004/0191784 A1 | 9/2004 | Abarzua et al. |
| 2004/0248103 A1 | 12/2004 | Feaver et al. |
| 2004/0248105 A1 | 12/2004 | Kumar |
| 2004/0265897 A1 | 12/2004 | Lizardi |
| 2005/0079523 A1 | 4/2005 | Hafner et al. |
| 2006/0083683 A1 | 4/2006 | Hsei et al. |
| 2006/0126764 A1 | 6/2006 | Eklund et al. |
| 2006/0166227 A1 | 7/2006 | Kingsmore et al. |
| 2006/0188892 A1 | 8/2006 | Kumar et al. |
| 2008/0096258 A1 | 4/2008 | Korfhage et al. |

FOREIGN PATENT DOCUMENTS

| | | |
|---|---|---|
| AU | 84173/91 A | 2/1992 |
| AU | 649066 | 5/1994 |
| AU | 5850996 A | 11/1996 |
| AU | 714486 | 4/2000 |
| AU | 749560 B2 | 6/2002 |
| EP | 0 070 685 | 7/1982 |
| EP | 0 128 332 | 12/1984 |
| EP | 0 310 030 A1 | 4/1989 |
| EP | 0 320 308 A2 | 6/1989 |
| EP | 0 356 021 | 2/1990 |
| EP | 0 379 369 | 7/1990 |
| EP | 0 395 398 A2 | 10/1990 |
| EP | 0 439 182 | 7/1991 |
| EP | 0 466 520 | 1/1992 |
| EP | 0 505 012 | 9/1992 |
| EP | 0 531 080 A2 | 3/1993 |
| EP | 0 640 691 A2 | 3/1995 |
| EP | 0 667 393 | 8/1995 |
| EP | 0 678 582 | 10/1995 |
| EP | 0 745 690 | 12/1996 |

| | | |
|---|---|---|
| EP | 0 756 009 A2 | 1/1997 |
| GB | 2332516 | 6/1999 |
| JP | 4262799 | 9/1992 |
| JP | 4304900 | 10/1992 |
| JP | 5146299 | 6/1993 |
| WO | WO-89/09824 | 10/1989 |
| WO | WO-90/11372 | 10/1990 |
| WO | WO-91/06643 | 5/1991 |
| WO | WO-91/08307 | 6/1991 |
| WO | WO 91/80307 | 6/1991 |
| WO | WO-91/16446 | 10/1991 |
| WO | WO 92/01813 | 2/1992 |
| WO | WO 94/16108 | 7/1994 |
| WO | WO 94/24312 | 10/1994 |
| WO | WO 95/03430 | 2/1995 |
| WO | WO 95/03432 | 2/1995 |
| WO | WO 95/25180 | 9/1995 |
| WO | WO 95/22623 | 11/1995 |
| WO | WO 95/35390 | 12/1995 |
| WO | WO-95/35390 | 12/1995 |
| WO | WO-96/00795 | 1/1996 |
| WO | WO-96/14406 | 5/1996 |
| WO | WO 96/33207 | 10/1996 |
| WO | WO-98/02449 | 1/1997 |
| WO | WO-97/07235 | 2/1997 |
| WO | WO-98/14610 | 4/1997 |
| WO | WO 97/17076 | 5/1997 |
| WO | WO 97/17471 | 5/1997 |
| WO | WO 97/19193 | 5/1997 |
| WO | WO 97/20948 | 6/1997 |
| WO | WO 97/42346 | 11/1997 |
| WO | WO 98/04746 | 2/1998 |
| WO | WO-98/16248 | 4/1998 |
| WO | WO-98/39485 | 9/1998 |
| WO | WO 99/18241 | 4/1999 |
| WO | WO 99/31276 | 6/1999 |
| WO | WO-99/54452 | 10/1999 |
| WO | WO 00/04193 | 1/2000 |
| WO | WO 00/15779 | 3/2000 |
| WO | WO 00/36141 | 6/2000 |
| WO | WO-00/70095 A2 | 11/2000 |
| WO | WO 00/71562 | 11/2000 |
| WO | WO-01/20039 A2 | 3/2001 |
| WO | WO-01/27326 A2 | 4/2001 |
| WO | WO-01/38580 A2 | 5/2001 |
| WO | WO 01/40516 | 6/2001 |
| WO | WO 01/61037 | 8/2001 |
| WO | WO 01/64952 | 9/2001 |
| WO | WO 01/77390 | 10/2001 |
| WO | WO 01/79420 | 10/2001 |
| WO | WO 01/88190 | 11/2001 |
| WO | WO 01/97616 | 12/2001 |
| WO | WO 02/00934 | 1/2002 |
| WO | WO 02/02792 | 1/2002 |
| WO | WO 02/053780 | 7/2002 |
| WO | WO 02/077256 | 10/2002 |
| WO | WO 02/103058 | 12/2002 |
| WO | WO 03/008538 | 1/2003 |
| WO | WO-03/033724 A2 | 4/2003 |
| WO | WO 03/066908 | 8/2003 |
| WO | WO-2004/009814 A1 | 1/2004 |
| WO | WO-2004/058987 A2 | 7/2004 |
| WO | WO 2004/061119 | 7/2004 |

OTHER PUBLICATIONS

Christian et al. Detection of DNA point mutations and mRNA expression levels by rolling circle amplification in individual cells. *Proc Natl Acad Sci USA.* 98(25):14238-14243. Epub Nov. 27, 2001 (Dec. 4, 2001).
Cummins et al. Biochemical and physicochemical properties of phosphorodithioate DNA. *Biochemistry.* 35(26):8734-8741 (1996).
de Vroom et al. Syntheses of cyclic oligonucleotides by a modified phosphotriester approach. *Nucleic Acids Research.* 16(10):4607-4620 (1988).
Diegelman et al. Generation of circular RNAs and trans-cleaving catalytic RNAs by rolling transcription of circular DNA oligonucleotides encoding hairpin ribozymes. *Nucleic Acids Res.* 26(13):3235-3241 (1998).
Doherty et al. Structural and mechanistic conservation in DNA ligases. Survey and Summary. *Nucleic Acids Res.* 28(21):4051-4058 (2000).
Dolinnaya et al. Oligonucleotide circularization by template-directed chemical ligation. *Nucleic Acids Res.* 21(23):5403-5407 (1993).
Eckstein et al. Phosphorothioates in molecular biology. *Trends in Bioch Sci.* 14:97-100 (1989).
Erie et al. Melting Behavior of a Covalently Closed, Single-Stranded, Circular DNA. *Biochemistry.* 28:268-273. (1989).
Faruqi et al. High-throughput genotyping of single nucleotide polymorphisms with rolling circle amplification. *BMC Genomics* 2(4) (2001).
Gait. Oligonucleotides. *Antisense Research and Applications.* (Crooke et al, eds., CRC Press) 16:289-301 (1993).
Gryaznov et al. Template controlled coupling and recombination of oligonucleotide blocks containing thiophosphoryl groups. *Nucleic Acids Res.* 21(6):1403-1408 (1993).
Haff et al. Single-nucleotide polymorphism identification assays using a thermostable DNA polymerase and delayed extraction MALDI-TOF mass spectrometry. *Genome Res.* 7(4):378-388 (1997).
Hermanson et al., eds. *Immobilized Affinity Ligands.* (Academic Press, NY, 1992).
Ishikawa et al. Sequence-based typing of HLA-A2 alleles using a primer with an extra base mismatch. *Hum Immunol.* 42(4):315-318 (1995).
James et al. Surprising fidelity of template-directed chemical ligation of oligonucleotides. *Chemistry & Biology.* 4:595-605 (1997).
Johnstone and Thorpe, *Immunochemistry In Practice*, Blackwell Scientific Publications, Oxford, England, pp. 30-85 (1987).
Johnstone et al. Immunochemistry in Practice. (Blackwell Scientific Publications, Oxford, England, 1987) pp. 209-216 and 241-242.
Kanaya et al. Template-Directed Polymerization of Oligoadenylates Using Cyanogen Bromide. *Biochemistry.* 25:7423-7430 (1986).
Kinoshita et al. Strand Ligation in a double-stranded DNA by T4 RNA Ligase. *Chemistry Letters.* 797-798 (1996).
Kricka. Ultrasensitive immunoassay techniques. *Clin Biochem.* 26(5):325-331 (1993).
Lizardi et al. Cascade rolling circle amplification, a homogeneous fluorescence detection system for DNA diagnostics. *Clinical Chemistry* 43(11):2219-2220 (1997).
Lyons et al. Immunosuppressant FK506 promotes neurite outgrowth in cultures of PC12 cells and sensory ganglia. *Proc Natl Acad Sci USA.* 91(8): 3191-3195 (1994).
Marshall et al. A biopolymer by any other name would bind as well: a comparison of the ligand-binding pockets of nucleic acids and proteins. *Structure.* 5(6):729-734. (1997).
Mendoza et al. High-Throughput Microarray-Based Enzyme-Linked Immunosorbent Assay (ELISA). *BioTechniques.* vol. 27(4):778-788 (1999).
Navarro et al. A general strategy for cloning viroids and other small circular RNAs that uses nminimal amounts of template and does not require prior knowledge of its sequence. *J Virol Meth.* 56:59-66 (1996).
Nilsson et al. Real-time monitoring of rolling-cirde amplification using a modified molecular beacon design. *Nucleic Acids Res.* 30(14):e66 (2002).
Prakash et al. Molecular Recognition by Circular Oligonucleotides. Strong Binding of Single-Stranded DNA and RNA. *J Chem Soc, Chem Commun.* 1161-1163 (1991).
*Protein immobilization: fundamentals and applications*, Richard F. Taylor, ed. (M. Dekker, New York, 1991).
Reese et al. The *H*-phosphonate approach to the solution phase synthesis of linear and cyclic oligoribonucleotides. *Nucleic Acids Research.* 7(4):963-971 (1999).
Rossi et al. Functional characterization of the T4DNA ligase: a new insight into the mechanism of action. *Nucleic Acids Res.* 25(11):2106-2113 (1997).
Rubin et al. Convergent DNA synthesis: a non-enzymatic diverization approach to circular oligodeoxynucleotides. *Nucleic Acids Res.* 23(17):3547-3553 (1995).
Saiki et al. Enzymatic Amplifications of β-Globin Genomic Sequences and Restriction Site Analysis for Diagnosis of Sickle Cell Anemia. *Science* 230:1350-1354 (1985).

Sambrook et al. *Molecular Cloning: A Laboratory Manual*. 2nd Edition (Cold Spring Harbor Laboratory Press, Cold Spring Harbor, N.Y., 1989) Chapters 5, 6).

Schena et al. DNA Microarrays: A Practical Approach. (Oxford University Press, New York, 1999) 1-16.

Schenk et al. The accessibility of thiophosphorylated groups in DNA fragments to the enzymatic activity of ligases and restriction endonuclease Bbs 1. *Biochem Mol Biol Int.* 36(5):1037-1043 (1995) Abstract.

Silzel et al. Mass-sensing, Multianalyte Microarray Immunoassay with Imaging Detection. *Clin. Chem.* 44: 2036-2043 (1998).

Skerra. Phosphorothioate primers improve the amplification of DNA sequences by DNA polymerases with proofreading activity. *Nucleic Acids Res.* 20(14):3551-3554 (1992).

Stratagene Catalog, p. 39 (1988).

Stratagene Catalog, p. 76 (1992).

Strong et al. Marked improvement of PAC and BAC cloning is achieved using electroelution of pulsed-field gel-separated partial digests of genomic DNA. *Nucleic Acids Res.* 25(19):3959-3961(1997).

Unrau et al. Non-cloning amplification of specific DNA fragments from whole genomic DNA digests using DNA 'indexers'. *Gene.* 145(2):163-169 (1994).

Welford et al. Detection of differentially expressed genes in primary tumor tissues using representational differences analysis coupled to microarray hybridization. *Nucleic Acids Res.* 26(12):3059-3065 (1998).

Wemmer et al. Preparation and melting of single strand circular DNA loops. *Nucleic Acids Res.* 13(23):8611-8621(1985).

White et al. Concatemer chain reaction: a Taq DNA polymerase-mediated mechanism for generating long tandemly repetitive DNA sequences. *Anal Biochem.* 199(2):184-190 (1991).

Wilson et al. Enzyme complex amplification—a signal amplification method for use in enzyme immunoassays. *Anal Biochem.* 209(1):183-187 (1993).

Xu et al. Nonenzymatic autoligation in direct three-color detection of RNA and DNA point mutations. *Nature Biotechnology.* 19:148-152 (2001).

Yang et al. Combining SSH and cDNA Micarrays for rapid identification of differentially expressed genes. *Nucleic Acids Res.* 27(6):1517-1523 (1999).

Zehavi et al. Light sensitive glycosides. II. 2-Nitrobenzyl 6-Deoxy-a-L-mannopyranoside and 2-Nitrobenzyl 6-Deoxy-β-L-galactopyranoside. *J. Organic Chem.* 37(14):2285-2285 (1972).

Zhang et al. Amplification of target-specific, ligation-dependent circular probe. *Gene* 211:277-285.

Ørum et al. Single base pair mutation analysis by PNA directed PCR clamping. *Nucl. Acids Res.* 21(23):5332-5336 (1993).

AAAI Board of Directors. Measurement of specific and nonspecific IgG$_4$ levels as diagnositc and prognostic tests for clinical allergy. *J. Allergy. Clin. Immunol.* 95(3):652-654 (1995).

Abravaya et al. Detection of point mutations with a modified ligase chain reaction (Gap-LCR). *Nucl. Acids Res.* 23(4):675-682 (1995).

Aliotta et al. Thermostable *Bst* DNA polymerase I lacks a 3'→5' proofreading exonuclease activity. *Gen. Anal.* 12:185-195 (1996).

Alves et al. Dot blot detection of point mutations with adjacently hybridising synthetic oligonucleotide probes. *Nucl. Acids Res.* 16(17):8723 (1988).

Anderson et al. A comparison of selected mRNA and protein abundances in human liver. *Electrophoresis* 18:533-537 (1997).

Arnold et al. Assay Formats Involving Acridinium-Ester-Labeled DNA Probes. *Clin. Chem.* 35(8):1588-1594 (1989).

Baner et al. Signal amplification of padlock probes by rolling circle replication. *Nucl. Acid Res.* 26(22):5073-5078 (1998).

Barany. Genetic disease detection and DNA amplification using cloned thermostable ligase. *Proc. Natl. Acad. Sci. USA* 88:189-193 (Jan. 1991).

Beaucage et al. Deoxynucleoside phosphoramidites—a new class of key intermediates for deoxypolynucleotide synthesis. *Tetrahedron Lett.* 22(20):1859-1862(1981).

Bertina et al. Mutation in blood coagulation factor V associated with resistance to activated protein C. *Nature* 369:64-67 (May 5, 1994).

Birkenmeyer et al. DNA probe amplification methods. *J. Virol. Meth.* 35:117-126 (1991).

Blanco et al. Characterization and purification of a phage ø29-encoded DNA polymerase required for the initiation of replication. *Proc. Natl. Acad. Sci. USA* 81:5325-5329 (Sep. 1984).

Blanco et al. Highly Efficient DNA Synthesis by the Phage ø29 DNA Polymerase. *J. Biol. Chem.* 264(15):8935-8940 (May 25, 1989).

Blanco et al. Terminal protein-primed DNA amplification. *Proc. NatL Acad. Sci. USA* 91:12198-12202 (Dec. 1994).

Boehmer et al. Herpes Simplex Virus Type 1 ICP8: Helix-Destabilizing Properties. *J. Virol* 67(2):711-715 (Feb. 1993).

Bonnet et al. Thermodynamic basis of the enhanced specificity of structured DNA probes. *Proc. Natl. Acad. Sci. USA* 96(11):6171-6176 (May 1999).

Broude et al. Enhanced DNA sequencing by hybridization. *Proc. Natl. Acad. Sci. USA* 91:3072-3076 (Apr. 1994).

Brush. Dye hard: protein gel staining products. *The Scientist.* 12:16-22 (May 11, 1998).

Burgess et al. A New Photolabile Protecting Group for Nucleotides. *Abstracts of Papers, Part 2.; 211th ACS National Meeting, American Chemical Society.* New Orleans, LA, Mar. 24-28, 1996.

Butler et al. Bacteriophage SP6-specific RNA polymerase. *J. Biol. Chem.* 257(10):5772-5778 (May 25, 1982).

Chang. The pharmacological basis of anti-IgE therapy. *Nat. Biotech.* 18:157-162 (Feb. 2000).

Chatterjee et al. Cloning and overexpression of the gene encoding bacteriophage T5 DNA polymerase. *Gene* 97:13-19 (1991).

Chetverina et al. Cloning of RNA molecules in vitro. *Nucl. Acids Res.* 21(10):2349-2353 (1993).

Colantuoni et al. Gene Expression Profiling in Postmortem Rett Syndrome Brain: Differential Gene Expression and Patient Classification. *Neutoboil. Dis.* 8:847-865 (2001).

Colantuoni et al. High Throughput Analysis of Gene Expression in the Human Brain. *J. Neurosci Res.* 59:1-10, 2000.

Craxton et al. Linear Amplification Sequencing, a Powerful Method for Sequencing DNA. *Meth. Compan. Meth. Enzymol.* 3(1):20-26 (Aug. 1991).

Crooke et al. Pharmacokinetic Properties of Several Novel Oligonucleotide Analogs in mice. *J. Pharmacol. Exp. Ther.* 277(2):923-937 (1996).

Daubendiek et al. Generation of catalytic RNAs by rolling transcription of synthetic DNA nanocircles. *Nat. Biotechnol.* 15(3):273-277 (Mar. 1997).

Daubendiek et al. Rolling-Circle RNA Synthesis: Circular Oligonucleotides an Efficient Substrates for T7 RNA Polymerase. *J. Am. Chem. Soc.* 117:7818-7819 (1995).

Davanloo et al. Cloning and expression of the gene for bacteriophage T7 RNA polymerase. *Proc. Natl. Acad. Sci. USA* 81:2035-2039 (Apr. 1984).

Dean et al. Rapid Amplification of Plasmid and Phage DNA Using Phi29 DNA Polymerase and Multiply-Primed Rolling Circle Amplification. *Genome Res.* 11:1095-1099 (2001).

DYNAL Technical Handbook. Biomagnetic techniques in molecular biology. (DYNAL A.S., 1995).

Ekins. Ligand assays: from electrophoresis to miniaturized microarrays. *Clin. Chem.* 44(9):2015-2030 (1998).

Englisch et al. Chemically modified oligonucleotides as probes and inhibitors. *Angewandte Chemie, Intl Ed.* 30(6):613-722 (Jun. 1991).

Ernst et al. Cyanine Dye Labeling Reagents for Sulfhydryl Groups. *Cytometry* 10:3-10 (1989).

Fields et al. How many genes in the human genome? *Nat. Genet.* 7:345-346 (Jul. 1994).

Fire et al. Rolling replication of short DNA circles. *Proc. Natl. Acad. Sci. USA* 92:4641-4645 (May 1995).

Fleischmann et al. Whole-Genome Random Sequencing and Assembly of *Haemophilus influenza* Rd. *Science* 269:496-512 (Jul. 28, 1995).

Gasparro et al. Site-specific targeting of psoralen photoadducts with a triple helix-forming oligonucleotide: characterization of psoralen monoadduct and crosslink formation. *Nucl. Acids Res.* 22(14):2845-2852 (1994).

Gerdes et al. Dynamic Changes in the Higher-Level Chromatin of Specific Sequences Revealed by In Situ Hybridization to Nuclear Halos. *J. Cell Biol.* 126(2):289-304 (Jul. 1994).

Guatelli et al. Isothermal, in vitro amplification of nucleic acids by a multienzyme reaction modeled after retroviral replication. *Proc. Natl. Acad. Sci. USA* 87:1874-1878 (Mar. 1990).

Gunji et al. Correlation between the serum level of hepatitis C virus RNA and disease activities in acute and chronic hepatitis C. *Int. J. Cancer* 52(5):726-730.

Guo et al. Direct fluorescence analysis of genetic polymorphisms by hybridization with oligonucleotide arrays on glass supports. *Nucl. Acids Res.* 22(24):5456-5464 (1994).

Guo et al. Enhanced discrimination of single nucleotide polymorphisms byartificial mismatch hybridization. *Nat. Biotechnol.* 15:331-335 (Apr. 1997).

Gupta et al. Expression of HIV-1 RNA in plasma correlates with the development of AIDS: a multicenter AIDS cohort study (MACS) *Ninth International Conference on.AIDS/Fourth STD World Congress.* Jun. 6-11, 1993, Berlin, Germany (abstract).

Gusev et al. Rolling Circle Amplification: A New Approach to Increase Sensitivity for Immunohistochemistry and Flow Cytometry. *Am.n J. Pathol.* 159(1):63-69 (Jul. 2001).

Gygi et al. Correlation between Protein and mRNA Abundance in Yeast. *Mol. Cell Biol.* 19(3):1720-1730 (Mar. 1999).

Hacia et al. Detection of heterozygous mutations in BRCA1 using high density oligonucleotide arrays and two-colour fluorescence analysis. *Nat. Genet.* 14:441-447 (Dec. 1996).

Hagiwara et al. Quantitation of Hepatitis C Virus RNA in Serum of Asymptomatic Blood Donors and Patients with Type C Chronic Liver Disease. *Hepatology* 17(4)545-550 (Apr. 1993).

Hall et al. Nucleotide. Part XLI. Mixed Anhydrides as Intermediates in the Synthesis of Dinucleoside Phosphates. *J. Chem. Soc.* 3291-3296 (1957).

Hall et al. From the Cover: Sensitive detection of DNA polymorphisms by the serial invasive signal amplification reaction. *Proc. Natl. Acad. Sci. USA* 97(15):8272-8277 (Jul. 2000).

Hanvey et al. Antisense and Antigene Properties of Peptide Nucleic Acids. *Science* 258:1481-1485 (Nov. 27, 1992).

Hata et al. Structure of the Human Ornithine Transcarbamylase Gene. *J. Biochem.* 103:302-308 (1988).

Heinonen et al. Simple triple-label detection of seven cystic fibrosis mutations by time-resolved fluorometry. *Clin. Chem.* 43(7):1142-1150 (1997).

Hendrickson et al. High sensitivity multianalyte immunoassay using covalent DNA-labeled antibodies and polymerase chain reaction. *Nucl. Acids Res.* 23(3):522-529 (1995).

Henegariu et al. Custom flourescent-nucleotide synthesis as an alternative method for nucleic acid labeling. *Nat. Biotech.* 18:345-346 (Mar. 2000).

Hoeltke et al. Multiple Nucleic Acid Labeling and Rainbow Detection. *Anal. Biochem.* 207:24-31 (1992).

Holland et al. Detection of specific polymerase chain reaction product by utilizing the 5'→3' exonuclease activity of *Thermus aquaticus* DNA polymerase. *Proc. Natl. Acad. Sci. USA* 88:7276-7280 (Aug. 1991).

Holloway et al. An exonuclease-amplification coupled capture technique improves detection of PCR product. *Nucl. Acids Res.* 21(16):3905-3906 (1993).

Hoy et al. Bromodeoxyuridine/DNA analysis of replication in CHO cells after exposure to UV light. *Mutat. Res.* 290:217-230 (1993).

Hsuih et al. Quantitative detection of HCV RNA using novel ligation-dependent polymerase chain reaction. *American Association for the Study of Liver Diseases.* (Chicago, IL, Nov. 3-7, 1995) [poster abstract].

Humphery-Smith and Blackstock. Proteome Analysis: Genomics via the Output Rather than the Input Code. *J. Protein Chem.* 16(5):537-544 (1997).

Itakura et al. Synthesis and Use of Synthetic Oligonucleotides. *Annu. Rev. Biochem.* 53:323-356 (1984).

Iyer et al. 3H-1,2-benzodithiole-3-one 1, 1-Dioxide as an Improved Sulfurizing Reagent in the Solid-Phase Syntesis of Oligodeoxyribonucleotide Phosphorotioates. *J. Am. Chem. Soc.* 112:1253-1254 (1990).

Jacobsen et al. The N-Terminal Amino-Acid Sequences of DNA Polymerase I from *Escherichia coli* and of the Large and the Small Fragments Obtained by a Limited Proteolysis. *Eur. J. Biochem.* 45:623-627 (1974).

Jiang et al. An efficient method for generation and subcloning of tandemly repeated DNA sequences with defined length, orientation and spacing. *Nucl. Acids Res.* 24(16):3278-3279 (1996).

Jónsson et al. Sequence of the DNA ligase-encoding gene from thermus scotoductus and conserved motifs in DNA ligases. *Gene* 151:177-180 (1995).

Jung et al. Bacteriophage PRDI DNA polymerase: Evolution of DNA polymerases. *Proc. Natl. Acad. Sci. USA* 84:8287-8291 (1987).

Kabanov et al. A new class of antivirals: antisense oligonucleotides combined with a hydrophobic substituent effectively inhibit influenze virus reproduction and synthesis of virus-specific proteins in MDCK cells. *FEBS Lett.* 259(2):327-330 (1990).

Kaboord et al. Accessory proteins function as matchmakers in the assembly of the T4 DNA polymerase holoenzyme. *Curr. Biol.* 5(2):149-157 (1995).

Kälin et al. Evaluation of the ligase chain reaction (LCR) for the detection of point mutations. *Mutat. Res.* 283(2):119-128 (1992).

Kaplan et al. Rapid Photolytic of Adenosine 5'-Triphosphate from a Protected Analogue: Utilization by the Na:K Pump of Human Red Blood Cell Ghosts. *Biochemistry* 17:1929-1935 (1978).

Kellogg et al. TaqStart Antibody: "Hot Start" PCR facilitated by a neutralizing monoclonal antibody directed against Taq DNA polymerase. *Bio Techniques.* 16(6)1134-1137 (1994).

Kerkhof. A Comparison of Substrates for Quantifying the Signal fron a Nonradiolabeled DNA Probe. *Anal. Biochem.* 205:359-364 (1992).

Kessler. The digoxigenin:anti-dioxgenin (DIG) technology—a survey on the concept and realization of a novel bioanalytical indicator system. *Mol. Cell Probes* 5:161-205 (1991).

Khrapko et al. Hybridization of DNA with oligonucleotides immobilized in gel: a convenient method for detecting single base substitutions. *Mol. Biol. (Mosk) (USSR).* 25:718-730 (1991).

Kimpton et al. Automated DNA Profiling Employing Multiplex Amplification of Short Tandem Repeat Loci. *PCR Methods and Applications.* 3:13-22 (1993).

King et al. Bridging the Gap. Joining of nonhomologous ends by DNA polymerases. *J. Biol. Chem.* 269(18):13061-13064 (May 6, 1994).

Kong et al. Characterization of a DNA Polymerase from the Hyperthermophile Archaea *Thermococcus litoralis. J. Biol. Chem.* 268(3):1965-1975 (1993).

Kool. Circular Oligonucleotides: New Concepts in Oligonucleotide Design. *Annu. Rev. Biomol. Struct.* 25:1-28 (1996).

Kunkel et al. Rapid and Eficient Site-Specific Mutagenesis without Phenotypic Selection. *Meth. Enzymol.* 154:367-382 (1987).

Kwoh et al. Transcription-based amplification system and detection of amplified human immunodeficiency virus type 1 with a bead-based sandwich hybridization format. *Proc. Natl. Acad. Sci. USA* 86:1173-1177 (Feb. 1989).

Lamture et al. Direct detection of nucleic acid hybridization on the surface of a charge coupled device. *Nucl. Acids Res.* 22(11):2121-2125 (1994).

Landegren et al. A Ligase-Mediated Gene Detection Technique. *Science* 241:1077-1080 (Aug. 26, 1988).

Landegren. Molecular mechanics of nucleic acid sequence amplification. *Trends Genetics.* 9(6):199-202 (Jun. 1993).

Langer et al. Enzymatic synthesis of biotin-labeled polynucleotides: novel nucleic acid affinity probes. *Proc. Natl. Acad. Sci. USA* 78(11):6633-6637 (Nov. 1981).

Lawyer et al. High-level Expression, Purification, and Enzymatic Characterization of Full-length *Thermus aquaticus* DNA Polymerase and a Truncated Form Deficient in 5' to 3' Exonuclease Activity. *PCR Methods Applications* 2(4):275-287 (1993).

LeFrere et al. Towards a new predictor of AIDS progression through the quantitation of HIV-1 DNA copies by PCR in HIV-infected individuals. *Br. J. Haematol.* 82(2):467-471 (1992).

Lesnick and Freier. Relative Thermodynamic Stability of DNA, RNA, and DNA:RNA Hybrid Duplexes: Relationship with Base Composition and Structure. *Biochemistry* 34:10807-10815 (1995).

Letsinger et al. Cholesteryl-conjugated oligonucleotides: Synthesis, properties, and activity as inhibitors of replication of human immunodeficiency virus in cell culture. *Proc. Natl. Acad. Sci. USA* 86:6553-6556 (Sep. 1989).

Letsinger et al. Synthesis of Thymidine Oligonucleotides by Phosphite Triester Intermediates. *J. Am. Chem. Soc.* 9:3655-3661 (Jun. 9, 1981).

Letsinger and Wu. Use of a Stilbenedicarboxamide Bridge in Stabilizing, Monitoring, and Photochemically Altering Folded Conformations of Oligonucleotides. J. Am. CheM. Soc. 117:7323-7328 (1995).

Lichter et al. High-Resolution Mapping of Human Chromosome 11 by in Situ Hybridization with Cosmid Clones. *Science* 247:64-69 (Jan. 5, 1990).

Little et al. Strand Displacement Amplification and Homogeneous Real-Time Detection Incorporated in a Second-Generation DNA Probe System, BDProbeTectET. *Clin. Chem.* 45(6):777-784 (1999).

Liu et al. Rolling Circle DNA Synthesis: Small Circular Oligonucleotides as Efficient Templates for DNA Polymerases. *J. Am. Chem. Soc.* 118:1587-1594 (1996).

Lizardi et al. Mutation detection and single-molecule counting using isothermal rolling-circle amplification. *Nat. Genet.* 19:225-232 (Jul. 1998).

Loakes et al. 5-Nitroindole as an universal base analogue. *Nucl. Acids Res.* 22(20):4039-4043 (1994).

Lockhart et al. Expression monitoring by hybridization to high-density oligonucleotide arrays. *Nat. Biotechnol.* 14:1675-1680 (Dec. 1996).

Lu et al. High Concentration of Peripheral Blood Mononuclear Cells Harboring Infectious Virus Correlates with Rapid Progression of Human Immunodeficiency Virus Type-1 Related Diseases. *JID* 168(5):1165-8116 (Nov. 1993).

Lukyanov et al. Molecule by molecule PCR amplification of complex DNA mixtures for direct sequencing: an approach to in vitro cloning. *Nucl. Acids Res.* 24(11):2194-2195 (1996).

Luo et al. Improving the fidelity of thermus thermophilus DNA ligase. *Nucl. Acids Res.* 24(14):3071-3078 (1996).

Manoharan et al. Chemical Modifications to Improve Uptake and Bioavailability of Antisense Oligonucleotides. *Ann. NY Acad. Sci.* 660:306-309 (1992).

Manoharan et al. Cholic Acid-Oligonucleotide Conjugates for Antisense Applications. *Bioorg. Med. Chem. Lett.* 4(8):1053-1060 (1994).

Manoharan et al. Introduction of a lipophilic thioether tether in the minor groove of nucleic acids for antisense applications. *Bioorg. Med. Chem. Lett.* 3(12):2765-2770 (1993).

Manoharan et al. Lipidic Nucleic Acids. *Tetra. Lett.* 36(21):3651-3654 (1995).

Manoharan et al. Oligonucletoide conjugates: alteration of the pharmacokinetic properties of antisense agents. *Nucleosides & Nucleotides.* 14(3-5):969-973 (1995).

Marshall et al. Detection of HCV RNA by the Asymmetric Gap Ligase Chain Reaction. *PCR Methods and Applications.* 4:80-84 (1994).

Maskos et al. Oligonucleotide hybridizations on glass supports: a novel linker for oligonucleotide synthesized in situ. *Nucl. Acids Res.* 20(7):1679-1684 (1992).

Matsumoto et al. Primary structure of bacteriophage M2 DNA polymerase: conserved segments within protein-priming DNA polymerases and DNA polymerase I of *Escherichia coli. Gene* 84(2):247-255 (1989).

Matteucci et al. Synthesis of Deoxyoligonucleotides on a Polymer Support. *J. Am. Chem. Soc.* 103:3185-3191 (1981).

McCray et al. A new approach to time-resolved studies of ATP-requiring biological systems: laser flash photolysis of caged ATP. *Proc. Natl. Acad. Sci. USA* 77(12):7237-7241 (Dec. 1980).

McGraw et al. Sequence-dependent oligonucleotide-target duplex stabilities: rules from empirical studies with a set of twenty-mers. *Biotechniques.* 8(6):674-678 (1990).

Melton et al. Efficient in vitro synthesis of biologically active RNA and RNA hybridization probes from plasmids containing a bacteriophage SP6 promoter. *Nucl. Acids Res.* 12(18):7035-7056 (1984).

Metzker et al. Termination of DNA synthesis by novel 3'-modified-deoxyribonucleoside 5'-triphosphates. *Nucl. Acids Res.* 22(20):4259-4267 (1994).

Mujumdar et al. Cyanine Dye Labeling Reagents Containng Isothiocyanate Groups. *Cytometry* 10:11-19 (1989).

Mullenix et al. Allergen-specific IgE Detection on Microarrays Using Rolling Circle Amplification: Correlation with in Vitro Assays for Serum IgE. *Clin. Chem.* 47(10):1926-1929 (2001).

Nallur et al. Signal amplification by rolling circle amplification on DNA microarrays. *Nucl. Acids. Res.* 29(23):e118, 2001.

Narang et al. Chemical Synthesis of Deoxynucleotides by the Modified Tester Method. *Meth. Enzymol.* 65:610-620 (1980).

Nazerenko et al. A closed tube format for amplification and detection of DNA based on energy transfer. *Nucl. Acids Res.* 25:2516-2521 (Jun. 1997).

Newton et al. Analysis of any point mutation in DNA. The amplification refractory mutation system (ARMS). *Nucl. Acids Res.* 17(7):2503-2516 (1989).

Nichols et al. A universal nucleoside for use at ambiguous sites in DNA primers. *Nature.* 369(6480):492-493 (Jun. 9, 1994).

Nielsen et al. Peptide Nucleic Acid (PNA). A DNA Mimic with a Peptide Backbone. *Bioconj. Chem.* 5:3-7 (1994).

Nielsen et al. Peptide nucleic acids (PNAs): Potential anti-sense and anti-gene agents. *Anti-Cancer Drug Design.* 8:53-63 (1993).

Nielsen et al. Sequence-Selective Recognition of DNA by Strand Displacement with a Thymine-Substituted Polymide. *Science* 254:1497-1500 (Dec. 1991).

Nikiforov et al. Genetic Bit Analysis: a solid phase method for typing single nucleotide polymorphisms. *Nucl. Acids Res.* 22(20):4167-4175 1994.

Nikiforov et al. The Use of Phosphorothioate Primers and Exonuclease Hydrolysis for the Preparation of Single-stranded PCR Products and their Detection by Solid-phase Hybridization. *PCR Meth. Appl.* 3:285-291 (1994).

Nilsson et al. Padlock probes reveal single-nucleotide differences, parent of origin and in situ distribution of centromeric sequences in human chromosomes 13 and 21. *Nat. Genet.* 16:252-255 (Jul. 1997).

Nilsson et al. Padlock Probes: Circularizing Oligonucleotides for Localized DNA Detection. *Science* 265(5181):2085-2088 (Sep. 30, 1994).

Nuovo et al. In Situ Amplification Using Universal Energy Transfer-labeled Primers. *J. Histochem. Cytochem.* 47(3):273-279 (1999).

Oberhauser et al. Effective incorporation of 2'-O-methyl-oligoribonucleotides into liposomes and enhanced cell association through modification with thiocholesterol. *Nucl. Acids Res.* 20(3):533-538 (1992).

Oda et al. Accurate quantitation of protein expression and site-specific phosphorylation. *Proc. Natl. Acad. Sci. USA* 96:6591-6596 (1999).

Panasenko et al. A Simple, Three-Step Procedure for the Large Scale Purification of DNA Ligase from a Hybrid λ Lysogen Constructed in Vitro. *J. Biol. Chem.* 253(13):4590-4592 (Jul. 10, 1978).

Parker et al. Targeted gene walking polymerase chain reaction. *Nucl. Acids Res.* 19(11):3055-3060 (1991).

Patton et al. Components of the Protein Synthesis and Folding Machinery Are Induced in Vascular Smooth Muscle Cells by Hypertrophic and Hyperplastic Agents. *J. Biol. Chem.* 270(36):21404-21410 (Sep. 8, 1995).

Patton. Making Blind Robots See: The Snyergy Between Fluorscent Dyes and Imaging Devices in Automated Proteomics. *Biotechniques* 28(5):944-957 (2000).

Patton. Proteome analysis II. Protein subcellular redistribution: linking physiology to genomics via the proteome and separation techniques involved. *J Chromatogr. B* 722:203-223 (1999).

Pease et al. Light-generated oligonucleotide arrays for rapid DNA sequence analysis. *Proc. Natl.Acad. Sci. USA* 91(11):5022-5026 (May 1994).

Piatak et al. High Levels of HIV-1 in Plasma During All Stages of Infection Determined by Competitive PCR. *Science* 259:1749-1754 (Mar. 19, 1993).

Pillai. Photoremovable Protecting Groups in Organic Synthesis. *Synthesis* 1-26 (1980).

Pless and Letsinger. Solid support synthesis of oligothymidylates using phosphorochloridates and 1-alkylmidazoles. *Nucl. Acids Res.* 2(6):773-786 (Jun. 1975).

Pokrovskaya et al. In Vitro transcription: Preparative RNA Yields in Analytical Scale Reactions. *Anal. Biochem.* 220:420-423 (1994).

Porstmann et al. Quantitation of 5-Bromo-2-Deoxyuridine Incorporation into DNA: an Enzyme Immunoassay for the Assessment of the Lymphiod Cell Proliferative. *J. Immunol. Meth.* 82:169-179 (1985).

Prakash and Kool. Structural Effects in the Recognition of DNA by Circular Oligonucleotides. *J. Amer. Chem. Soc.* 114:3523-3527 (1992).

Prober et al. A System for Rapid DNA Sequencing with Fluorscent Chain-Terminating Dideoxynucleotides. *Science* 238:336-341 (1987).

Ramsing et al. Helix-Coli Transsition of Parallel-Stranded DNA. Thermodynamics of Hairpin and Linear Duplex Oligonucleotides. *Biochemistry* 28:9528-9535 (1989).

Richards et al. Conditional Mutator Phenotypes in hMSH2-Deficient Tumor Cells Lines. *Science* 277:1523-1526 (Sep. 5, 1997).

Ried et al. Simultaneous visualization of seven different DNA probes by in situ hybridization using combinational fluorescence and digital imaging microscopy. *Proc. Natl. Acad. Sci. USA* 89(4):1388-1392 (1982).

Rigler et al. Difference in the Mechanism of Stimulation of T7 DNA Polymerase by Two Binding Modes of *Escherichia coli* Single-stranded DNA-binding Protein. *J. Biol. Chem.* 270(15):8819-8919 (Apr. 14, 1995).

Rychlik et al. Optimizaton of the annealing temperature for DNA amplification in vitro. *Nucl. Acids Res.* 18(21):6409-6412 (1990).

Rys et al. Preventing False Positives: Quantitative Evaluatio of Three Protocols for Inactivation of Polymerase Chain Reaction Amplication Products. *J. Clin. Microbiol.* 31(9):2356-2360 (Sep. 1993).

Saiki et al. Primer-Directed Enzymatic Amplification of DNA with a Thermostable DNA Polymerase. *Science* 239:487-491 (Jan. 29, 1988).

Saison-Behmoaras et al. Short modified antisense oligonucleotides directed against Ha-ras point mutation induce selective cleavage of the mRNA and inhibit T24 cells proliferation. *EMBO J.* 10(5):1111-1118 (1991).

Saksela et al. Human immunodeficiency virus type 1 mRNA expression in peripheral blood cells predicts disease progression independently of the numbers of CD4+ lymphocytes. *Proc. Natl. Acad. Sci. USA* 91(3):1104-1108 (1994).

Sanghvi. Heterocyclic base modifications in nucleic acids and their applications in antisense oligonucleotides. *Antisense Research and Applications*. (Crooke et al, eds., CRC Press) Chapters 15-16, pp. 273-301 (1993).

Sano et al. Detection of heavy methylation in human repetitive DNA subsets by a monoclonal antibody against 5-methylcytosine. *Biochim. Biophys. Acta.* 951:157-165(1988).

Saris et al. Blotting of RNA onto RNA exchange paper allowing subsequent characterization by in situ translation in addition to blot hybridization. *Nucl. Acids Res.* 10(16):4831-4843 (1982).

Schena et al. Parallel human genome analysis: Microarray-based expression monitoring of 1000 genes. *Proc. Natl. Acad. Sci. USA* 93:10614-10619 (Oct. 1994).

Schena et al. Quantitative Monitoring of Gene Expression Patterns with s Complementary DNA Microarray. *Science* 270:467-470 (Oct. 20, 1995).

Schenborn et al. A novel transcription property of SP6 and T7 RNA polymerases: dependence on template structure. *Nucl. Acids Res.* 13(17):6223-6236 (1985).

Schwarz. Improved yields of long PCR products using gene 32 protein. *Nucl. Acids Res.* 18(4):1079 (1990).

Schweitzer and Kingsmore. Combining nucleic acid amplification and detection. *Curr. Opin. Biotech.* 12(1):21-27 (Feb. 2001).

Schweitzer et al. Immunoassays with rolling circle DNA amplification: a versatile platform for ultrasensitive antigen detection. *Proc. Natl. Acad. Sci. USA* 97(18):10113-10118 (Aug. 29, 2000).

Schweitzer et al. Multiplexed protein profiling on microarrays by rolling-circle amplification. *Nat. Biotech.* 20:359-365 (2002).

Shea et al. Synthesis, hybridization properties and antiviral activity of lipid-oligodeoxynucleotide conjugates. *Nucl. Acids Res.* 18(13):3777-3783 (1990).

Shumaker et al. Mutation Detection by Solid Phase Primer Extension. *Hum. Mutat.* 7(4):346-354 (1996).

Siegal et al. A Novel DNA Helicase from Calf Thymus. *J. Biol. Chem.* 267(19):13629-13635 (Jul. 5, 1992).

Simpson. The Natural Somatic Mutation Frequency and Human Carcinogenesis. *Adv. Cancer Res.* 71:209-240 (1997).

Skaliter et al. Rolling circle DNA replication in vitro by a complex of herpes simplex virus type 1-encoded enzymes. *Proc. Natl. Acad. Sci. USA* 91(22):10665-10669 (Oct. 1994).

Speicher et al. Karyotyping human chromosomes by combinatorial multi-fluor FISH. *Nat. Genet.* 12(4):368-375 (1996).

Stimpson et al. Real-time detection of DNA hybridization and metling on oligonucleotide arrays by using optical wave guides. *Proc. Natl. Acad. Sci. USA* 92(14):6379-6383 (Jul. 1995).

Strauss et al. Quantitative measure of calretinin and β-actin mRNAIN rat brain micropunches without prior isolation of RNA. *Mol. Brain Res.* 20:229-239 (1993).

Studier et al. Use of T7 RNA Polymerase to Direct Expression of Cloned Genes. *Meth. Enzymol.* 185:60-89 (1990).

Stump et al. The use of modified primers ot eliminate cycle sequencing artifacts. *Nucl. Acids Res.* 27(23):4642-4648 (1999).

Svinarchuk et al. Inhibition of HIV proliferation in MT-4 cells by antisense oligonucleotide conjugated to lipophilic groups. *Biochimie.* 75:49-54 (1993).

Syvänen et al. Fast quantification of nucleic acid hybrids by affinity-based hybrid collection. *Nucl. Acids Res.* 14(12):5037-5049 (1986).

Tabor et al. Selective Inactivation of the Exonuclease Activity of Bacteriophage T7 DNA Polymerase by in Vitro Mutagenesis. *J. Biol. Chem.* 264(11):6447-6458 (Apr. 15, 1989).

Tabor and Richardson. Selective Oxidation of the Exonuclease Domain of Bacteriophage T7 DNA Polymearase. *J. Biol. Chem.* 262(32):15330-15333 (Nov. 15, 1987).

Thelwell et al. Mode of action and application of Scorpion primers to mutation detection. *Nucl. Acids Res.* 28(19):3752-3761 (2000).

Thomas et al. Cascade rolling circle amplification, a homogenous fluorescence detection system for DNA diagnostics. *Clin. Chem.* 43:2219, Abs. 38 (1997).

Thorbjarnardottir et al. Cloning and sequence analysis of the DNA ligase-encoding gene of *Rhodothermus marinus*, overproduction, purification and characterization of two thermophilic DNA ligases. *Gene* 161:1-6 (1995).

Tsurumi et al. Functional Interaction between Epstein-Barr Virus DNA Polymerase Catalytic Subunit and Its Accessory Subunit In Vitro. *J. Viral.* 67(12):7648-7653 (Dec. 1993).

Tyagi and Kramer. Molecular Beacons: Probes that Fluoresce upon Hybridization. *Nat. Biotech.* 14:303-308 (Mar. 1996).

Tyagi et al. Extremely sensitive, background-free gene detection using binary probes and Qβ replicase. *Proc. Natl. Acad. Sci. USA* 93:5395-5400 (May 1996).

Uemori et al. Cloning of the DNA Polymerase Gene of *Bacillus caldotenax* and Characterizaion of the Gene Product *J. Biochem.* 113:401-410 (1993).

Velculescu et al. Serial Analysis of Gene Expression. *Science* 270:484-487 (Oct. 20, 1995).

Villemain et al. The N-Terminal B-Domain of T4 Gene 32 Protein Mdulates the Lifetime of Cooperatively Bound Gp32-ss Nucleic Acid Complexes. *Biochemistry* 35:14395-14404 (1996).

Vogelstein et al. Supercoiled Loops and Eucaryotic DNA Replication. *Cell* 22:79-85 (Nov. 1980).

Voisey et al. Interrogation of Multimeric DNA Amplification Products by Competitive Primer Extension Using *Bst* DNA Polymerase (Large Fragment). *Biotechniques* 31(5):1122-1129 (Nov. 2001).

Waggoner. Covalent Labeling of Proteins and Nucleic Acids with Fluorophores. *Meth. Enzymol.* 246:362-373 (1995).

Walker and Linn. Detection of *Mycobacterium tuberculosis* DNA with thermophilic strand displacement amplification and fluorescence polarization. *Clin. Chem.* 42(10)1604-1608 (1996).

Walker et al. Isothermal in vitro amplification of DNA by a restriction enzyme/DNA polymerase system. *Proc. Natl. Acad. Sci. USA* 89:392-396 (Jan. 1992).

Walker et al. Strand displacement amplification—an isothermal, in vitro DNA amplification technique. *Nucl. Acids Res.* 20(7):1691-1696 (1992).
Walter and Strunk. Strand displacement amplification as an in vitro model for rolling-circle replication: deletion formation and evolution during serial transfer. *Proc. Natl. Acad. Sci. USA* 91:7937-7941 (Aug. 1994).
Wang and Kool. Circular RNA oligonucleotide. Synthesis, nucleic acid binding properties, and a comparison with circular DNAs. *Nucl. Acids. Res.* 22(12):2326-2333 (1994).
Wang et al. Large-Scale Identification, Mapping, and Genotyping of Single-Nucleotide Polymorphisms in the Human Genome. *Science* 280:1077-1082 (May 15, 1998).
Wansink et al. Fluorescent Labeling of Nascent RNA Reveals Transcription by RNA Polymerase II in Domains Scattered Throughout the Nucleus. *J. Cell Biol.* 122(2):283-293 (Jul. 1993).
Wiedmann et al. Ligase chain reaction (LCR)—overview and applications. *PCR Methods and Applications*. (Cold Spring Harbor Laboratory Press, Cold Spring Harbor, NY, 1994) [pp. S51-S64].
Winn-Deen et al. Non-radioactive detection of *Mycobacterium tuberculosis* LCR products in a microtitre plate format. *Mol. Cell. Probes* (England) 7(3):179-186 (1993).
Wirth and Romano. Staining methods in gel electrophoresis, including the use of multiple detection methods. *J. Chromatogr. A.* 698:123-143 (1995).
Young et al. Quantitative Analysis of Solution Hybridization. *Nucleic Acid Hybridisation*: A Practical Approach. (IRL Press, 1985) pp. 47-71.
Yu et al. Cyanine dye dUTP analogs for enzymatic labeling of DNA probes. *Nucl. Acids Res.* 22(15):3226-3232 (1994).
Zehavi et al. Light-Sensitive Glycosides. I. 6-Nitroveratryl p-D-Glucopyranoside and 2-Nitrobenzyl p-D-Glucopyranoside. *J. Org. Chem.* 37(14):2281-2288 (1972).
Zhang et al. Whole genome amplification from a single cell: Implications for genetic analysis. *Proc. Natl. Acad. Sci. USA* 89:5847-5851 (Jul. 1992).
Zhu et al. Global Analysis of Protein Activities Using Proteome Chips. *Science* 293:2101-2105 (Sep. 14, 2001).
Zhu et al. Purification and characterization of PRD1 DNA polymerase. *Biochimica Biophysica Acta*. 1219(2):267-276 (1994).
Zijderveld et al. Helix-Destabilizing Properties of the Adenovirus DNA-Binding Protein. *J. Virol.* 68(2):1158-1164 (Feb. 1994).
Agüero et al. (2000). A random sequencing approach for the analysis of the *Trypanosoma cruzi* genome: general structure, large gene and repetitive DNA families, and gene discovery. Genome Res. 10(12): 1996-2005.
Alsmadi et al. (2009) Specific and complete human genome amplification with improved yield achieved by phi29 DNA polymerase and a novel primer at elevated temperature. BMC Res Notes. 2: 48.
Altschul et al. (1997) Gapped BLAST and PSI-BLAST: a new generation of protein database search programs. Nucleic Acids Res. 25(17): 3389-402.
Andras et al. (2001) Strategies for signal amplification in nucleic acid detection. Mol Biotechnol. 19(1): 29-44.
Ansari-Lari et al. (1996) Improved ligation-anchored PCR strategy for identification of 5' ends of transcripts. Biotechniques. 21(1): 34-6, 38.
Apweiler et al. (2001) The InterPro database, an integrated documentation resource for protein families, domains and functional sites. Nucleic Acids Res. 29(1): 37-40.
Armitage et al. (1998) Hairpin-forming peptide nucleic acid oligomers. Biochemistry. 37(26): 9417-25.
Arn et al. (1996) The 2'-5' RNA ligase of *Escherichia coli*. Purification, cloning, and genomic disruption. J. Biol. Chem. 271(49): 31145-53.
Asseline et al. (1992) Solid-phase preparation of 5',3'-heterobifunctional oligodeoxyribonucleotides using modified solid supports. Tetrahedron. 48(7): 1233-1254.
Atencia et al. (1999) T4 RNA ligase catalyzes the synthesis of dinucleoside polyphosphates. Eur J Biochem. 261(3): 802-11.
Auer et al. (1996) Selective amplification of RNA utilizing the nucleotide analog dITP and *Thermus thermophilus* DNA polymerase. Nucleic Acids Res. 24(24): 5021-5.

Ausubel et al. Current Protocols in Molecular Biology, John Wiley & Sons, 1:1.6.1-1.6.6 (1988).
Baldauf et al. (2000) A kingdom-level phylogeny of eukaryotes based on combined protein data. Science. 290(5493): 972-7.
Becker et al. (1999) LMPCR for detection of oligonucleotide-directed triple helix formation: a cautionary note. Antisense Nucleic Acid Drug Dev. 9(3): 313-6.
Becker et al. (2000) Applied environ microbial, 66(11): 4945-4953.
Becker et al. (2000) PCR bias in ecological analysis: a case study for quantitative Taq nuclease assays in analyses of microbial communities. Appl Environ Microbiol. 66(11): 4945-53.
Beier et al. (1999) Versatile derivatisation of solid support media for covalent bonding on DNA-microchips. Nucleic Acids Res. 27(9): 1970-7.
Beigelman et al. Synthesis of 1-deoxy-d-ribofuranose phosphoramidite & the incorporation of abasic nucleotides in stem-loop II of a hammerhead ribozyme. Original. pp. 1715-1720. vol. 4, Issue 14, Bioorganic & Medicinal Chemistry Letters., 1994.
Benjamin Lewis, Genes 1983, John Wiley & Sons, New York, US, pp. 515-518.
Betz et al. (1981) Variants of a cloned synthetic lactose operator. I. A palindromic dimer lactose operator derived from one stand of the cloned 40-base pair operator. Gene. 13(1): 1-12.
Bi et al. (1997) CCR: a rapid and simple approach for mutation detection. Nucleic Acids Res. 25(14): 2949-51.
Birnboim HC. (1983) A rapid alkaline extraction method for the isolation of plasmid DNA. Methods Enzymol. 100: 243-255.
Blain et al. (1995) Effects on DNA synthesis and translocation caused by mutations in the RNase H domain of Moloney murine leukemia virus reverse transcriptase. J Virol. 69(7): 4440-52.
Blanc et al. (1999) The mitochondrial RNA ligase from *Leishmania tarentolae* can join RNA molecules bridged by a complementary RNA. J. Biol. Chem. 274(34): 24289-96.
Bloch et al. (1988) Alpha-anomeric DNA: beta-RNA hybrids as new synthetic inhibitors of *Escherichia coli* RNase H, *Drosophila* embryo RNase H and M-MLV reverse transcriptase. Gene. 72(1-2): 349-60.
Bonaldo et al. (1996) Normalization and subtraction: two approaches to facilitate gene discovery. Genome Res. 6(9): 791-806.
Boore et al. (2005) Sequencing and comparing whole mitochondrial genomes of animals. +Methods Enzymol. 395: 311-348.
Brandenburg et al. Branched oligodeoxynucleotides: a new synthetic strategy and formation of strong intra- and intermolecular triple helical complexes. Bioorganic & Medicinal Chemistry Letters. 5(8): 791-794.
Brennan et al. (1983) Using T4 RNA ligase with DNA substrates. Methods Enzymol. 100: 38-52.
Brownstein et al. (1996) Modulation of non-templated nucleotide addition by Taq DNA polymerase: primer modifications that facilitate genotyping. Biotechniques. 20(6): 1004-6, 1008-10.
Buchanan et al. (2000) Long DOP-PCR of rare archival anthropological samples. Hum Biol. 72(6): 911-25.
Cameron et al. (2000) A sea urchin genome project: sequence scan, virtual map, and additional resources. Proc Natl Acad Sci U S A. 97(17): 9514-8.
Carninci et al. (1998) Thermostabilization and thermoactivation of thermolabile enzymes by trehalose and its application for the synthesis of full length cDNA. Proc Natl Acad Sci U S A. 95(2): 520-4.
CDP-Star CSPD & AMPPD Substrates for A1 Phosphatase. Printout on Mar. 24, 2000 from webpage (www.tropix.com/alkasubs.htm).
Chandler DP. (1998) Redifining relativity: quantitative PCR at low template concentrations for industrial and environmental microbiology. J. Indust. Microbiol. Biotech. 21: 128-140.
Lee et al., 2nd et al. (1998) Coordinated leading and lagging strand DNA synthesis on a minicircular template. Mol Cell. (7): 1001-10.
Chen et al. (1998) Amplification of closed circular DNA in vitro. Nucleic Acids Res. 26(23): 1126-7.
Choo et al. (1994) Differentiation-independent constitutive expression of the human papillomavirus type 16 E6 and E7 oncogenes in the CaSki cervical tumour cell line. J Gen Virol. 75 (Pt 5): 1139-7.
Connolly BA. (1985) Chemical synthesis of oligonucleotides containing a free sulphydryl group and subsequent attachment of thiol specific probes. Nucleic Acids Res. 13(12): 4485-502.

Connolly BA. (1987) The synthesis of oligonucleotides containing a primary amino group at the 5'-terminus. Nucleic Acids Res. 15(7): 3131-3139.

Cremer et al. (1988) Detection of chromosome aberrations in metaphase and interphase tumor cells by in situ hybridization using chromosome-specific library probes. Hum Genet. 80(3): 235-46.

Crollius et al. (2000) Characterization and repeat analysis of the compact genome of the freshwater pufferfish *Tetraodon nigroviridis*. Genome Res. 10(7): 939-49.

Damha et al. (1998) Synthesis of a branched DNA/RNA chimera similar to the msDNA molecule of *Myxococcus Xanthus*. Tetrahedron Letters. 39(23): 3907-3910.

Davies et al. (1999) Profiling of amyloid beta peptide variants using SELDI Protein Chip arrays. Biotechniques. 27(6): 1258-61.

Davis et al. (1980) A Manual for Genetic Engineering. Advanced Bacterial Genetics. Cold Spring Harbor Laboratory. Cold Spring Harbor, NY.

de Baar et al. (2001) Single rapid real-time monitored isothermal RNA amplification assay for quantification of human immunodeficiency virus type 1 isolates from groups M, N, and O. J Clin Microbiol. 39(4): 1378-84.

de Vega et al. (1997) An invariant lysine residue is involved in catalysis at the 3'-5' exonuclease active site of eukaryotic-type DNA polymerases. J Mol Biol. 270(1): 65-78.

Dean et al. (2002) Comprehensive human genome amplification using multiple displacement amplification. Proc Natl Acad Sci USA. 99(8): 5261-66.

Detter et al. (2002) Isothermal strand-displacement amplification applications for high-throughput genomics. Genomics. 80(6): 691-98.

Dreyer et al. (1985) Sequence-specific cleavage of single-stranded DNA: oligodeoxynucleotide-EDTA X Fe(II). Proc Natl Acad Sci U S A. 182(4): 968-72.

Durand et al. (1990) Circular dichroism studies of an oligodeoxyribonucleotide containing a hairpin loop made of a hexaethylene glycol chain: conformation and stability. Nucleic Acids Res. 18(21): 6353-9.

Eads et al. (1999) CpG island hypermethylation in human colorectal tumors is not associated with DNA methyltransferase overexpression. Cancer Res. 59(10): 2302-2306.

Eberwine et al. (1992) Analysis of gene expression in single live neurons. Proc Natl Acad Sci USA. 89(7): 3010-3014.

Eckert et al. (1991) DNA polymerase fidelity and the polymerase chain reaction. PCR Methods Appl. 1(1): 17-24.

Egholm et al. (1992) Peptide nucleic acids (PNA). Oligonucleotide analogs with an achiral peptide backbone. J. Am. Chem. Soc., 114(5): 1895-1897.

Ekins et al. (1991) Multianalyte microspot immunoassay—microanalytical "compact disk" of the future. Review. Clin Chem. 37(11): 1955-67.

Fermentas Web Page. Thermophilic DNA Polymerase (Copyright 2008).

Fu et al. (1994) Hammerhead Ribozymes Contianing Non-Nucleoside Linkers are Active RNA Catalysts. J. Am. Chem. Soc. 116: 4591-4598.

Galli et al. (1995) Transcriptional analysis of rolling circle replicating plasmid pVT736-1: evidence for replication control by antisense RNA. J Bacteriol. 177(15): 4474-80.

Gasparini et al. (1999) Analysis of 31 CFTR mutations by polymerase chain reaction/oligonucleotide ligation assay in a pilot screening of 4476 newborns for cystic fibrosis. J Med Screen. 6(2): 67-9.

Ge H. (2000) UPA, a universal protein array system for quantitative detection of protein-protein, protein-DNA, protein-RNA and protein-ligand interactions. Nucleic Acids Res. 28(2): e3.

GE Healthcare. (2010) Frequently Asked Questions—TempliPhi.

Gillespie et al. (2000) HLA class II typing of whole genome amplified mouth swab DNA. Tissue Antigens. 56(6): 530-8.

Grzybowski et al. (1993) Synthesis and antibody-mediated detection of oligonucleotides containing multiple 2,4-dinitrophenyl reporter groups. Nucleic Acids Res. 21(8): 1705-12.

Guillier-Gencik et al. (1999) Generation of whole-chromosome painting probes specific to each chicken macrochromosome. Cytogenet Cell Genet. 87(3-4): 282-5.

Gumport et al. (1981) T4 RNA ligase as a nucleic acid synthesis and modification reagent. Gene Amplif Anal. 2: 313-45.

Gupta et al. (1990) A universal solid support for the synthesis of 3'-thiol group containing oligonucleotides. Tetrahedron Letters. 31(17): 2471-2474.

Haaf et al. (1994) High resolution ordering of YAC contigs using extended chromatin and chromosomes. Hum Mol Genet. 3(4): 629-33.

Harada et al. (1993) In vitro selection of optimal DNA substrates for T4 RNA ligase. Proc Natl Acad Sci U S A. 90(4): 1576-9.

Harada et al. (1994) In vitro selection of optimal DNA substrates for ligation by a water-soluble carbodiimide. J Mol Evol. 38(6): 558-60.

Haralambidis et al. (1987) Preparation of base-modified nucleosides suitable for non-radioactive label attachment and their incorporation into synthetic oligodeoxyribonucleotides. Nucleic Acids Res. 15(12): 4857-76.

Harper et al. (1999) Recent advances and future developments in PGD. Prenat Diagn. 19(13): 1193-9.

Higgins et al. Addition of oligonucleotides to the 5'-terminus of DNA by T4 RNA ligase. Nucleic Acids Res. 6(3): 1013-24.

Higgins et al. DNA joining enzymes: a review. Methods Enzymol. 68: 50-71.

Hinton et al. (1978) T4 RNA Ligase joins 2'-deoxyribonucleoside 3', 5'-bisphosphates to oligodeoxyribonucleotides. Biochemistry. 17(24): 5091-7.

Hinton et al. (1979) The synthesis of oligodeoxyribonucleotides using RNA ligase. Nucleic Acids Res. 7(2): 453-64.

Hinton et al. (1982) The preparative synthesis of oligodeoxyribonucleotides using RNA ligase. Nucleic Acids Res. 10(6): 1877-94.

Holton et al. (1991) A simple and efficient method for direct cloning of PCR products using ddT-tailed vectors. Nucleic Acids Res. 19(5): 1156.

Horn et al. (1997) Chemical synthesis and characterization of branched oligodeoxyribonucleotides (bDNA) for use as signal amplifiers in nucleic acid quantification assays. Nucleic Acids Res. 25(23): 4842-9.

Hsuih et al. (1996) Novel, ligation-dependent PCR assay for detection of hepatitis C in serum. J Clin Microbiol. 34(3): 501-7.

Huryn et al. (1992) AIDS-driven nucleoside chemistry. Chem Rev. 92: 1745-1768.

Iakobashvili et al. (1999) Low temperature cycled PCR protocol for Klenow fragment of DNA polymerase I in the presence of proline. Nucleic Acids Res. 27(6): 1566-8.

Innis et al. (1988) DNA sequencing with *Thermus aquaticus* DNA polymerase and direct sequencing of polymerase chain reaction-amplified DNA. Proc Natl Acad Sci U S A. 85(24): 9436-40.

Intergen Company. Amplifluor$^{TM}$ Apoptosis Gene System. (4 pages), Jan. 3, 2002.

Intergen Company. Principles of the Amplifluor$^{TM}$ Universal Amplification and Detection System Procedure. (2 pages) Jan. 3, 2002.

Itaka et al. (2002) Evaluation by fluorescence resonance energy transfer of the stability of nonviral gene delivery vectors under physiological conditions. Biomacromolecules. 3(4): 841-5.

Iuodka et al. (1991) [Substrate specificity of T4 RNA-ligase. The role of phosphate nucleotide residues in the formation of a covalent Amp-RNA-ligase complex]. [Article in Russian]. Biokhimiia. 56(5): 798-805.

Jablonski et al. (1986) Preparation of oligodeoxynucleotide-alkaline phosphatase conjugates and their use as hybridization probes. Nucleic Acids Res. 14(15): 6115-28.

Jalanko et al. (1992) Screening for defined cystic fibrosis mutations by solid-phase minisequencing. Clin Chem. 38(1): 39-43.

Kabat. Structural Concepts in Immunology and Immunohistochemistry. Holt, Rinehart and Winston, Inc. (1968) pp. 162-168.

Kalnik et al. (1988) NMR studies of abasic sites in DNA duplexes: deoxyadenosine stacks into the helix opposite the cyclic analogue of 2-deoxyribose. Biochemistry. 27(3): 924-31.

Kaluz et al. (1995) Enzymatically produced composite primers: an application of T4 RNA ligase-coupled primers to PCR. Biotechniques. 19(2): 182-4, 186. 2000.

Kang et al. (2000) Transcript quantitation in total yeast cellular RNA using kinetic PCR. Nucleic Acids Res. 28(2): e2.

Kim et al. (1999) Whole genome amplification and molecular genetic analysis of DNA from paraffin-embedded prostate adenocarcinoma tumor tissue. J Urol. 162(4): 1512-18.

Kim et al. (2000) Regulation of cell growth and HPV genes by exogenous estrogen in cervical cancer cells. Int J Gynecol Cancer. 10(2): 157-164.

Kinoshita et al. (1997) Fluorescence-, isotope- or biotin-labeling of the 5'-end of single-stranded DNA/RNA using T4 RNA ligase. Nucleic Acids Res. 25(18): 3747-8.

Klein et al. (1999) Comparative genomic hybridization, loss of heterozygosity, and DNA sequence analysis of single cells. Proc Natl Acad Sci USA. 96(8): 4494-9.

Kling J. Genetic Engineering Without Restriction. Double Twist. Reviews, Jul. 24, 2000.

Kobayashi et al. (1995) Fluorescence-based DNA minisequence analysis for detection of known single-base changes in genomic DNA. Mol Cell Probes. 9(3): 175-82.

Komura et al. (1998) Terminal transferase-dependent PCR: a versatile and sensitive method for in vivo footprinting and detection of DNA adducts. Nucleic Acids Res. 26(7): 1807-11.

Kononen et al. (1998) Tissue microarrays for high-throughput molecular profiling of tumor specimens. Nat Med. 4(7): 844-7.

Kornberg et al. (1992) DNA Replication, 2nd Edition, WH Freeman and Company, New York, US, pp. 20-21, 503-503.

Kumar et al. (1991) A simple method for introducing a thiol group at the 5'-end of synthetic oligonucleotides. Nucleic Acids Res. 19(16): 4561. No abstract available.

Kuukasjärvi et al. (1997) Optimizing DOP-PCR for universal amplification of small DNA samples in comparative genomic hybridization. Genes Chromosomes Cancer. 18(2): 94-101.

Laffler et al. (1993) The ligase chain reaction in DNA-based diagnosis. Ann Biol Clin (Paris). 51(9): 821-6.

Lantz et al. (2000) Biotechnical use of polymerase chain reaction for microbiological analysis of biological samples. Biotechnol Annu Rev. 5: 87-130.

Laval et al. (1989) Structural organization and expression of amplified chromosomal sequences, which include the rudimentary gene, in cultured *Drosophila* cells resistant to N-(phosphonacetyl)-L-aspartate. Mol Gen Genet. 220(1): 102-12.

Lee HH. (1996) Ligase chain reaction. Biologicals. 24(3):197-9.

Lim et al. (1997) Synthesis of DNA Dumbbells: Chemical vs. Enzymatic Ligation of Self-Complementary Oligonucleotides. Pages 41-51 Nucleosides & Nucleotides 16(1*2).

Lin et al. (1995) Single-site polymerase chain reaction through single oligonucleotide ligation. Anal Biochem. 231(2): 449-52.

Ling et al. (1997) Approaches to DNA mutagenesis: an overview. Anal Biochem. 254(2): 157-78.

Liu et al. (1993) Mapping the 5' and 3' ends of *Tetrahymena thermophila* mRNAs using RNA ligase mediated amplification of cDNA ends (RLM-RACE). Nucleic Acids Res. 21(21): 4954-60.

Lizardi et al. (1997) FISH with a twist. Nat Genet. 16(3): 217-8.

Löffert et al. (1998) PCRoptimziation: degenerate primers. Qiagen News. (Issue 2).

Lyons et al. (1994) Immunosuppressant FK506 promotes neurite outgrowth in cultures of PC12 cells and sensory ganglia. Proc Natl Acad Sci USA. 91(8): 3191-3195.

MacKellar et al. (1992) Synthesis and physical properties of anti-HIV antisense oligonucleotides bearing terminal lipophilic groups. Nucleic Acids Res. 20(13):3411-7.

Mads et al. (2000) Branched oligonucleotides containing bicyclic nucleotides as branching points and DNA or LNA as triplex forming branch. pp. 1853-1856. Bioorganic & Medicinal Chemistry Letters. vol. 10, Issue 16, 21 pp. 1853-1856.

Mahadeva et al. (1998) A simple and efficient method for the isolation of differentially expressed genes. J Mol Biol. 284(5): 1391-8.

Malboeuf et al. (2001) Thermal effects on reverse transcription: improvement of accuracy and processivity in cDNA synthesis. Biotechniques. 30(5): 1074-8, 1080, 1082, passim.

Maniatis et al. (1982) Molecular Cloning: A Laboratory Manual. (Cold Spring Harbor Laboratory) Eds, pp. 280-281.

Marshall et al. (1997) A biopolymer by any other name would bind as well: a comparison of the ligand-binding pockets of nucleic acids and proteins. Structure. 5(6): 729-734.

Mathur et al. (2000) Cervical epidermal growth factor-receptor (EGF-R) and serum insulin-like growth factor II (IGF-II) levels are potential markers for cervical cancer. Am J Reprod Immunol. 44(4): 222-30.

Matray et al. (1998) Selective and Stable DNA Base Pairing without Hydrogen Bonds. J Am. Chem. Soc. 120(24): 6191-6192.

Matray et al. (1999) A specific partner for abasic damage in DNA. Nature. 399(6737): 704-8.

Matz et al. (1999) Amplification of cDNA ends based on template-switching effect and step-out PCR. Nucleic Acids Res. 27(6): 1558-1560.

McCoy et al. (1980) T4 ribonucleic acid ligase joins single-strand oligo (deoxyribonucleotides). Biochemistry. 19(4): 635-42.

Mishra et al. (1995) Improved leishmanicidal effect of phosphorotioate antisense oligonucleotides by LDL-mediated delivery. Biochim Biophys Acta. 1264(2): 229-37.

Monji et al. (1987) A novel immunoassay system and bioseparation process based on thermal phase separating polymers. Appl Biochem Biotechnol. 14(2): 107-20.

Moore et al. (1992) Site-specific modification of pre-mRNA: the 2'-hydroxyl groups at the splice sites. Science. 256(5059): 992-7.

Moretti et al. (1998) Enhancement of PCR amplification yield and specificity using AmpliTaq Gold DNA polymerase. Biotechniques. 25(4): 716-22.

Morvan et al. (1986) alpha-DNA. I. Synthesis, characterization by high field 1H-NMR, and base-pairing properties of the unnatural hexadeoxyribonucleotide alpha[d(CpCpTpTpCpC)] with its complement beta-[d(GpGpApApGpG)]. Nucleic Acids Res. 14(12): 5019-35.

Myers et al. (1991) Reverse transcription and DNA amplification by a *Thermus thermophilus* DNA polymerase. Biochemistry. 30(31): 7661-6.

Naritsin et al. (1991) Melting of oligodeoxynucleotides with various structures. J. Biomol. Struct. Dyn. 8(4): 813-25.

Nelson et al. (2002) TempliPhi, phi29 DNA polymerase based rolling circle amplification of templates for DNA sequencing. Biotechniques. Suppl:44-7.

New Englad BioLabs. Product Information for M-MuLV Reverste Trasncriptase, Apr. 4, 2007.

Nguyen et al. Solid phase synthesis of oligo-α- and oligo-β-deoxynucleotidescovalently linked to an acridine. pp. 5905-5908. Tetrahedron Lett. 29(46): 5905-5908., 1988.

Nilsson et al. (2002) Real-time monitoring of rolling-circle amplification using a modified molecular beacon design. Nucleic Acids Res. 30(14): e66.

Nycz et al. (1998) Quantitative reverse transcription strand displacement amplification: quantitation of nucleic acids using an isothermal amplification technique. Anal Biochem. 259(2): 226-34.

Okayama et al. (1982) High-efficiency cloning of full-length cDNA. Mol Cell Biol. 2(2): 161-170.

Ørum et al. (1993) Single base pair mutation analysis by PNA directed PCR clamping. Nucleic Acids Research. 21(23): 5332-5336.

Ott et al. (1987) Protection of oligonucleotide primers against degradation by DNA polymerase I. Biochemistry. 26(25): 8237-41.

Oyama et al. (1988) Avian myeloblastosis virus reverse transcriptase is easier to use than the Klenow fragment of DNA polymerase I for labeling the 3'-end of a DNA fragment. Anal Biochem. 172(2): 444-50.

Park et al. (1996) Detection of hepatitis C virus RNA using ligation-dependent polymerase chain reaction in formalin-fixed, paraffin-embedded liver tissues. Am J Pathol. 149(5): 1485-91.

Parra et al. (1993) High resolution visual mapping of stretched DNA by fluorescent hybridization. Nat Genet. 5(1): 17-21.

Partha et al. (1990) Novel Thymidine Analogues via Reaction of Unprotected 5'- Deoxy-5'-iodothymidine with Dianions. vol. 31, Issue 10, pp. 1777-1780.

Patel et al. (1996) Formation of chimeric DNA primer extension products by template switching onto an annealed downstream oligonucleotide. Proc Natl Acad Sci USA. 93(7): 2969-2974.

Paulson et al. (1999) Loss of heterozygosity analysis using whole genome amplification, cell sorting, and fluorescence-based PCR. Genome Res. 9(5): 482-91.

Paunio et al. (1996) Preimplantation diagnosis by whole-genome amplification, PCR amplification, and solid-phase minisequencing of blastomere DNA. Clin Chem. 42(9): 1382-90.

Petric et al. (1991) Ligation with T4 RNA ligase of an oligodeoxyribonucleotide to covalently-linked cross-sectional base-pair analogues of short, normal, and long dimensions. Nucleic Acids Res. 19(3): 585-90.

Piatak et al. (1993) High levels of HIV-1 in plasma during all stages of infection determined by competitive PCR. Science. 259: 1749-1754.

Pieles et al. (1989) Psoralen covalently linked to oligodeoxyribonucleotides: synthesis, sequence specific recognition of DNA and photo-cross-linking to pyrimidine residues of DNA. Nucleic Acids Res. 17(1): 285-99.

Pillai. (1980) Photoremovable protecting groups in organic synthesis. Synthesis. 1-26.

Polymerase from NEB printed information from New England BioLabs webpage (3 total pages), retrieved on Jul. 26, 2007 at http://www.neb.com/nebecomm/tech_reference/polymerases/polymerase_from_neb.asp.

Protein immobilization: fundamentals and applications, Richard F. Taylor, ed. (M. Dekker, New York, 1991).

Pruckler et al. (1995) Comparison of Legionella pneumophila isolates by arbitrarily primed PCR and pulsed-field gel electrophoresis: analysis from seven epidemic investigations. J Clin Microbiol. 33(11): 2872-5.

Rector et al. (2004) A sequence-independent strategy for detection and cloning of circular DNA virus genomes by using multiply primed rolling-circle amplification. J Virol. 78(10): 4993-8.

Robins et al. Fluorination at C5' of nucleosides. Synthesis of the new class of 5'- fluoro-5'-S-aryl (alkyl) thionucleosides from adenosine. Original Research Article pp. 5729-5732 1988.

Rodriguez et al. (1998) Large scale isolation of genes as DNA fragment lengths by continuous elution electrophoresis through an agarose matrix. Electrophoresis. 19(5): 646-52.

Rudbeck et al. (1998) Rapid, simple alkaline extraction of human genomic DNA from whole blood, buccal epithelial cells, semen and forensic stains for PCR. Biotechniques. 25(4): 588-90, 592.

Ruiz et al. (1998) Homology-dependent gene silencing in Paramecium. Mol Biol Cell. 9(4): 931-43.

Ryo et al. (2000) A modified serial analysis of gene expression that generates longer sequence tags by nonpalindromic cohesive linker ligation. Anal Biochem. 277(1): 160-162.

Salunkhe et al. (1992) Control of folding and binding of oligonucleotides by use of a nonnucleotide linker. J. Am. Chem. Soc. 114: 8768-8772.

Sambrook et al. Molecular Cloning: A Laboratory Manual. 2nd Edition. Cold Spring Harbor Laboratory Press, Cold Spring Harbor, N.Y., 1989—Chapters 5, 6.

Sasvari-Szekely et al. (2000) Rapid genotyping of factor V Leiden mutation using single-tube bidirectional allele-specific amplification and automated ultrathin-layer agarose gel electrophoresis. Electrophoresis. 21(4): 816-21.

Schaefer BC. (1995) Revolutions in rapid amplification of cDNA ends: new strategies for polymerase chain reaction cloning of full-length cDNA ends. Anal Biochem. 227(2): 255-73.

Schaum's Outline. (1997) Biochemistry. (2nd Edition) (PW Kuchel, GB Ralston, Eds).

Silber et al. (1972) Purification and properties of bacteriophage T4-induced RNA ligase. Proc Natl Acad Sci U S A. 69(10): 3009-13.

Sinha et al. (1988) The preparation and application of functionalised synthetic oligonucleotides: III. Use of H-phosphonate derivatives of protected amino-hexanol and mercapto-propanol or -hexanol. Nucleic Acids Res. 16(6): 2659-69.

Smart Notes from Cepheid. Sensitivity and Specificity Utilizing Amplifluor™ Primers. (4 pages).

Sørensen et al. (2000) Branched oligonucleotides containing bicyclic nucleotides as branching points and DNA or LNA as triplex forming branch. Bioorg Med Chem Lett. 10(16): 1853-1856.

Southern EM. (1975) Detection of specific sequences among DNA fragments separated by gel electrophoresis. J Mol Biol. 98(3): 503-17.

Sperling et al. (2002) Random sequencing of Paramecium somatic DNA. Eukaryot Cell. 1(3): 341-52.

Stefano et al. (1997) Rapid and sensitive detection of Chlamydia trachomatis using a ligatable binary RNA probe and Q beta replicase. Mol Cell Probes. 11(6): 407-26.

Stein et al. (1991) Mode of action of 5'-linked cholesteryl phosphorothioate oligodeoxynucleotides in inhibiting syncytia formation and infection by HIV-1 and HIV-2 in vitro. Biochemistry. 30(9): 2439-44.

Steller et al. (1995) Insulin-like growth factor II mediates epidermal growth factor-induced mitogenesis in cervical cancer cells. Proc Natl Acad Sci U S A. 92(26): 11970-4.

Stewart et al. (1998) A quantitative assay for assessing allelic proportions by iterative gap ligation.b Nucleic Acids Res. 26(4):961-6.

Takasugi et al. (1991) Sequence-specific photo-induced cross-linking of the two strands of double-helical DNA by a psoralen covalently linked to a triple helix-forming oligonucleotide. Proc Natl Acad Sci U S A. 88(13):5602-6.

Takeshita et al. (1987) Oligodeoxynucleotides containing synthetic abasic sites. Model substrates for DNA polymerases and apurinic/apyrimidinic endonucleases. J Biol Chem. 262(21): 10171-9.

Tanaka et al. (1989) Cleavage of a Nucleosidic Oxetane with Carbanions: Synthesis of a Highly Promising Candidate for Anti-HIV Agents—a Phosphonate Isotere of Azt 5'-Phosphate. Tetrahedron Lett. 30(19): 2567-2570.

Telenius et al. (1992) Degenerate oligonucleotide-primed PCR: general amplification of target DNA by a single degenerate primer. Genomics. 13(3): 718-25.

Tenover et al. (1994) Comparison of traditional and molecular methods of typing isolates of Staphylococcus aureus. J. Clin. Microbiol. 32(2): 407-15.

Tessier et al. (1996) Ligation of single-stranded oligodeoxyribonucleotides by T4 RNA ligase. Anal Biochem. 158(1): 171-8.

Theillet C. (1998) Full speed ahead for tumor screening. Nat Med. 4(7): 767-8.

Thomas et al. (1999) Amplification of padlock probes for DNA diagnostics by cascade rolling circle amplification or the polymerase chain reaction. Arch Pathol Lab Med. 123(12): 1170-6.

Tobe et al. (1996) Single-well genotyping of diallelic sequence variations by a two-color ELISA-based oligonucleotide ligation assay. Nucleic Acids Res. 24(19): 3728-32.

Troutt et al. (1992) Ligation-anchored PCR: a simple amplification technique with single-sided specificity. Proc Natl Acad Sci U S A. 89(20):9823-5.

Tuma et al. (1999) Characterization of SYBR Gold nucleic acid gel stain: a dye optimized for use with 300-nm ultraviolet transilluminators. Anal Biochem. 268(2): 278-288.

Séequin U. (1974) Nucleosides and Nucleotides. Part 7. Four dithymidine monophosphates with different anomeric configurations, their synthesis and behaviour towards phosphodiesterases. Helvetica Chimica Acta. 57: 68-81.

Välimaa et al. (1998) Detection of HLA-B27 alleles by group-specific amplification and time-resolved fluorometry. J Immunol Methods. 219(1-2): 131-137.

Välimaa et al. (1998) Detection of HLA-B27 alleles by group-specific amplification and time-resolved fluorometry. J Immunol Methods. 219(1-2): 131-7.

Van Gelder et al. (1990) Amplified RNA synthesized from limited quantities of heterogeneous cDNA. Proc Natl Acad Sci USA.; 87(5): 1663-1667.

Walder et al. (1993) Use of PCR primers containing a 3'-terminal ribose residue to prevent cross-contamination of amplified sequences. Nucleic Acids Res. 21(18): 4339-43.

Walker et al. (1994) Multiplex strand displacement amplification (SDA) and detection of DNA sequences from Mycobacterium tuberculosis and other mycobacteria. Nucleic Acids Res. 22(13):2670-7.

Wang et al. (1989) Quantitation of mRNA by the polymerase chain reaction. Proc Natl Acad Sci U S A. 86(24): 9717-21.

Wang et al. (1998) Oligoribonucleotide circularization by 'template-mediated' ligation with T4 RNA ligase: synthesis of circular hammerhead ribozymes. Nucleic Acids Res. 26(10): 2502-4.

Warnecke et al. (1997) Detection and measurement of PCR bias in quantitative methylation analysis of bisulphite-treated DNA. Nucleic Acids Res. 25(21): 4422-26.

Wells et al. (1999) Detailed chromosomal and molecular genetic analysis of single cells by whole genome amplification and comparative genomic hybridisation. Nucleic Acids Res. 27(4): 1214-1218.

Wells et al. (2000) Comprehensive chromosomal analysis of human preimplantation embryos using whole genome amplification and single cell comparative genomic hybridization. Mol Hum Reprod. 6(11): 1055-62.

Wharam et al. (2001) Specific detection of DNA and RNA targets using a novel isothermal nucleic acid amplification assay based on the formation of a three-way junction structure. Nucleic Acids Res. 29(11):E54: 1-8.

Whiting et al. (1994) Strand displacement synthesis capability of *Moloney murine leukemia virus* reverse transcriptase. J. Virol. 68(8): 4747-58.

Wiegant et al. (1992) High-resolution in situ hybridization using DNA halo preparations. Hum Mol Genet. 1(8): 587-91.

Wiley, et al. (1987) Current Protocols in Molecular Biology. vol. 1 (Ausubel et al. (Eds). Unit 1.6—Minipreps of Plasmid DNA.

Will et al. (1991) The synthesis of oligonucleotides that contain 2,4-dinitrophenyl reporter groups. Carbohydr Res. 216: 315-22.

Wiltshire et al. (2000) Detection of multiple allergen-specific IgEs on microarrays by immunoassay with rolling circle amplification. Clin Chem. 46(12): 1990-3.

Yates et al. (2001) Quantitative detection of hepatitis B virus DNA by real-time nucleic acid sequence-based amplification with molecular beacon detection. J Clin Microbiol. 39(10): 3656-65.

Yunis et al. (1978) The characterization of high-resolution G-banded chromosomes of man. Chromosoma. 67(4): 293-307.

Zhang et al. (1996) Single-stranded DNA ligation by T4 RNA ligase for PCR cloning of 5'-noncoding fragments and coding sequence of a specific gene. Nucleic Acids Res. 24(5): 990-1.

Zhao et al. (1995) Assessment of stress gene mRNAs (HSP-27, 60 and 70) in obstructed rabbit urinary bladder using a semi-quantitative RT-PCR method. Mol Cell Biochem. (1): 1-7.

Zhenodarova et al. (1989) [Substrate specificity of T4 RNA-ligase. The effect of the nucleotide composition of substrates and the size of phosphate donor on the effectiveness of intermolecular ligation]. [Article in Russian]. Bioorg Khim. 15(4): 478-83.

Zirvi et al. (1999) Improved fidelity of thermostable ligases for detection of microsatellite repeat sequences using nucleoside analogs. Nucleic Acids Res. 27(24): e41.

Zirvi et al. (1999) Ligase-based detection of mononucleotide repeat sequences. Nucleic Acids Res. 27(24) :e40.

Zuckermann et al. (1987) Efficient methods for attachment of thiol specific probes to the 3'-ends of synthetic oligodeoxyribonucleotides. Nucleic Acids Res. 15(13): 5305-21.

Preliminary Amendment filed Mar. 31, 2003 for U.S. Appl. No. 10/404,944, filed on Mar. 31, 2003 (Alsmadi et al.).

Preliminary Amendment filed Jan. 13, 2003 for U.S. Appl. No. 10/341,287, filed on Jan. 13, 2003 (Kingsmore et al.).

Issue Notification issued Jan. 15, 2004 for U.S. Appl. No. 09/897,259, filed on Jul. 2, 2001 (Ward et al.).

Notice of Allowance issued Jul. 1, 2003 for U.S. Appl. No. 09/897,259, filed on Jul. 2, 2001 (Ward et al.).

Response after Non-Final Rejection filed Apr. 11, 2003 for U.S. Appl. No. 09/897,259, filed on Jul. 2, 2001 (Ward et al.).

Non-Final Rejection issued Jan. 17, 2003 for U.S. Appl. No. 09/897,259, filed on Jul. 2, 2001 (Ward et al.).

Response to Election / Restriction filed Oct. 30, 2002 for U.S. Appl. No. 09/897,259, filed on Jul. 2, 2001 (Ward et al.).

Restriction Requirement issued Sep. 30, 2002 for U.S. Appl. No. 09/897,259, filed on Jul. 2, 2001 (Ward et al.).

Notice of Abandonment issued Nov. 14, 2007 for U.S. Appl. No. 09/910,383, filed on Jul. 20, 2001 (Nallur et al.).

Advisory Action issued May 1, 2007 for U.S. Appl. No. 09/910,383, filed on Jul. 20, 2001 (Nallur et al.).

Amendment/Argument after Notice of Appeal filed Apr. 18, 2007 for U.S. Appl. No. 09/910,383, filed on Jul. 20, 2001 (Nallur et al.).

Notice of Appeal issued Apr. 18, 2007 for U.S. Appl. No. 09/910,383, filed on Jul. 20, 2001 (Nallur et al.).

Examiner Interview Summary issued Apr. 9, 2007 for U.S. Appl. No. 09/910,383, filed on Jul. 20, 2001 (Nallur et al.).

Final Rejection issued Dec. 13, 2006 for U.S. Appl. No. 09/910,383, filed on Jul. 20, 2001 (Nallur et al.).

Response after Non-Final Action filed Sep. 29, 2006 for U.S. Appl. No. 09/910,383, filed on Jul. 20, 2001 (Nallur et al.).

Non-Final Rejection issued Jun. 15, 2006 for U.S. Appl. No. 09/910,383, filed on Jul. 20, 2001 (Nallur et al.).

Communication withdrawing Notice of Non-Compliant Amendment issued Apr. 7, 2006 for U.S. Appl. No. 09/910,383, filed on Jul. 20, 2001 (Nallur et al.).

Response after Non-Final Action filed Mar. 22, 2006 for U.S. Appl. No. 09/910,383, filed on Jul. 20, 2001 (Nallur et al.).

Advisory Action issued Dec. 13, 2005 for U.S. Appl. No. 09/910,383, filed on Jul. 20, 2001 (Nallur et al.).

Amendment after Final Rejection filed Nov. 23, 2005 for U.S. Appl. No. 09/910,383, filed on Jul. 20, 2001 (Nallur et al.).

Examiner Interview Summary Record issued Oct. 12, 2005 for U.S. Appl. No. 09/910,383, filed on Jul. 20, 2001 (Nallur et al.).

Advisory Action issued Sep. 14, 2005 for U.S. Appl. No. 09/910,383, filed on Jul. 20, 2001 (Nallur et al.).

Amendment after Final Rejection filed Aug. 26, 2005 for U.S. Appl. No. 09/910,383, filed on Jul. 20, 2001 (Nallur et al.).

Final Rejection issued May 23, 2005 for U.S. Appl. No. 09/910,383, filed on Jul. 20, 2001 (Nallur et al.).

Response after Non-Final Action filed Mar. 10, 2005 for U.S. Appl. No. 09/910,383, filed on Jul. 20, 2001 (Nallur et al.).

Non-Final Rejection issued Jan. 27, 2005 for U.S. Appl. No. 09/910,383, filed on Jul. 20, 2001 (Nallur et al.).

Response after Non-Final Action filed Nov. 19, 2004 for U.S. Appl. No. 09/910,383, filed on Jul. 20, 2001 (Nallur et al.).

Non-Final Rejection issued Jun. 23, 2004 for U.S. Appl. No. 09/910,383, filed on Jul. 20, 2001 (Nallur et al.).

Notice of Abandonment issued May 25, 2010 for U.S. Appl. No. 11/871,707, filed on Oct. 12, 2007 (Bornarth et al.).

Final Rejection issued Oct. 29, 2009 for U.S. Appl. No. 11/871,707, filed on Oct. 12, 2007 (Bornarth et al.).

Response after Non-Final Rejection filed Jun. 22, 2009 for U.S. Appl. No. 11/871,707, filed on Oct. 12, 2007 (Bornarth et al.).

Non-Final Rejection issued Jan. 28, 2009 for U.S. Appl. No. 11/871,707, filed on Oct. 12, 2007 (Bornarth et al.).

Restriction Requirement issued Jun. 17, 1997 for U.S. Appl. No. 08/754,681, filed on Nov. 21, 1996 (Lizardi et al.).

Decision on Petition issued Jul. 3, 2003 for U.S. Appl. No. 10/413,041, filed on Apr. 10, 2003 (Lizard et al.).

Petition to Correct Filing Date filed May 8, 2003 for U.S. Appl. No. 10/413,041, filed on Apr. 10, 2003 (Lizard et al.).

Preliminary Amendment filed Apr. 10, 2003 for U.S. Appl. No. 10/413,041, filed on Apr. 10, 2003 (Lizardi et al.).

Issue Notification issued Jun. 10, 2009 for U.S. Appl. No. 10/072,666, filed on Feb. 8, 2002 (Kumar et al.).

Preliminary Amendment filed Aug. 13, 2004 for U.S. Appl. No. 10/917,580, filed on Aug. 13, 2004 (Hafner et al.).

Preliminary Amendment filed Aug. 10, 2005 for U.S. Appl. No. 11/201,339, filed on Aug. 10, 2005 (Kumar et al.).

Response to Final Rejection filed May 26, 2010 for U.S. Appl. No. 10/327,602, filed on Dec. 20, 2002 (Lasken).

Notice of Appeal issued Apr. 27, 2010 for U.S. Appl. No. 10/327,602, filed on Dec. 20, 2002 (Lasken).

Interview Summary issued Dec. 24, 2009 for U.S. Appl. No. 10/327,602, filed on Dec. 20, 2002 (Lasken).

Supplemental Non-Final Rejection issued Oct. 27, 2009 for U.S. Appl. No. 10/327,602, filed on Dec. 20, 2002 (Lasken).

Non-Final Rejection issued Oct. 15, 2009 for U.S. Appl. No. 10/327,602, filed on Dec. 20, 2002 (Lasken).

Amendment and Response to Final Office Action filed Sep. 10, 2009 for U.S. Appl. No. 10/327,602, filed on Dec. 20, 2002 (Lasken).

Final Rejection issued Jun. 10, 2009 for U.S. Appl. No. 10/327,602, filed on Dec. 20, 2002 (Lasken).
Amendment and Response filed Mar. 31, 2009 for U.S. Appl. No. 10/327,602, filed on Dec. 20, 2002 (Lasken).
Notice of Abandonment issued Jun. 5, 2009 for U.S. Appl. No. 10/454,946, filed on Jun. 4, 2003 (Feaver et al.).
Examiner Interview Summary issued Aug. 8, 2008 for U.S. Appl. No. 10/454,946, filed on Jun. 4, 2003 (Feaver et al.).
Notice of Allowance issued Apr. 1, 2011 for U.S. Appl. No. 10/456,056, filed on Jun. 6, 2003 (Kumar et al.).
Notice of Allowance issued Jan. 25, 2011 for U.S. Appl. No. 10/456,056, filed on Jun. 6, 2003 (Kumar et al.).
Response after Non-Final Action filed Dec. 13, 2010 for U.S. Appl. No. 10/456,056, filed on Jun. 6, 2003 (Kumar et al.).
Notice of Non-Compliant Amendment issued Dec. 7, 2010 for U.S. Appl. No. 10/456,056, filed on Jun. 6, 2003 (Kumar et al.).
Response to Final Rejection filed Nov. 23, 2010 for U.S. Appl. No. 10/456,056, filed on Jun. 6, 2003 (Kumar et al.).
Non-Final Rejection issued Jun. 24, 2010 for U.S. Appl. No. 10/456,056, filed on Jun. 6, 2003 (Kumar et al.).
Response after Final Rejection filed Feb. 4, 2010 for U.S. Appl. No. 10/456,056, filed on Jun. 6, 2003 (Kumar et al.).
Examiner Interview Summary issued Nov. 17, 2009 for U.S. Appl. No. 10/456,056, filed on Jun. 6, 2003 (Kumar et al.).
Final Rejection issued Aug. 4, 2009 for U.S. Appl. No. 10/456,056, filed on Jun. 6, 2003 (Kumar et al.).
Response to Final Rejection filed May 27, 2009 for U.S. Appl. No. 10/456,056, filed on Jun. 6, 2003 (Kumar et al.).
Final Rejection issued Feb. 12, 2009 for U.S. Appl. No. 10/456,056, filed on Jun. 6, 2003 (Kumar et al.).
Response after Non-Final Action filed Oct. 23, 2008 for U.S. Appl. No. 10/456,056, filed on Jun. 6, 2003 (Kumar et al.).
Non-Final Rejection issued Aug. 8, 2008 for U.S. Appl. No. 10/456,056, filed on Jun. 6, 2003 (Kumar et al.).
Response to Final Rejection filed Apr. 7, 2008 for U.S. Appl. No. 10/456,056, filed on Jun. 6, 2003 (Kumar et al.).
Response to Final Rejection filed Mar. 7, 2008 for U.S. Appl. No. 10/456,056, filed on Jun. 6, 2003 (Kumar et al.).
Notice of Appeal filed Sep. 6, 2007 for U.S. Appl. No. 10/456,056, filed on Jun. 6, 2003 (Kumar et al.).
Examiner Interview Summary issued Apr. 17, 2007 for U.S. Appl. No. 10/456,056, filed on Jun. 6, 2003 (Kumar et al.).
Final Rejection issued Mar. 6, 2007 for U.S. Appl. No. 10/456,056, filed on Jun. 6, 2003 (Kumar et al.).
Response after Non-Final Action filed Dec. 7, 2006 for U.S. Appl. No. 10/456,056, filed on Jun. 6, 2003 (Kumar et al.).
Non-Final Rejection issued Aug. 2, 2006 for U.S. Appl. No. 10/456,056, filed on Jun. 6, 2003 (Kumar et al.).
Response to Election / Restriction filed May 12, 2006 for U.S. Appl. No. 10/456,056, filed on Jun. 6, 2003 (Kumar et al.).
Requirement for Restriction / Election issued Feb. 23, 2006 for U.S. Appl. No. 10/456,056, filed on Jun. 6, 2003 (Kumar et al.).
Issue Notification issued Nov. 9, 2001 for U.S. Appl. No. 09/605,192, filed on Jun. 28, 2000 (Lasken et al.).
Response to 312 Amendment issued Aug. 17, 2001 for U.S. Appl. No. 09/605,192, filed on Jun. 28, 2000 (Lasken et al.).
Notice of Abandonment issued May 27, 2009 for U.S. Appl. No. 09/920,571, filed on Jul. 31, 2001 (Lasken et al.).
Response after Non-Final Action filed Oct. 15, 2003 for U.S. Appl. No. 09/920,571, filed on Jul. 31, 2001 (Lasken et al.).
Miscellaneous Communication issued Oct. 7, 2003 for U.S. Appl. No. 09/920,571, filed on Jul. 31, 2001 (Lasken et al.).
Response after Non-Final Action filed Jun. 12, 2003 for U.S. Appl. No. 09/920,571, filed on Jul. 31, 2001 (Lasken et al.).
Response after Non-Final Action filed Jun. 12, 2002 for U.S. Appl. No. 09/920,571, filed on Jul. 31, 2001 (Lasken et al.).
Preliminary Amendment filed Aug. 1, 2001 for U.S. Appl. No. 09/920,571, filed on Jul. 31, 2001 (Lasken et al.).
Request for Certificate of Correction filed Aug. 27, 2002 for U.S. Appl. No. 09/577,444, filed on May 24, 2000 (Kingsmore et al.).
Decision regarding Certificate of Correction issued Mar. 22, 2004 for U.S. Appl. No. 09/897,665, filed on Jul. 2, 2001 (Kingsmore et al.).

Request for Certificate of Correction filed Feb. 25, 2004 for U.S. Appl. No. 09/897,665, filed on Jul. 2, 2001 (Kingsmore et al.).
Preliminary Amendment filed Jul. 2, 2001 for U.S. Appl. No. 09/897,665, filed on Jul. 2, 2001 (Kingsmore et al.).
Preliminary Amendment filed Aug. 31, 2004 for U.S. Appl. No. 10/931,015, filed on Aug. 31, 2004 (Shao).
Non-Final Rejection issued Feb. 16, 2011 for U.S. Appl. No. 11/870,715, filed on Oct. 11, 2007 (Korfhage et al.).
Response after Final Rejection filed Nov. 30, 2009 for U.S. Appl. No. 11/870,715, filed on Oct. 11, 2007 (Korfhage et al.).
Final Rejection issued Oct. 16, 2009 for U.S. Appl. No. 11/870,715, filed on Oct. 11, 2007 (Korfhage et al.).
Response after Final Rejection filed Jul. 24, 2009 for U.S. Appl. No. 11/870,715, filed on Oct. 11, 2007 (Korfhage et al.).
Examiner Interview Summary issued Jul. 15, 2009 for U.S. Appl. No. 11/870,715, filed on Oct. 11, 2007 (Korfhage et al.).
Final Rejection issued May 13, 2009 for U.S. Appl. No. 11/870,715, filed on Oct. 11, 2007 (Korfhage et al.).
Response after Non-Final Action filed Feb. 9, 2009 for U.S. Appl. No. 11/870,715, filed on Oct. 11, 2007 (Korfhage et al.).
Non-Final Rejection issued Nov. 12, 2008 for U.S. Appl. No. 11/870,715, filed on Oct. 11, 2007 (Korfhage et al.).
Preliminary Amendment filed Aug. 11, 1998 for U.S. Appl. No. 09/132,553, filed on Aug. 11, 1998 (Lizardi).
Preliminary Amendment filed Aug. 23, 2000 for U.S. Appl. No. 09/644,723, filed on Aug. 23, 2000 (Lizardi).
Preliminary Amendment filed Aug. 11, 1998 for U.S. Appl. No. 09/132,552, filed on Aug. 11, 1998 (Lizardi).
Preliminary Amendment filed Jan. 2, 2002 for U.S. Appl. No. 10/038,718, filed on Jan. 2, 2002 (Lizardi).
Certificate of Correction issued Oct. 26, 2010 for U.S. Appl. No. 10/896,513, filed on Jul. 22, 2004 (Lizardi).
Issue Notification issued Oct. 28, 2009 for U.S. Appl. No. 10/896,513, filed on Jul. 22, 2004 (Lizardi).
Notice of Allowance issued Jul. 9, 2009 for U.S. Appl. No. 10/896,513, filed on Jul. 22, 2004 (Lizardi).
Amendment and Response filed Mar. 26, 2009 for U.S. Appl. No. 10/896,513, filed on Jul. 22, 2004 (Lizardi).
Interview Summary issued Mar. 12, 2009 for U.S. Appl. No. 10/896,513, filed on Jul. 22, 2004 (Lizardi).
Interview Summary issued Jun. 13, 2008 for U.S. Appl. No. 10/896,513, filed on Jul. 22, 2004 (Lizardi).
Preliminary Amendment filed Jan. 25, 2005 for U.S. Appl. No. 10/896,513, filed on Jul. 22, 2004 (Lizardi).
Office Communication issued May 3, 2000 for U.S. Appl. No. 08/946,732, filed on Oct. 8, 1997 (Lizardi).
Preliminary Amendment filed Sep. 17, 1999 for U.S. Appl. No. 09/397,915, filed on Sep. 17, 1999 (Lizardi).
Preliminary Amendment filed Jul. 23, 2001 for U.S. Appl. No. 09/911,226, filed on Jul. 23, 2001 (Lizardi).
Notice of Abandonment issued Oct. 28, 2009 for U.S. Appl. No. 10/700,018, filed on Nov. 3, 2003 (Lizardi).
Advisory Action issued Apr. 2, 2009 for U.S. Appl. No. 10/700,018, filed on Nov. 3, 2003 (Lizardi).
Notice of Appeal filed Mar. 13, 2009 for U.S. Appl. No. 10/700,018, filed on Nov. 3, 2003 (Lizardi).
Amendment after Final Rejection filed Jan. 27, 2009 for U.S. Appl. No. 10/700,018, filed on Nov. 3, 2003 (Lizardi).
Written Opinion issued Jun. 6, 2003 for PCT/US02/02601 filed on Jan. 30, 2002 (Applicant—Molecular Staging, Inc.).
Communication regarding Expiry of Time Limit for Notice of Opposition issued Mar. 26, 2009 for EP 1928481.9, which claims priority to PCT/US01/11947 filed on Apr. 12, 2001 (Applicant—Molecular Staging, Inc.).
Notice of Abandonment issued Jun. 7, 2007 for CA 2405456, which claims priority to PCT/US01/11947 filed on Apr. 12, 2001 (Applicant—Molecular Staging, Inc.).
Notice of Reinstatement issued Jan. 10, 2005 for CA 2405456, which claims priority to PCT/US01/11947 filed on Apr. 12, 2001 (Applicant—Molecular Staging, Inc.).
Notice of Abandonment issued Jun. 8, 2004 for CA 2405456, which claims priority to PCT/US01/11947 filed on Apr. 12, 2001 (Applicant—Molecular Staging, Inc.).

Voluntary Amendment filed Apr. 11, 2003 for CA 2405456, which claims priority to PCT/US01/11947 filed on Apr. 12, 2001 (Applicant—Molecular Staging, Inc.).
Notice of Abandonment issued Feb. 26, 2007 for AU 2001269944, which claims priority to PCT/US01/19657 filed on Jun. 20, 2001 (Applicant—Molecular Staging, Inc.).
Notice of Abandonment issued Aug. 15, 2007 for CA 2411838, which claims priority to PCT/US01/19657 filed on Jun. 20, 2001 (Applicant—Molecular Staging, Inc.).
Noting of Loss of Rights pursuant to Rule 112(1) EPC issued Sep. 13, 2010 for EP 1948505.1, which claims priority to PCT/US01/19657 filed on Jun. 20, 2001 (Applicant—Molecular Staging, Inc.).
Communication pursuant to Article 94(3) EPC issued Jan. 29, 2010 for EP 1948505.1, which claims priority to PCT/US01/19657 filed on Jun. 20, 2001 (Applicant—Molecular Staging, Inc.).
Response to Rule 70(2) EPC Communication filed Oct. 6, 2009 for EP 1948505.1, which claims priority to PCT/US01/19657 filed on Jun. 20, 2001 (Applicant—Molecular Staging, Inc.).
Supplementary European Search Report issued Jul. 27, 2009 for EP 1948505.1, which claims priority to PCT/US01/19657 filed on Jun. 20, 2001 (Applicant—Molecular Staging, Inc.).
Notice of Allowance issued Mar. 1, 2011 for JP 2002-503102, which claims priority to PCT/US01/19657 filed on Jun. 20, 2001 (Applicant—Molecular Staging, Inc.).
Argument and Amendment filed Mar. 19, 2010 for JP 2002-503102, which claims priority to PCT/US01/19657 filed on Jun. 20, 2001 (Applicant—Molecular Staging, Inc.).
Notice of Rejection issued Dec. 22, 2009 for JP 2002-503102, which claims priority to PCT/US01/19657 filed on Jun. 20, 2001 (Applicant—Molecular Staging, Inc.).
Written Opinion issued Jun. 26, 2002 for PCT/US01/19657 filed on Jun. 20, 2001 (Applicant—Molecular Staging, Inc.).
Communication pursuant to 45(3) issued Jul. 20, 2004 for AU 2001271722, which claims priority to PCT/US01/20933 filed on Jul. 2, 2001 (Applicant—Molecular Staging, Inc.).
Direction to Request Examination filed Nov. 6, 2003 for AU 2001271722, which claims priority to PCT/US01/20933 filed on Jul. 2, 2001 (Applicant—Molecular Staging, Inc.).
Notice of Abandonment issued Aug. 28, 2007 for CA 2411794, which claims priority to PCT/US01/20933 filed on Jul. 2, 2001 (Applicant—Molecular Staging, Inc.).
Notice of National Entry issued Jan. 16, 2003 for CA 2411794, which claims priority to PCT/US01/20933 filed on Jul. 2, 2001 (Applicant—Molecular Staging, Inc.).
Communication re: the Expiry of the Time Limit to File Opposition issued Aug. 6, 2008 for EP 1950759.9, which claims priority to PCT/US01/20933 filed on Jul. 2, 2001 (Applicant—Molecular Staging, Inc.).
Written Opinion issued Mar. 19, 2004 for PCT/US02/15045 filed on May 10, 2002 (Applicant—Molecular Staging, Inc.).
Communication pursuant to Article 114(2) EPC issued Oct. 23, 2009 for EP 2801776.2, which claims priority to PCT/US02/33244 filed on Oct. 15, 2002 (Applicant—Molecular Staging, Inc.).
Written Opinion issued Feb. 24, 2004 for PCT/US02/33244 filed on Oct. 15, 2002 (Applicant—Molecular Staging, Inc.).
Notice of National Processing Completion issued Apr. 20, 2001 for BE 96940601.6, which claims priority to PCT/US96/18812 filed on Nov. 21, 1996 (Applicant—Yale University).
Communication regarding Expiry of Opposition Time Period issued Jan. 15, 2002 for EP 862652, which claims priority to PCT/US96/18812 filed on Nov. 21, 1996 (Applicant—Yale University).
European Search Report issued Feb. 21, 2003 for EP 99969209.8, which claims prioity to PCT/AU99/01110 filed on Dec. 14, 1999 (Applicant—Molecular Staging, Inc.).
Reasons for Appeal filed Jun. 19, 2008 for JP 2000-588388, which claims prioity to PCT/AU99/01110 filed on Dec. 14, 1999 (Applicant—Molecular Staging, Inc.).
Amendment filed May 20, 2008 for JP 2000-588388, which claims prioity to PCT/AU99/01110 filed on Dec. 14, 1999 (Applicant—Molecular Staging, Inc.).
Argument against Final Rejection filed Apr. 8, 2008, which claims prioity to PCT/AU99/01110 for JP 2000-588388 filed on Dec. 14, 1999 (Applicant—Molecular Staging, Inc.).

Examination Report issued Jan. 8, 2008 for JP 2000-588388, which claims prioity to PCT/AU99/01110 filed on Dec. 14, 1999 (Applicant—Molecular Staging, Inc.).
Amendment filed Nov. 26, 2007 for JP 2000-588388, which claims prioity to PCT/AU99/01110 filed on Dec. 14, 1999 (Applicant—Molecular Staging, Inc.).
Written Amendment filed Dec. 15, 2004 for JP 2000-588388, which claims prioity to PCT/AU99/01110 filed on Dec. 14, 1999 (Applicant—Molecular Staging, Inc.).
International Preliminary Examination Report issued Oct. 4, 2000 for PCT/AU99/01110 filed on Dec. 14, 1999 (Diatech Pty. Ltd.).
Written Opinion issued Jun. 28, 2000 for PCT/AU99/01110 filed on Dec. 14, 1999 (Diatech Pty. Ltd.).
Communication re: Expiry of Time Period for Opposition issued Apr. 6, 2011 for EP 3796961.5, which claims priority to PCT/US03/39430 filed on Dec. 11, 2003 (Applicant—Qiagen GmbH).
Decision to Grant a European Patent issued May 7, 2010 for EP 3796961.5, which claims priority to PCT/US03/39430 filed on Dec. 11, 2003 (Applicant—Qiagen GmbH).
Response to Communication issued Apr. 3, 2010 for EP 3796961.5, which claims priority to PCT/US03/39430 filed on Dec. 11, 2003 (Applicant—Qiagen GmbH).
Amendment or Correction of the Text for Grant filed Mar. 4, 2010 for EP 3796961.5, which claims priority to PCT/US03/39430 filed on Dec. 11, 2003 (Applicant—Qiagen GmbH).
Response to Communication filed Dec. 10, 2009 for EP 3796961.5, which claims priority to PCT/US03/39430 filed on Dec. 11, 2003 (Applicant—Qiagen GmbH).
Communication under Rule 71(3) EPC issued Aug. 17, 2009 for EP 3796961.5, which claims priority to PCT/US03/39430 filed on Dec. 11, 2003 (Applicant—Qiagen GmbH).
Response to Communication filed Jul. 7, 2009 for EP 3796961.5, which claims priority to PCT/US03/39430 filed on Dec. 11, 2003 (Applicant—Qiagen GmbH).
Invitation pursuant to Article 94(3) and Rule 71(1) EPC issued Jun. 19, 2009 for EP 3796961.5, which claims priority to PCT/US03/39430 filed on Dec. 11, 2003 (Applicant—Qiagen GmbH).
Response to Communication filed Mar. 14, 2007 for EP 3796961.5, which claims priority to PCT/US03/39430 filed on Dec. 11, 2003 (Applicant—Qiagen GmbH).
Proceeding further with EP patent application pursuant to Article 96(1) and Rule 51(1) EPC issued Feb. 2, 2007 for EP 3796961.5, which claims priority to PCT/US03/39430 filed on Dec. 11, 2003 (Applicant—Qiagen GmbH).
Notice of Rejection issued Sep. 29, 2009 for JP 2004-565385, which claims priority to PCT/US03/39430 filed on Dec. 11, 2003 (Applicant—Qiagen GmbH).
Notice of Abandonment issued Feb. 13, 2008 for CA 2510587, which claims priority to PCT/US03/40364 filed on Dec. 19, 2003 (Applicant—Qiagen GmbH).
Reply to Rule 124(4) Communication filed Dec. 21, 2010 for EP 3799976, which claims priority to PCT/US03/40364 filed on Dec. 19, 2003 (Applicant—Qiagen GmbH).
Minutes of Oral Proceedings issued Oct. 18, 2010 for EP 3799976, which claims priority to PCT/US03/40364 filed on Dec. 19, 2003 (Applicant—Qiagen GmbH).
Brief Communication issued Sep. 10, 2010 for EP 3799976, which claims priority to PCT/US03/40364 filed on Dec. 19, 2003 (Applicant—Qiagen GmbH).
Requests including 1st-4th Auxiliary Requests filed Aug. 23, 2010 for EP 3799976, which claims priority to PCT/US03/40364 filed on Dec. 19, 2003 (Applicant—Qiagen GmbH).
Summons to Attend Oral Proceedings issued May 6, 2010 for EP 3799976, which claims priority to PCT/US03/40364 filed on Dec. 19, 2003 (Applicant—Qiagen GmbH).
Response to Art. 94(3) EPC Communication filed Aug. 13, 2009 for EP 3799976, which claims priority to PCT/US03/40364 filed on Dec. 19, 2003 (Applicant—Qiagen GmbH).
Art. 94(3) EPC Communication issued May 14, 2009 for EP 3799976, which claims priority to PCT/US03/40364 filed on Dec. 19, 2003 (Applicant—Qiagen GmbH).

Response to Art. 94(3) EPC Communication filed Jun. 2, 2008 for EP 3799976, which claims priority to PCT/US03/40364 filed on Dec. 19, 2003 (Applicant—Qiagen GmbH).
Art. 94(3) EPC Communication issued Apr. 18, 2008 for EP 3799976, which claims priority to PCT/US03/40364 filed on Dec. 19, 2003 (Applicant—Qiagen GmbH).
Response to Art. 96(2) EPC Communication filed Dec. 17, 2007 for EP 3799976, which claims priority to PCT/US03/40364 filed on Dec. 19, 2003 (Applicant—Qiagen GmbH).
Art. 96(2) EPC Communication issued Aug. 22, 2007 for EP 3799976, which claims priority to PCT/US03/40364 filed on Dec. 19, 2003 (Applicant—Qiagen GmbH).
Response to Art. 96(1) Communication filed Jun. 29, 2007 for EP 3799976, which claims priority to PCT/US03/40364 filed on Dec. 19, 2003 (Applicant—Qiagen GmbH).
Art. 96(1) EPC Communication issued May 7, 2007 for 3799976, which claims priority to PCT/US03/40364 filed on Dec. 19, 2003 (Applicant—Qiagen GmbH).
Supplementary EPO Search Report issued Apr. 18, 2007 for EP 3799976, which claims priority to PCT/US03/40364 filed on Dec. 19, 2003 (Applicant—Qiagen GmbH).
Claim Set filed Sep. 22, 2010 for EP 10178502, which claims priority to PCT/US03/40364 filed on Dec. 19, 2003 (Applicant—Qiagen GmbH).
Amendment and Response filed Jul. 21, 2010 for JP 2005510007, which claims priority to PCT/US03/40364 filed on Dec. 19, 2003 (Applicant—Qiagen GmbH).
Examination Report issued Mar. 23, 2010 for JP 2005510007, which claims priority to PCT/US03/40364 filed on Dec. 19, 2003 (Applicant—Qiagen GmbH).
Amendment and Response filed Feb. 26, 2010 for JP 2005510007, which claims priority to PCT/US03/40364 filed on Dec. 19, 2003 (Applicant—Qiagen GmbH).
Examination Report issued Nov. 4, 2009 for JP 2005510007, which claims priority to PCT/US03/40364 filed on Dec. 19, 2003 (Applicant—Qiagen GmbH).
Claim Set filed Feb. 26, 2010 for JP 2010042086, which claims priority to PCT/US03/40364 filed on Dec. 19, 2003 (Applicant—Qiagen GmbH).
International Search Report issued Apr. 4, 2005 for PCT/US03/40364 filed on Dec. 19, 2003 (Applicant—Qiagen GmbH).
Notification of Search Results issued May 5, 2004 for AU 2001268725, which claims priority to PCT/US01/20217 filed on Jun. 27, 2001 (Applicant—Qiagen GmbH).
Expiry of Time Limit in which to file Notice of Opposition issued Aug. 22, 2007 for EP 1946712.5, which claims priority to PCT/US01/20217 filed on Jun. 27, 2001 (Applicant—Molecular Staging, Inc.).
Brief Communication re: Amendment issued Aug. 31, 2006 for EP 1946712.5, which claims priority to PCT/US01/20217filed on Jun. 27, 2001 (Applicant—Molecular Staging, Inc.).
Written Opinion issued Oct. 23, 2003 for PCT/US01/20217 filed on Jun. 27, 2001 (Applicant—Molecular Staging, Inc.).
Acknowledgment of withdrawal of patent application issued Mar. 9, 2005 for EP 2705674.6, which claims priority to PCT/US02/00005 filed on Jan. 4, 2002 (Applicant—Molecular Staging, Inc.).
Acknowledgement of Withdrawal issued Oct. 6, 2003 for EP 980827, which claims priority to PCT/US00/32370 filed on Nov. 28, 2000 (Applicant—Molecular Staging, Inc.).
Withdrawal of Application issued Sep. 10, 2003 for EP 980827, which claims priority to PCT/US00/32370 filed on Nov. 28, 2000 (Applicant—Molecular Staging, Inc.).
Response to Art. 94(3) EPC Communication filed Jan. 4, 2011 for EP 7118804.9 filed on Oct. 18, 2007 (Applicant—Qiagen GmbH).
Art. 94(3) EPC Communication issued Aug. 26, 2010 for EP 7118804.9 filed on Oct. 18, 2007 (Applicant—Qiagen GmbH).
Response to Art. 94(3) EPC Communication filed Sep. 29, 2008 for EP 7118804.9 filed on Oct. 18, 2007 (Applicant—Qiagen GmbH).
Art. 94(3) EPC Communication issued Aug. 7, 2008 for EP 7118804.9 filed on Oct. 18, 2007 (Applicant—Qiagen GmbH).
Request for Examination filed Jul. 27, 2010 for JP 2007-276942 filed on Oct. 24, 2007(Applicant—Qiagen GmbH).
Voluntary Amendments filed Oct. 12, 2000 for CA 2308004, which claims priority to PCT/US98/21177 filed on Oct. 8, 1998 (Applicant—Yale University).
Communication regarding Expiry of Opposition Time Period issued Nov. 5, 2008 for EP 98952147.1, which claims priority to PCT/US98/21177 filed on Oct. 8, 1998 (Applicant—Yale University).
Brief Communication re: Request for Amendment of Application issued Nov. 2, 2007 for EP 98952147.1, which claims priority to PCT/US98/21177 filed on Oct. 8, 1998 (Applicant—Yale University).
Favorable Decision regarding Notice of Appeal issued Feb. 3, 2009 for JP 2000-515033, which claims priority to PCT/US98/21177 filed on Oct. 8, 1998 (Applicant—Yale University).
Amendment and Response to Official Action filed Dec. 22, 2008 for JP 2000-515033, which claims priority to PCT/US98/21177 filed on Oct. 8, 1998 (Applicant—Yale University).
Official Action issued Dec. 2, 2008 for JP 2000-515033, which claims priority to PCT/US98/21177 filed on Oct. 8, 1998 (Applicant—Yale University).
Argument to Written Communication filed Apr. 2, 1008 for JP2000-515033, which claims priority to PCT/US98/21177 filed on Oct. 8, 1998 (Applicant—Yale University).
Amendment and Response to Official Action filed Dec. 28, 2006 for JP 2000-515033, which claims priority to PCT/US98/21177 filed on Oct. 8, 1998 (Applicant—Yale University).
Response to Written Opinion issued Oct. 18, 1999 for PCT/US98/21177 filed on Oct. 8, 1998 (Applicant—Yale University).
Written Opinion issued Jul. 20, 1999 for PCT/US98/21177 filed on Oct. 8, 1998 (Applicant—Yale University).
Noting of Loss of Rights (69(1) EPC) issued Apr. 1, 2004 for EP 99935725.4, which claims priority to PCT/US99/16373 filed on Jul. 20, 1999 (Applicant—Yale University).
International Preliminary Examination Report issued Sep. 19, 2000 for PCT/US99/16373 filed on Jul. 20, 1999 (Applicant—Yale University).
Response to Written Opinion filed Aug. 18, 2000 for PCT/US99/16373 filed on Jul. 20, 1999 (Applicant —Yale University).
Written Opinion issued Jun. 20, 2000 for PCT/US99/16373 filed on Jul. 20, 1999 (Applicant—Yale University).

* cited by examiner

UNIVERSAL REAGENTS FOR ROLLING CIRCLE AMPLIFICATION AND METHODS OF USE

FIELD OF THE INVENTION

The disclosed invention is generally in the field of nucleic acid amplification and labeling and detection of analytes, and specifically in the area of labeling and detection of analytes using rolling circle amplification.

BACKGROUND OF THE INVENTION

Numerous nucleic acid amplification techniques have been devised, including strand displacement cascade amplification (SDCA)(referred to herein as exponential rolling circle amplification (ERCA)) and rolling circle amplification (RCA)(U.S. Pat. No. 5,854,033; PCT Application No. WO 97/19193; Lizardi et al., *Nature Genetics* 19(3):225-232 (1998)); multiple displacement amplification (MDA)(PCT Application WO 99/18241); strand displacement amplification (SDA)(Walker et al., Nucleic Acids Research 20:1691-1696 (1992), Walker et al., Proc. Natl. Acad. Sci. USA 89:392-396 (1992)); polymerase chain reaction (PCR) and other exponential amplification techniques involving thermal cycling, self-sustained sequence replication (3SR), nucleic acid sequence based amplification (NASBA), and amplification with Qβ replicase (Birkenmeyer and Mushahwar, *J. Virological Methods* 35:117-126 (1991); Landegren, *Trends Genetics* 9:199-202 (1993)); and various linear amplification techniques involving thermal cycling such as cycle sequencing (Craxton et al., *Methods Companion Methods in Enzymology* 3:20-26 (1991)).

Rolling Circle Amplification (RCA) driven by DNA polymerase can replicate circular oligonucleotide probes with either linear or geometric kinetics under isothermal conditions (Lizardi et al., *Nature Genet.* 19: 225-232 (1998); U.S. Pat. Nos. 5,854,033 and 6,143,495; PCT Application No. WO 97/19193). If a single primer is used, RCA generates in a few minutes a linear chain of hundreds or thousands of tandemly-linked DNA copies of a target that is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (PCT Application No. WO 97/19193), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998). Ligation-mediated Rolling Circle Amplification (LM-RCA) involves circularization of a probe molecule hybridized to a target sequence and subsequent rolling circle amplification of the circular probe (U.S. Pat. Nos. 5,854,033 and 6,143,495; PCT Application No. WO 97/19193). Very high yields of amplified products can be obtained with exponential rolling circle amplification (U.S. Pat. Nos. 5,854,033 and 6,143,495; PCT Application No. WO 97/19193) and multiply-primed rolling circle amplification (Dean et al., Genome Research 11:1095-1099 (2001)).

BRIEF SUMMARY OF THE INVENTION

Disclosed are compositions and methods useful for labeling and detection of analytes. The compositions generally are associations of three components: reporter binding agents, amplification target circles, and DNA polymerase. The compositions are assembled prior to their use in a rolling circle amplification reaction and can be stored and transported prior to use without substantial loss of activity. The compositions can reduce the difficulty of performing rolling circle amplification reactions by reducing the number of components that must be mixed at the time of the reaction and can improve consistency between rolling circle amplification reactions through the use of the same reagent composition in the reactions. The reporter binding agents generally are composed of a specific binding molecule and a rolling circle replication primer. The specific binding molecule can be specific for a target molecule (an analyte to be labeled or detected, for example). The rolling circle replication primer has sequence complementary to the amplification target circle. The DNA polymerase can interact with the rolling circle replication primer and amplification target circle. For use as a general reagent, the specific binding molecule is not bound to the target molecule until the composition is used in an assay. Similarly, the amplification target circle generally will not be amplified prior to use of the composition in an assay.

The compositions can be used to label and/or detect an analyte of interest. The compositions can be associated with an analyte (via the specific binding molecule) and the amplification target circle can be amplified by rolling circle amplification (primed by the rolling circle replication primer and catalyzed by the DNA polymerase) to produce amplification products. Rolling circle amplification can produce a large amount of amplification products in a short time, thus providing a large and easily detected signal from a single amplification target circle.

Some forms of the disclosed compositions can be used as universal reagents of rolling circle amplification. For this purpose, the compositions can have specific binding molecules that can interact with particular moieties or molecules that are present on, or are used to label any target molecule of interest. For example, the specific binding molecule in the reagent composition can be streptavidin or another biotin-specific molecule (such as an anti-biotin antibody). Any target molecule labeled with biotin can then be associated with the reagent composition and labeled and/or detected via rolling circle amplification mediated by the composition. This reagent composition can be used with any biotinylated target molecule. Similarly, use of an antibody specific to a class of antibodies (for example, and anti-mouse antibody) as the specific binding molecule in reagent compositions. Such reagent compositions can be used to label and detect a class of antibodies in an assay. For example, the reagent composition can be used to label and detect all mouse antibodies bound to antigen in immunoassays regardless of the specificity of the individual mouse antibodies. This is analogous to the use of antibodies specific to a class of antibodies in sandwich immunoassays. The disclosed reagents compositions provide greater signal amplification and tighter localization of the signal than in traditional immunoassays.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
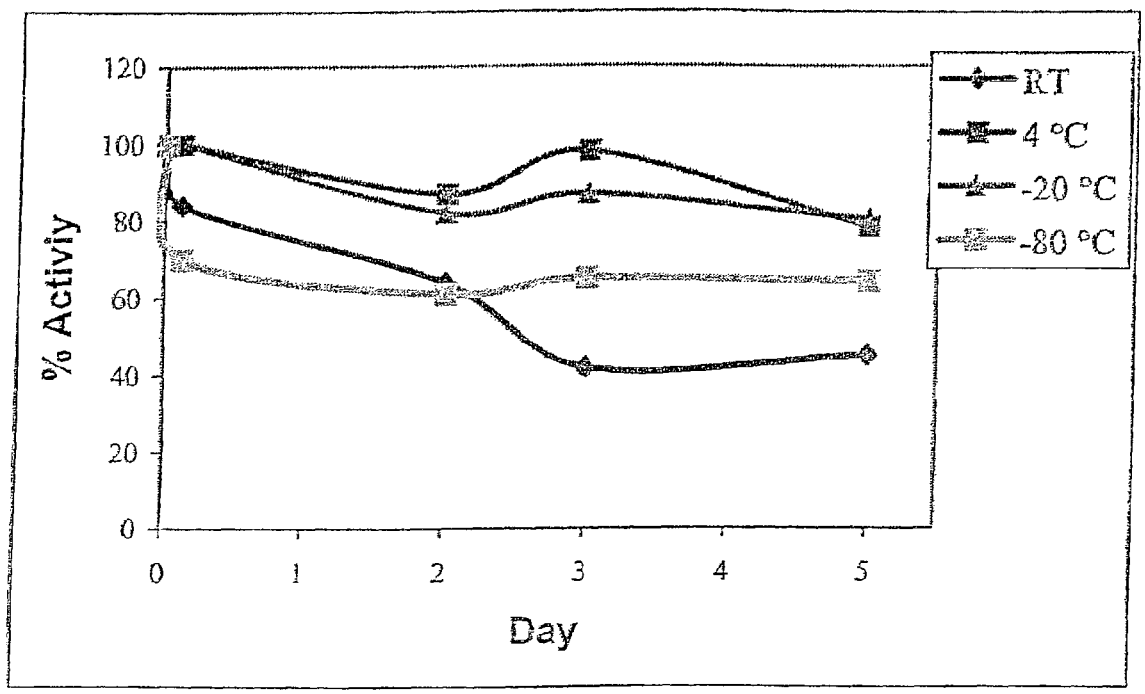
FIG. 1 is a graph of time of storage (in days) of RCA reagent versus percent activity of the RCA reagent in a rolling circle amplification reaction.

The disclosed method and compositions can be understood more readily by reference to the following detailed description of particular embodiments and the Example included therein and to the Figures and their previous and following description.

Disclosed are compositions and methods useful for labeling and detection of analytes. The compositions generally are associations of three components: reporter binding agents, amplification target circles, and DNA polymerase. These compositions, which can be referred to as reagent compositions, provide the main components for a rolling circle amplification reaction in a pre-assembled association, thus providing a convenient reagent for carrying out rolling circle amplification. The reporter binding agent is used to associate the reagent composition with a target molecule. This association allows amplified signal (the result of rolling circle amplification) to be associated with and/or correlated with the presence of the target molecule. Reporter binding agents generally are composed of a specific binding molecule and a rolling circle replication primer. The specific binding molecule and rolling circle replication primer are coupled, linked or otherwise associated with each other. The specific binding molecule can interact specifically with a target molecule (such as an analyte or label) and thus mediates association of the reagent composition to the target molecule.

The rolling circle replication primer is used to prime rolling circle replication of the amplification target circle. For this purpose, the rolling circle replication primer has sequence complementary to the amplification target circle. This complementarity also allows the rolling circle replication primer and amplification target circle to associate together through hybridization in the reagent composition. DNA polymerase catalyzes replication of the amplification target circle to form amplification products of rolling circle amplification. The DNA polymerase can interact with the rolling circle replication primer and amplification target circle. In the reagent composition, this interaction can take the form of a complex of polymerase, primer and template ready for replication. The interactions of the three components in the reagent compositions provide increased stability over the components individually. Thus, the reagent compositions can be assembled prior to their use in a rolling circle amplification reaction and can be stored and transported prior to use without substantial loss of activity. The compositions can reduce the difficultly of performing rolling circle amplification reactions by reducing the number of components that must be mixed at the time of the reaction and can improve consistency between rolling circle amplification reactions through the use of the same reagent composition in the reactions.

For use as a general reagent, the reagent composition can be produced and stored as a complex of the three components and in the absence of other components and reagents that may be used in an amplification reaction. For example, the specific binding molecule in the reagent composition will not be bound to the target molecule until the composition is used in an assay. The composition generally will not include any nucleotides needed for replication. The amplification target circle generally will not be amplified prior to use of the composition in an assay. However, in some forms, the reagent composition can include other components and reagents for amplification such as nucleotides, additional primers, detection probes, and labels.

In use, the reagent compositions generally will be associated with a target molecule, via the specific binding molecule of the reporter binding agent, and a signal can be generated by performing rolling circle amplification of the amplification target circle. The DNA polymerase catalyzes replication primed by the rolling circle replication primer of the reporter binding agent. Rolling circle replication refers to replication of a circular nucleic acid template (referred to as an amplification target circle; ATC) to form a long strand (referred to as tandem sequence DNA; TS-DNA) with tandem repeats of the sequence complementary to the circular template. Rolling circle amplification (RCA) refers to nucleic acid amplification reactions involving rolling circle replication and, optionally, additional types and levels of nucleic acid replication and amplification. Rolling circle amplification can produce a large amount of amplification products in a short time, thus providing a large and easily detected signal from a single amplification target circle. Rolling circle amplification refers both to rolling circle replication and to processes involving both rolling circle replication and additional forms of replication and amplification (such as replication of tandem sequence DNA). The disclosed reagent compositions are ideally suited for rolling circle replication and amplification because they include the key components of rolling circle replication: primer (the rolling circle replication primer), template (the amplification target circle), and DNA polymerase.

The disclosed compositions can be used to label and/or detect an analyte of interest. For use in labeling and/or detecting analytes, the specific binding molecule of the reagent composition can be a molecule or moiety that can interact specifically with the analyte. Antibodies are a form of specific binding molecule that can provide specific binding to a wide variety of possible analytes. In this use, the reagent composition provides a target-specific, amplifiable label for any analyte of interest. The amplified label will be tandem sequence DNA and other amplification products. The analyte can be detected by detecting the amplification products.

Some forms of the disclosed compositions can be used as universal reagents for rolling circle amplification. For this purpose, the compositions can have specific binding molecules that can interact with particular moieties or molecules that are present on, or are used to label, any molecule of interest. Any molecules to be detected can be labeled with a target molecule for which the specific binding molecule in the reagent composition is specific. In this way, any molecule of interest can be associated with the reagent composition and labeled with amplification products of rolling circle amplification. For example, molecules of interest can be labeled with biotin. By using a reagent composition where the specific binding molecule is streptavidin or another biotin-specific molecule (such as an anti-biotin antibody), the reagent composition can be associated with any of the labeled molecules. This reagent composition can be used with any biotinylated target molecule. Any other suitable molecule or moiety can be in a similar manner in to biotin as a label to mediate association of reagent compositions with molecules of interest.

The disclosed compositions can also be used as a universal reagent in immunoassays. In some immunoassays, an analyte-specific antibody can be bound to the analyte and a second antibody, specific for the type of antibody used as the analyte-specific antibody, can be used as the specific binding molecule in a reagent composition to bind the reagent composition to the analyte-specific antibody. For example, if the antigen-specific antibody is a mouse antibody, then the second antibody (that is, the specific binding molecule in the reagent composition) can be an anti-mouse antibody. Once the reagent composition is associated with the antigen-specific antibody, the amplification target circle can be amplified to produce amplification product that can be detected. An anti-mouse reagent composition such as this can be used to label and detect any analyte-or antigen-specific mouse antibody. Generalizing, any, for example, source-, class-, allotype-, or isotype-specific antibody can be used as the specific binding molecule in a reagent composition to label and detect all analyte-and antigen-specific antibodies of the relevant source, class, allotype, or isotype. This is analogous to the use of antibodies specific to a class of antibodies in sandwich immunoassays. The disclosed reagents compositions provide greater signal amplification and tighter localization of the signal than in traditional immunoassays.

The disclosed compositions and methods can be used for real-time detection of rolling circle amplification products. Real-time detection is detection that takes place during the amplification reaction or operation. Generally, such detection can be accomplished by detecting amplification product at one or more discrete times during amplification, continuously during all or one or more portions of the amplification, or a combination of discrete times and continuous detection. Real-time detection can be aided by the use of labels or moieties that embody or produce a detectable signal that can be detected without disrupting the amplification reaction or operation. Fluorescent labels are an example of useful labels for real-time detection. A particularly useful means of obtaining real-time detection is the use of fluorescent change probes and/or primers in the amplification operation. With suitably designed fluorescent change probes and primers, fluorescent signals can be generated as amplification proceeds. In most such cases, the fluorescent signals will be in proportion to the amount of amplification product and/or amount of target sequence or target molecule. Real-time detection of rolling circle amplification products is described in U.S. application Ser. No. 10/325,665, which is hereby incorporated by reference.

The disclosed reagent compositions can be amplified using multiply-primed rolling circle amplification (MPRCA). Rolling circle replication can be primed at one or more sites on the amplification target circle. Multiply-primed RCA refers to RCA where replication is primed at a plurality of sites on the circular template. In this form of the method, the rolling circle replication primer in the reagent composition primes at one of the sites and one or more additional primers prime at other sites on the amplification target circle. The additional primers can be separate from the reagent composition. Multiply-primed RCA increases the sensitivity of amplification over singly-primed rolling circle amplification. Multiply-primed RCA is described in U.S. Pat. No. 6,323,009 and U.S. application Ser. No. 10/335,573, which are hereby incorporated by reference.

Any or all of the primers used in the disclosed compositions and methods, such as the rolling circle replication primer of the reporter binding agent, can be resistant to degradation by exonuclease activity that may be present in the reaction. This has the advantage of permitting the primers to persist in reactions that contain an exonuclease activity and that may be carried out for long incubation periods. The persistence of primers allows new priming events to occur for the entire incubation time of the reaction, which is one of the hallmarks of exponential RCA (ERCA) and has the advantage of increasing the yield of amplified DNA.

Fluorescent change probes and primers, which are useful for obtaining real-time detection of amplification, refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes. Change in fluorescence wavelength or intensity from fluorescent change probes and primers generally involves energy transfer and/or quenching. Fluorescent change probes and primers can be classified according to their structure and/or function. Fluorescent change probes include, for example, hairpin quenched probes, cleavage quenched probes, cleavage activated probes, and fluorescent activated probes.

Amplification target circles can be, for example, designed and prefabricated for use in the disclosed method or can be produced from nucleic acid sources and samples of interest. For example, in some forms of the disclosed method, amplification target circles are designed and synthesized to have specific features making them useful for particular forms of the disclosed method. Such features are described in detail elsewhere herein. Amplification target circles can be circularized open circle probes. Such circularization is usefully accomplished via target-mediated ligation of the ends of the open circle probe.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a rolling circle replication primer is disclosed and discussed and a number of modifications that can be made to a number of molecules including the rolling circle replication primer are discussed, each and every combination and permutation of the rolling circle replication primer and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Reagent Compositions

Reagent compositions generally are associations of three components: reporter binding agents, amplification target circles, and DNA polymerase. These compositions provide the main components for a rolling circle amplification reaction in a pre-assembled association, thus providing a convenient reagent for carrying out rolling circle amplification. The interactions of the three components in the reagent compositions provide increased stability over the components individually. Reagent compositions can be assembled prior to their use in a rolling circle amplification reaction and can be stored and transported prior to use without substantial loss of activity. The compositions can reduce the difficulty of performing rolling circle amplification reactions by reducing the number of components that must be mixed at the time of the reaction and can improve consistency between rolling circle amplification reactions through the use of the same reagent composition in the reactions.

A reagent composition can be made up of one or more reporter binding agents, one or more amplification target circles, and one or more DNA polymerases. Multiple reporter binding agents can be used to increase the binding capacity of the reagent composition for the target molecule (where the multiple reporter binding agents are all specific for the same target molecule), to provide specificity for multiple target molecules in the same reagent composition (where the multiple reporter binding agents are specific for different target molecules), or both. Multiple reporter binding agents can be included in a reagent composition by, for example, coupling the reporter binding agents together or including a component that allows the reporter binding agents to associate together. For this purpose, it is preferred that the reporter binding agents be coupled or associated together via linkers.

Multiple amplification target circles can be used to increase the amplification yield for the reagent composition, to provide amplification of multiple different sequences (where different amplification target circles are used), or both. Amplification yield can be increased with the use of both multiple amplification target circles whether the amplification target circles are the same or not. Multiple amplification target circles can be included in a reagent composition by including multiple reporter binding agents in the reagent composition, by including multiple rolling circle replication primers on the reporter binding agent, or both. An amplification target circle can anneal to each rolling circle replication primer. A useful form of reagent composition for this purpose can be made up of one or more reporter binding agents each with three rolling circle replication primers.

Multiple DNA polymerases can be used to increase the yield of amplification. Generally, the number of DNA polymerases in a reagent composition will be determined by the number or amplification target circles and rolling circle replication primers in the reagent composition. That is, a DNA polymerase can bind to each rolling circle replication primer/amplification target circle hybrid.

For use as a general reagent, the reagent composition can be produced and stored as a complex of the three components and in the absence of other components and reagents that may be used in an amplification reaction. For example, reagent compositions can be made and stored where the specific binding molecule in the reagent composition is not bound to the target molecule (such binding is accomplished when the reagent composition is used in an assay). The composition generally need not, but may, include any nucleotides needed for replication. The amplification target circle generally will not be amplified prior to use of the composition in an assay. However, in some forms, the reagent composition can include other components and reagents for amplification such as nucleotides, additional primers, detection probes, and labels.

One useful form of reagent composition includes one or more free rolling circle replication primers. Such free rolling circle replication primers will have sequence complementary to the amplification target circle and can anneal to the amplification target circle in the reagent composition. The free rolling circle replication primers preferably are complementary to sequence in the amplification target circle that does not overlap with the sequence complementary to the rolling circle replication primer of the reporter binding agent. Free rolling circle replication primers can facilitate multiply-primed rolling circle amplification from the reagent composition.

One form of reagent composition, referred to as an RCA reagent, is a reagent composition where the specific binding molecule of the reporter binding agent is not bound to target molecule and where the reagent composition does not include tandem sequence DNA. Thus, an RCA reagent is a reagent composition before it is used to bind a target molecule and before the amplification target circle is amplified to produce tandem sequence DNA. In other words, an RCA reagent is a reagent composition before it is used in an assay or reaction. A preferred form of RCA reagent is formed only of reporter binding agents, amplification target circles, and DNA polymerase.

Reagent compositions can be made by mixing together or bringing into contact the three basic components. The reporter binding agents, amplification target circles, and DNA polymerase have affinity and will form associations together. The rolling circle replication primer of the reporter binding agent has sequence complementary to the amplification target circle and so can hybridize to the amplification target circle. The DNA polymerase has affinity for DNA, and in particular for the transition between double-stranded and single-stranded DNA. The annealed rolling circle replication primer and amplification target circle will form such a transition. The three components can form an association that is essentially a pre-initiation complex for DNA polymerization. The association of the three components in a reagent composition creates a stable and consistent mixture of the components resulting in more consistent amplification results form assay to assay.

Reagent compositions can be made by, for example, annealing an amplification target circle to a rolling circle replication primer of a reporter binding agent and then incubating the reporter binding agent and amplification target circle with DNA polymerase. Annealing and incubation can be done simultaneously, but are preferably performed sequentially. Conditions for annealing generally can be chosen based on the length and nucleotide composition of the complementary portions of the amplification target circle and rolling circle replication primer using well-known principles and techniques. The stability of hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990). Useful conditions for annealing the amplification target circle and rolling circle replication primer are from about 50 mM to about 150 mM of a suitable salt. Preferred salts are salts that are compatible with the DNA polymerase. In some forms of the composition, the DNA polymerase can be incubated with the reporter binding agent and amplification target circle substantially in the absence of $Mg^{2+}$. Substantially in the absence of $Mg^{2+}$ refers to less than 10 μM $Mg^{2+}$. Useful temperatures for annealing depend on the length and composition of the complementary portions. Typical amplification target circles and rolling circle replication primers can be incubated at from about 35° C. to about 40° C. Amplification target circles and rolling circle replication primers can be annealed for any period of time suitable to allow a significant or substantial number of amplification target circles and rolling circle replication primers to hybridize. Typical annealing times can be from about 30 minutes to about 45 minutes, but annealing can be continued longer. There is no limit to the length of annealing time.

DNA polymerase can be incubated with reporter binding agents and amplification target circles under any suitable conditions. Generally this can be at a temperature at or below a temperature where either the DNA polymerase or rolling circle replication primer/amplification target circle hybrid would become unstable. Useful temperatures of incubation can be at or below the reaction temperature for the DNA polymerase. Typical incubation temperatures can be form about 25° C. to about 33° C. Typical incubation times can be from about 10 minutes to about 20 minutes. The proportions of components mixed and incubated to form reagent compositions generally can be the same proportions that the components will have in the composition. For example, if a reagent composition is made up of one reporter binding agent having three rolling circle replication primers, then the number of amplification target circles and DNA polymerase mixed with the reporter binding agent can be about three times the number of reporter binding agents. However, the components of reagent compositions need not be prepared using proportional concentrations of the components. Useful concentrations of reporter binding agents include about 50 nM or higher. Reporter binding agents can have any desired concentration in reagent compositions. For example, reagent compositions can have 5 nM, 10 nM, 15 nM, 20 nM, 25 nM, 30 nM, 35 nM, 40 nM, 42 nM, 44 nM, 46 nM, 48 nM, 50 nM, 52 nM, 54 nM, 56 nM, 58 nM, 60 nM, 62 nM, 64 nM, 66 nM, 68 nM, 70 nM, 75 nM, 80 nM, 85 nM, 90 nM, 95 nM, 100 nM, 105 nM, 110 nM, 115 nM, 120 nM, 125 nM, 130 nM, 135 nM, 140 nM, 145 nM, 150 nM, 160 nM, 170 nM, 180 nM, 190 nM, 200 nM, 210 nM, 220 nM, 230 nM, 240 nM, 250 nM, 260 nM, 280 nM, 300 nM, 320 nM, 340 nM, 360 nM, 380 nM, 400 nM, 450 nM, 500 nM, 550 nM, 600 nM, 650 nM, 700 nM, 750 nM, 800 nM, 850 nM, 900 nM, 950 nM, 1000 nM, 2 mM, 3 mM, 4 mM, 5 mM, or 10 mM concentration of reporter binding agent. Reagent compositions can have about 5 nM, about 10 nM, about 15 nM, about 20 nM, about 25 nM, about 30 nM, about 35 nM, about 40 nM, about 42 nM, about 44 nM, about 46 nM, about 48 nM, about 50 nM, about 52 nM, about 54 nM, about 56 nM, about 58 nM, about 60 nM, about 62 nM, about 64 nM, about 66 nM, about 68 nM, about 70 nM, about 75 nM, about 80 nM, about 85 nM, about 90 nM, about 95 nM, about 100 nM, about 105 nM, about 110 nM, about 115 nM, about 120 nM, about 125 nM, about 130 nM, about 135 nM, about 140 nM, about 145 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 280 nM, about 300 nM, about 320 nM, about 340 nM, about 360 nM, about 380 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1000 nM, about 2 mM, about 3 mM, about 4 mM, about 5 mM, or about 10 mM concentration of reporter binding agent. Reagent compositions can have 5 nM or higher, 10 nM or higher, 15 nM or higher, 20 nM or higher, 25 nM or higher, 30 nM or higher, 35 nM or higher, 40 nM or higher, 42 nM or higher, 44 nM or higher, 46 nM or higher, 48 nM or higher, 50 nM or higher, 52 nM or higher, 54 nM or higher, 56 nM or higher, 58 nM or higher, 60 nM or higher, 62 nM or higher, 64 nM or higher, 66 nM or higher, 68 nM or higher, 70 nM or higher, 75 nM or higher, 80 nM or higher, 85 nM or higher, 90 nM or higher, 95 nM or higher, 100 nM or higher, 105 nM or higher, 110 nM or higher, 115 nM or higher, 120 nM or higher, 125 nM or higher, 130 nM or higher, 135 nM or higher, 140 nM or higher, 145 nM or higher, 150 nM or higher, 160 nM or higher, 170 nM or higher, 180 nM or higher, 190 nM or higher, 200 nM or higher, 210 nM or higher, 220 nM or higher, 230 nM or higher, 240 nM or higher, 250 nM or higher, 260 nM or higher, 280 nM or higher, 300 nM or higher, 320 nM or higher, 340 nM or higher, 360 nM or higher, 380 nM or higher, 400 nM or higher, 450 nM or higher, 500 nM or higher, 550 nM or higher, 600 nM or higher, 650 nM or higher, 700 nM or higher, 750 nM or higher, 800 nM or higher, 850 nM or higher, 900 nM or higher, 950 nM or higher, 1000 nM or higher, 2 mM or higher, 3 mM or higher, 4 mM or higher, 5 mM or higher, or 10 mM or higher concentration of reporter binding agent. Ranges of reporter binding agent concentration in reagent compositions are specifically contemplated. All possible ranges are contemplated. For example, all ranges that can be formulated from the above reporter binding agent concentrations are specifically contemplated. Concentrations of amplification target circles, DNA polymerase, and rolling circle replication primers in reagent concentrations can generally be proportional to the concentration of reporter binding agents as discussed above and elsewhere herein. Thus, useful concentrations of amplification target circles, DNA polymerase, and rolling circle replication primers can be proportional, for example to the concentrations of reporter binding agent described above and elsewhere herein.

Reagent compositions can be made at any scale. Large scale assembly of reagent composition can be useful for making batches of reagent composition for use in a large number of assays and reactions. Any batch of reagent composition can be stored as a batch, or can be divided into aliquots. Such aliquots are useful to avoid repeated temperature changes of a batch when used repeatedly over time. The reagent compositions can be prepared at a sufficient concentration to allow convenient use. Generally, the concentration chosen can compromise between increased stability of the composition at higher concentrations, a sufficient level of dilution of the reagent when in an assay or reaction to minimize the effects of any components of the storage solution, and the convenience of manipulating aliquots of the reagent (very high concentrations of the composition could require manipulation of very small aliquots).

For storage of reagent compositions, it is useful to include glycerol in the composition solution. Glycerol can prevent or reduce freezing of the compositions when stored at low temperatures and prevent or reduce the effects of low temperature on the compositions. Any amount of glycerol can be used, but typically 20% to 50% of the composition solution, by weight or volume, can be glycerol. For example, reagent compositions can include 1%, 2%, 3%, 4%, 5%, 6%, 7%, 8%, 9%, 10%, 11%, 12%, 13%, 14%, 15%, 16%, 17%, 18%, 19%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 75%, 80%, 85%, or 90% glycerol, by weight or volume. Reagent compositions can include about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 75%, about 80%, about 85%, or about 90% glycerol, by weight or volume. Ranges of glycerol concentration in reagent compositions are specifically contemplated. All possible ranges are contemplated. For example, all ranges that can be formulated from the above glycerol concentrations are specifically contemplated.

Reagent compositions can be stored prior to use. Stability of the disclosed reagent compositions during storage is an advantage of the reagent compositions. Reagent compositions can be stored for any desired period of time. For example, reagent compositions can be stored for 5 minutes, 10 minutes, 15 minutes 20 minutes, 30 minutes, 40 minutes, 50 minutes, 60 minutes, 1 hour, 2 hours, 3 hours, 4 hours, 5 hours, 6 hours, 7 hours, 8 hours, 9 hours, 10 hours, 11 hours, 12 hours, overnight, 13 hours, 14 hours, 15 hours, 16 hours, 17 hours, 18 hours, 19 hours, 20 hours, 21 hours, 22 hours, 23 hours, 24 hours, 1 day, 2 days, 3 days, 4 days, 5 days, 6 days, 7 days, 1 week, 8 days, 9 days, 10 days, 12 days, 14 days, 2 weeks, 16 days, 18 days, 20 days, 22 days, 24 days, 26 days, 28 days, 30 days, 1 month, 2 months, 3 months, 4 months, 5 months, 6 months, 7 months, 8 months, 9 months, 10 months, 11 months, 12 months, or 1 year. Reagent compositions can be stored for about 5 minutes, about 10 minutes, about 15 minutes, about 20 minutes, about 30 minutes, about 40 minutes, about 50 minutes, about 60 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about overnight, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 1 week, about 8 days, about 9 days, about 10 days, about 12 days, about 14 days, about 2 weeks, about 16 days, about 18 days, about 20 days, about 22 days, about 24 days, about 26 days, about 28 days, about 30 days, about 1 month, about 2 months, about 3 months, about 4 months, about 5 months, about 6 months, about 7 months, about 8 months, about 9 months, about 10 months, about 11 months, about 12 months, or about 1 year. Reagent compositions can be stored for 5 minutes or longer, 10 minutes or longer, 15 minutes or longer, 20 minutes or longer, 30 minutes or longer, 40 minutes or longer, 50 minutes or longer, 60 minutes or longer, 1 hour or longer, 2 hours or longer, 3 hours or longer, 4 hours or longer, 5 hours or longer, 6 hours or longer, 7 hours or longer, 8 hours or longer, 9 hours or longer, 10 hours or longer, 11 hours or longer, 12 hours or longer, overnight or longer, 13 hours or longer, 14 hours or longer, 15 hours or longer, 16 hours or longer, 17 hours or longer, 18 hours or longer, 19 hours or longer, 20 hours or longer, 21 hours or longer, 22 hours or longer, 23 hours or longer, 24 hours or longer, 1 day or longer, 2 days or longer, 3 days or longer, 4 days or longer, 5 days or longer, 6 days or longer, 7 days or longer, 1 week or longer, 8 days or longer, 9 days or longer, 10 days or longer, 12 days or longer, 14 days or longer, 2 weeks or longer, 16 days or longer, 18 days or longer, 20 days or longer, 22 days or longer, 24 days or longer, 26 days or longer, 28 days or longer, 30 days or longer, 1 month or longer, 2 months or longer, 3 months or longer, 4 months or longer, 5 months or longer, 6 months or longer, 7 months or longer, 8 months or longer, 9 months or longer, 10 months or longer, 11 months or longer, 12 months or longer, or 1 year or longer. Stored reagent compositions need not be used at full activity and so can be stored under conditions and for a length of time that results in some loss of activity, although this is not preferred.

Reagent compositions can also be made up of reporter binding agents composed of a specific binding molecules and amplification target circles, rolling circle replication primers, and DNA polymerase. The rolling circle replication primers associate with the amplification target circle and the DNA polymerase associates with the amplification target circle and rolling circle replication primer. Reagent compositions can also include tertiary DNA strand displacement primers. Tertiary DNA strand displacement primers can associate with the amplification target circles in the reagent compositions. The components of the disclosed reagent compositions are described in detail elsewhere herein.

B. Reporter Binding Agents

A reporter binding agent is a specific binding molecule coupled or tethered to a nucleic acid such as an oligonucleotide. The specific binding molecule is referred to as the affinity portion of the reporter binding agent and the nucleic acid is referred to as the oligonucleotide portion of the reporter binding agent. As used herein, a specific binding molecule is a molecule that interacts specifically with a particular molecule or moiety (such as an analyte). The molecule or moiety that interacts specifically with a specific binding molecule is referred to herein as a target molecule. The target molecules can be, for example, any analyte. It is to be understood that the term target molecule refers to both separate molecules and to portions of molecules, such as an epitope of a protein, that interacts specifically with a specific binding molecule. Antibodies, either member of a receptor/ligand pair, and other molecules with specific binding affinities are examples of specific binding molecules, useful as the affinity portion of a reporter binding agent. A reporter binding agent with an affinity portion which is an antibody can be referred to as a reporter antibody. The oligonucleotide portion can be a nucleic acid molecule or a combination of nucleic acid molecules. For the disclosed reagent compositions, the oligonucleotide portion is a rolling circle replication primer. The oligonucleotide portion can also be an oligonucleotide or an amplification target circle.

By coupling an oligonucleotide to a specific binding molecule, binding of a specific binding molecule to its specific target can be detected by rolling circle amplification mediated by the oligonucleotide. This amplification allows sensitive detection of a very small number of bound specific binding molecules. A reporter binding agent that interacts specifically with a particular target molecule is said to be specific for that target molecule. For example, a reporter binding agent with an affinity portion which is an antibody that binds to a particular antigen is said to be specific for that antigen. The antigen is the target molecule. Reporter binding agents can also be referred to as reporter binding molecules. FIGS. 25, 26, 27, 28, and 29 of U.S. Pat. No. 6,143,495 illustrate examples of several preferred types of reporter binding agents and their use. FIG. 29 of U.S. Pat. No. 6,143,495 illustrates a reporter binding agent using an antibody as the affinity portion.

Reporter binding agents are a component of reagent compositions. Reporter binding agents can also be used in the disclosed methods separately from reagent compositions. For example, a reporter binding agent can be used as part of an assay to bind to and facilitate detection of amplification products produced using reagent compositions. Reporter binding agents for use in reagent compositions and for separate use are described herein. Many reporter binding agents can be used in either context. Reporter binding agents for use in reagent compositions include rolling circle replication primers as the oligonucleotide portion. Reporter binding agents for separate use can have many other forms of oligonucleotide portions.

Using a rolling circle replication primer as the oligonucleotide portion of a reporter binding agent allows rolling circle replication of an added ATC where the resulting TS-DNA is coupled to the reporter binding agent. Because of this, the TS-DNA will be effectively immobilized at the site of the target molecule. The immobilized TS-DNA can also be collapsed in situ prior to detection. The sequence of the rolling circle replication primer sequence can be arbitrarily chosen. The rolling circle replication sequence can be designed to form an intramolecular stem structure as described for rolling circle replication primers elsewhere herein. Additional, untethered rolling circle replication primers can also be used to achieve multiply-primed RCA. The rolling circle replication primer portion of the oligonucleotide portion of a reporter binding agent can be referred to as a rolling circle replication primer sequence.

When the oligonucleotide portion of a reporter binding agent is used as a rolling circle replication primer, the oligonucleotide portion can be any length that supports specific and stable hybridization between the oligonucleotide portion and the primer complement portion of an amplification target circle. Generally this is 10 to 35 nucleotides long, but is preferably 16 to 20 nucleotides long. The rolling circle replication primer of a reporter binding agent can have any of the features of rolling circle replication primers described elsewhere herein. FIGS. 25, 26, 27, 28, and 29 of U.S. Pat. No. 6,143,495 illustrate examples of reporter binding agents in which the oligonucleotide portion is a rolling circle replication primer.

In a multiplex assay using multiple reporter binding agents, it is preferred that the fluorescent change probes or primers used with each reporter binding agent be substantially different to limit the possibility of non-specific target detection. Alternatively, it may be desirable in some multiplex assays, to use fluorescent change probes or primers with related sequences. Such assays can use one or a few ATCs to detect a larger number of target molecules. Any of the other relationships between ATCs and primers and probes disclosed herein can also be used.

Antibodies useful as the affinity portion of reporter binding agents, can be obtained commercially or produced using well established methods. For example, Johnstone and Thorpe, on pages 30-85, describe general methods useful for producing both polyclonal and monoclonal antibodies. The entire book describes many general techniques and principles for the use of antibodies in assay systems.

Preferred target molecules are proteins and peptides. Use of reporter binding agents that target proteins and peptides allows sensitive signal amplification using rolling circle amplification for the detection of proteins and peptides. The ability to multiplex rolling circle amplification detection allows multiplex detection of the proteins and peptides (or any other target molecule). Thus, the disclosed method can be used for multi-protein analysis such as proteomics analysis. Such multi-protein analysis can be accomplished, for example, by using reporter binding agents targeted to different proteins, with the oligonucleotide portion of each reporter binding agent coded to allow separate amplification and detection of each different reporter binding agent.

In the disclosed reagent compositions, multiple reporter binding agents can be combined in one reagent composition. This can be accomplished, for example, by coupling the reporter binding agents together or including a component that allows the reporter binding agents to associate together. For this purpose, it is preferred that the reporter binding agents be coupled or associated together via linkers. Reporter binding agents can be coupled directly or via an linking molecule. The linking molecule can have any structure that allows the reporter binding agents and the reagent compositions of which they are a part to function as described herein. Reporter binding agents can also be associated together via non-covalent interactions either directly or via structures or molecules attached to the reporter binding agents. For example, linkers having moieties that can interact with each other can be coupled to different reporter binding agents and allowed to interact. One form of such linkers is an oligonucleotide containing peptide nucleic acid. By using complementary sequence in another oligonucleotide linker (which can be composed of ordinary nucleotide or peptide nucleic acid) coupled to another reporter binding agent, the reporter binding agents can be stably associated together. Many other forms of linkage can be used to associate multiple reporter binding agents.

In another form of reporter binding agent, the oligonucleotide portion of the reporter binding agent can include an amplification target circle which serves as a template for rolling circle replication. Such reporter binding agents can be used in another form of reagent composition made up of the reporter binding agent, one or more rolling circle replication primers annealed to the amplification target circle, and DNA polymerase. The properties and uses of such reagent compositions are similar to those of other reagent compositions disclosed herein. In a multiplex assay using multiple reporter binding agents, it is preferred that primer complement portions, detection tag portions and/or whatever portions of the ATC comprising the oligonucleotide portion of each reporter binding agent that match or are complementary to a fluorescent change probe or primer be substantially different to aid unique detection of each reporter binding agent. Where fluorescent change probes are used, it is desirable to use the same primer complement portion in all of the ATCs used in a multiplex assay. The ATC is tethered to the specific binding molecule by looping the ATC around a tether loop. This allows the ATC to rotate freely during rolling circle replication while remaining coupled to the affinity portion. The tether loop can be any material that can form a loop and be coupled to a specific binding molecule. Linear polymers are a preferred material for tether loops.

A preferred method of producing a reporter binding agent with a tethered ATC is to form the tether loop by ligating the ends of oligonucleotides coupled to a specific binding molecule around an ATC. Oligonucleotides can be coupled to specific binding molecules using known techniques. For example, Hendrickson et al. (1995), describes a suitable method for coupling oligonucleotides to antibodies. This method is generally useful for coupling oligonucleotides to any protein. To allow ligation, oligonucleotides comprising the two halves of the tether loop should be coupled to the specific binding molecule in opposite orientations such that the free end of one is the 5' end and the free end of the other is the 3' end. Ligation of the ends of the tether oligonucleotides can be mediated by hybridization of the ends of the tether oligonucleotides to adjacent sequences in the ATC to be tethered. In this way, the ends of the tether oligonucleotides are analogous to the target probe portions of an open circle probe, with the ATC containing the target sequence. Similar techniques can be used to form tether loops containing a target sequence.

Another useful method of producing a reporter binding agent with a tethered ATC is to ligate an open circle probe while hybridized to an oligonucleotide tether loop on a specific binding molecule. In this method, both ends of a single tether oligonucleotide are coupled to a specific binding molecule. This can be accomplished using known coupling techniques as described above. Ligation of an open circle probe hybridized to a tether loop is analogous to the ligation operation of LM-RCA. In this case, the target sequence is part of an oligonucleotide with both ends coupled to a specific binding molecule. This same ligation technique can be used to circularize open circle probes on target sequences that are part of reporter binding agents. This topologically locks the open circle probe to the reporter binding agent (and thus, to the target molecule to which the reporter binding agent binds).

The ends of linkers, linking molecules, and tether loops can be coupled to any specific binding molecule with functional groups that can be derivatized with suitable activating groups. When the specific binding molecule is a protein, or a molecule with similar functional groups, coupling of tether ends can be accomplished using known methods of protein attachment. Many such methods are described in *Protein immobilization: fundamentals and applications* Richard F. Taylor, ed. (M. Dekker, New York, 1991).

In another for or reporter binding agent, the oligonucleotide portion of the reporter binding agent includes a sequence, referred to as a target sequence, that serves as a target sequence for an open circle probe. The sequence of the target sequence can be arbitrarily chosen. In a multiplex assay using multiple reporter binding agents, it is preferred that the target sequence for each reporter binding agent be substantially different to limit the possibility of non-specific target detection. Alternatively, it may be desirable in some multiplex assays, to use target sequences with related sequences. By using different, unique gap oligonucleotides to fill different gap spaces, such assays can use one or a few open circle probes to amplify and detect a larger number of target sequences. The oligonucleotide portion can be coupled to the affinity portion by any of several established coupling reactions. For example, Hendrickson et al., *Nucleic Acids Res.*, 23(3):522-529 (1995) describes a suitable method for coupling oligonucleotides to antibodies.

A preferred form of target sequence in a reporter binding agent is an oligonucleotide having both ends coupled to the specific binding molecule so as to form a loop. In this way, when the open circle probe hybridizes to the target and is circularized, the open circle probe will remain topologically locked to the reporter binding agent during rolling circle replication of the circularized open circle probe. This improves the localization of the resulting amplified signal to the location where the reporter binding agent is bound (that is, at the location of the target molecule).

A special form of reporter binding agent, referred to herein as a reporter binding probe, has an oligonucleotide or oligonucleotide derivative as the specific binding molecule. Reporter binding probes can be used in any way that reporter binding agents can be used, including in reagent compositions. Reporter binding probes are designed for and used to detect specific nucleic acid sequences. Thus, the target molecules for reporter binding probes are nucleic acid sequences. The target molecule for a reporter binding probe can be a nucleotide sequence within a larger nucleic acid molecule. It is to be understood that the term reporter binding agent encompasses reporter binding probes. The specific binding molecule of a reporter binding probe can be any length that supports specific and stable hybridization between the reporter binding probe and the target molecule. For this purpose, a length of 10 to 40 nucleotides is preferred, with a specific binding molecule of a reporter binding probe 16 to 25 nucleotides long being most preferred.

It is preferred that the specific binding molecule of a reporter binding probe is peptide nucleic acid. Peptide nucleic acid forms a stable hybrid with DNA. This allows a reporter binding probe with a peptide nucleic acid specific binding molecule to remain firmly adhered to the target sequence during subsequent amplification and detection operations. This useful effect can also be obtained with reporter binding probes with oligonucleotide specific binding molecules by making use of the triple helix chemical bonding technology described by Gasparro et al., *Nucleic Acids Res.* 1994 22(14): 2845-2852 (1994). Briefly, the affinity portion of a reporter binding probe is designed to form a triple helix when hybridized to a target sequence. This is accomplished generally as known, preferably by selecting either a primarily homopurine or primarily homopyrimidine target sequence. The matching oligonucleotide sequence which constitutes the affinity portion of the reporter binding probe will be complementary to the selected target sequence and thus be primarily homopyrimidine or primarily homopurine, respectively. The reporter binding probe (corresponding to the triple helix probe described by Gasparro et al.) contains a chemically linked psoralen derivative. Upon hybridization of the reporter binding probe to a target sequence, a triple helix forms. By exposing the triple helix to low wavelength ultraviolet radiation, the psoralen derivative mediates cross-linking of the probe to the target sequence. FIGS. 25, 26, 27, and 28 of U.S. Pat. No. 6,143,495 illustrate examples of reporter binding agents that are reporter binding probes.

The specific binding molecule in a reporter binding probe can also be a bipartite DNA molecule, such as ligatable DNA probes adapted from those described by Landegren et al., *Science* 241:1077-1080 (1988). When using such a probe, the affinity portion of the probe can be assembled by target-mediated ligation of two oligonucleotide portions which hybridize to adjacent regions of a target nucleic acid. Thus, the components used to form the affinity portion of such reporter binding probes are a truncated reporter binding probe (with a truncated affinity portion which hybridizes to part of the target sequence) and a ligation probe which hybridizes to an adjacent part of the target sequence such that it can be ligated to the truncated reporter binding probe. The ligation probe can also be separated from (that is, not adjacent to) the truncated reporter binding probe when both are hybridized to the target sequence. The resulting space between them can then be filled by a second ligation probe or by gap-filling synthesis. For use in the disclosed methods, it is preferred that the truncated affinity portion be long enough to allow target-mediated ligation but short enough to, in the absence of ligation to the ligation probe, prevent stable hybridization of the truncated reporter binding probe to the target sequence during the subsequent amplification operation. For this purpose, a specific step designed to eliminate hybrids between the target sequence and unligated truncated reporter binding probes can be used following the ligation operation.

C. Rolling Circle Replication Primers

A rolling circle replication primer (RCRP) is an oligonucleotide or oligomer having sequence complementary to one or more primer complement portions of an amplification target circle or open circle probe (OCP). This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the ATC or OCP. That is, the RCRP would be complementary only to primer complement portions. If random or degenerate rolling circle replication primers are used, the primers collectively will be complementary to many sequences on an ATC or OCP. The complementary portion of a rolling circle replication primer can be any length that supports specific and stable hybridization between the primer and the primer complement portion. Generally this is 10 to 35 nucleotides long, but is preferably 16 to 20 nucleotides long. Random or degenerate rolling circle replication primers are preferably 4 to 10 nucleotides long, and most preferably 6, 7 or 8 nucleotides long. Useful rolling circle replication primers are fluorescent change primers.

Rolling circle replication primers form part of the disclosed reagent compositions. Rolling circle replication primers are coupled to or associated with specific binding molecules to form reporter binding agents that are associated with amplification target circles and DNA polymerase to form reagent compositions. Additional free or untethered rolling circle replication primers can be associated with the amplification target circles in reagent compositions. Rolling circle replication primers can be coupled to specific binding molecules directly or via a linker or other linking molecule. Multiple rolling circle replication primers can be coupled or associated with a specific binding molecule.

It is preferred that rolling circle replication primers also contain additional sequence at the 5' end of the RCRP that is not complementary to any part of the OCP or ATC. This sequence is referred to as the non-complementary portion of the RCRP. The non-complementary portion of the RCRP, if present, can serve to facilitate strand displacement during DNA replication. The non-complementary portion of a RCRP can be any length, but is generally 1 to 100 nucleotides long, and preferably 4 to 8 nucleotides long. The non-complementary portion can be involved in interactions that provide specialized effects. For example, the non-complementary portion can be used to link the complementary portion to a specific binding molecule to form a reporter binding agent. The non-complementary portion also can comprise a quencher complement portion that can hybridize to a peptide nucleic acid quencher or peptide nucleic acid fluor or that can form an intramolecular structure. Random or degenerate rolling circle replication primers preferably do not include a non-complementary portion. Rolling circle replication primers can also comprise fluorescent moieties or labels and quenching moieties. Rolling circle replication primers can be capable of forming an intramolecular stem structure involving one or both of the RCRP's ends. Such rolling circle replication primers are referred to herein as hairpin rolling circle replication primers. Primers forming intramolecular stem structures, and their use in rolling circle amplification, are described in U.S. patent application No. 09/803,713.

Rolling circle replication primers can also include modified nucleotides to make it resistant to exonuclease digestion. For example, the primer can have three or four phosphorothioate linkages between nucleotides at the 3' end of the primer. Such nuclease resistant primers allow selective degradation of excess unligated OCP and gap oligonucleotides that might otherwise interfere with hybridization of detection probes, address probes, and secondary OCPs to the amplified nucleic acid. A rolling circle replication primer can be used as the tertiary DNA strand displacement primer in strand displacement cascade amplification. Random or degenerate rolling circle replication primers can serve as secondary and tertiary DNA strand displacement primers.

A rolling circle replication primer is specific for, or corresponds to, an open circle probe or amplification target circle when the complementary portion of the rolling circle replication primer is complementary to the primer complement portion of the open circle probe or amplification target circle. A rolling circle replication primer is not specific for, or does not correspond to, an open circle probe or amplification target circle when the complementary portion of the rolling circle replication primer is not substantially complementary to the open circle probe or amplification target circle. A complementary portion is not substantially complementary to another sequence if it has a melting temperature 10° C. lower than the melting temperature under the same conditions of a sequence fully complementary to the complementary portion of the rolling circle replication primer.

A rolling circle replication primer is specific for, or corresponds to, a set of open circle probes or a set of amplification target circles when the complementary portion of the rolling circle replication primer is complementary to the primer complement portion of the open circle probes or amplification target circles in the set. A rolling circle replication primer is not specific for, or does not correspond to, a set of open circle probes or a set of amplification target circles when the complementary portion of the rolling circle replication primer is not substantially complementary to the open circle probes or amplification target circles in the set.

D. Amplification Target Circles

An amplification target circle (ATC) is a circular DNA molecule. ATCs are preferably single-stranded but can be partially or fully double-stranded. ATCs are associated with reporter binding agents and DNA polymerase to form reagent compositions. Portions of ATCs have specific functions making the ATC useful for rolling circle amplification (RCA). These portions are referred to as the primer complement portions, the secondary DNA strand displacement primer matching portions, the detection tag portions, the secondary target sequence portions, the address tag portions, and the promoter portions. At least one primer complement portion is a required element of an amplification target circle. For multiply-primed RCA, a plurality of primer complement portions are required. Where random or degenerate rolling circle replication primers are used, the sequence of the primer complement portions need not either be known or of a specified sequence. The amplification target circle can include at least one detection tag portion when fluorescent change probes (or other detection probes) are used for detection.

Secondary DNA strand displacement primer matching portions, detection tag portions, secondary target sequence portions, address tag portions, and promoter portions are optional. The primer complement portions, the secondary DNA strand displacement primer matching portions, the detection tag portions, the secondary target sequence portions, the address tag portions, and the promoter portion, if present, are preferably non-overlapping. However, various of these portions can be partially or completely overlapping if desired. Generally, an amplification target circle can be a circular DNA molecule comprising one or more primer complement portions. Amplification target circles can be single-stranded, double-stranded, or partially double-stranded. Useful amplification target circles can comprise one or more primer complement portions, one or more secondary DNA strand displacement primer matching portions, and one or more detection tag portions.

Those segments of the ATC that do not correspond to a specific portion of the ATC can be arbitrarily chosen sequences. It is preferred that ATCs do not have any sequences that are self-complementary, although this is not required. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides. A lack of self-complementary sequences and a lack of promoter sequences generally are not required in the case of amplification target circles including, derived from, or comprising nucleic acid molecules of interest. Such features generally will not be controlled for such amplification target circles.

Ligated and circularized open circle probes are a type of ATC, and as used herein the term amplification target circle includes ligated open circle probes and circularized open circle probes. An ATC can be used in the same manner as described herein for OCPs that have been ligated or circularized. Amplification target circles can be any desired length. Generally, amplification target circles designed for use as amplifiable labels can contain between 40 to 1000 nucleotides, more preferably between about 50 to 150 nucleotides, and most preferably between about 50 to 100 nucleotides. Amplification target circles including, derived from, or comprising nucleic acid molecules of interest can be any useful size, including, for example, the size of a plasmid, virus, vector, or artificial chromosome.

An amplification target circle, when replicated, gives rise to a long DNA molecule containing multiple repeats of sequences complementary to the amplification target circle. This long DNA molecule is referred to herein as tandem sequence DNA (TS-DNA). TS-DNA contains sequences complementary to the primer complement portions and, if present on the amplification target circle, the secondary DNA strand displacement primer matching portions, the detection tag portions, the secondary target sequence portions, the address tag portions, and the promoter portion. These sequences in the TS-DNA are referred to as primer sequences (which match the sequence of the rolling circle replication primers), spacer sequences (complementary to the spacer region), detection tags, secondary target sequences, address tags, and promoter sequences. The TS-DNA can also have sequence complementary to the matching portion of secondary DNA strand displacement primers. This sequence in the TS-DNA is referred to as the secondary DNA strand displacement primer complement or as the primer complement. Amplification target circles are useful as tags for specific binding molecules.

1. Primer Complement Portions

Primer complement portions are parts of an amplification target circle that are complementary to rolling circle replication primers (RCRP). Each ATC preferably has multiple primer complement portions. This allows rolling circle replication to initiate at multiple sites on the ATC. However, an ATC can include one or more than one primer complement portion. If multiple primer complement portions are present, they can have sequence complementary to the same rolling circle replication primer, different rolling circle replication primers, or a combination of the same and different rolling circle replication primers. A primer complement portion and its cognate primer can have any desired sequence so long as they are complementary to each other. The sequence of the primer complement portion is referred to as the primer complement sequence.

In general, the sequence of a primer complement can be chosen such that it is not significantly similar to any other portion of the ATC. The primer complement portion can be any length that supports specific and stable hybridization between the primer complement portion and the primer. For this purpose, a length of 10 to 35 nucleotides is preferred, with a primer complement portion 16 to 20 nucleotides long being most preferred. If random or degenerate rolling circle replication primers are used, the amplification target circles will have multiple primer complement portions that generally will not be, and need not be, specifically identified. If random or degenerate rolling circle replication primers are used, the primers and the primer complement portions are preferably 4 to 10 nucleotides long, and most preferably 6, 7 or 8 nucleotides long.

The primer complement portions can be located anywhere on the ATC, such as within the spacer region of an ATC. Primer complement portions can be anywhere on the ATC or circularized OCP. For example, in ATCs that are circularized OCPs, the primer complement portions can be adjacent to the right target probe, with the right target probe portion and the primer complement portion preferably separated by three to ten nucleotides, and most preferably separated by six nucleotides, from the proximate primer complement portion. This location prevents the generation of any other spacer sequences, such as detection tags and secondary target sequences, from unligated open circle probes during DNA replication. Such an arrangement is less useful when using multiply-primed RCA. A primer complement portion can also be a part of or overlap all or a part of the target probe portions and/or any gap space sequence, if present.

2. Secondary DNA Strand Displacement Primer Matching Portions

Secondary DNA strand displacement primer matching portions are parts of an amplification target circle that match sequence in secondary DNA strand displacement primers. The sequence in a secondary DNA strand displacement primer that matches a secondary DNA strand displacement primer matching portion in an ATC is referred to as the matching portion of the secondary DNA strand displacement primer. An ATC can include one or more than one primer matching portion. If multiple primer matching portions are present, they can have sequence matching the same secondary DNA strand displacement primer (which is preferred), different secondary DNA strand displacement primers, or a combination of the same and different secondary DNA strand displacement primers. A single secondary DNA strand displacement primer matching portion is preferred. A primer matching portion and its cognate primer can have any desired sequence so long as they are complementary to each other. The sequence of the primer matching portion can be referred to as the primer matching sequence. More specifically, the sequence of the secondary DNA strand displacement primer matching portion can be referred to as the secondary DNA strand displacement primer matching sequence.

In general, the sequence of a primer matching portion can be chosen such that it is not significantly similar to any other portion of the ATC. Primer matching portions can overlap with primer complement portions, although it is preferred that they not overlap. The primer matching portion can be any length that supports specific and stable hybridization between the primer complement portion in the resulting TS-DNA and the primer. For this purpose, a length of 10 to 35 nucleotides is preferred, with a primer matching portion 16 to 20 nucleotides long being most preferred. The primer matching portion can be located anywhere on the ATC, such as within the spacer region of an ATC. Primer matching portions can be anywhere on the ATC or circularized OCP. If random or degenerate rolling circle replication primers are used, they can act as secondary DNA strand displacement primer. In this case, the amplification target circles will have multiple secondary DNA strand displacement primer matching portions that generally will not be, and need not be, specifically identified. If random or degenerate rolling circle replication primers are used, the primers and the secondary DNA strand displacement primer matching portions are preferably 4 to 10 nucleotides long, and most preferably 6, 7 or 8 nucleotides long.

3. Detection Tag Portions

Detection tag portions are part of the spacer region of an amplification target circle. Detection tag portions have sequences matching the sequence of the complementary portion of detection probes. These detection tag portions, when amplified during rolling circle replication, result in TS-DNA having detection tag sequences that are complementary to the complementary portion of detection probes. If present, there can be one, two, three, or more than three detection tag portions on an ATC. For example, an ATC can have two, three or four detection tag portions. Most preferably, an ATC will have three detection tag portions. Generally, it is preferred that an ATC have 60 detection tag portions or less. There is no fundamental limit to the number of detection tag portions that can be present on an ATC except the size of the ATC. When there are multiple detection tag portions, they can have the same sequence or they can have different sequences, with each different sequence complementary to a different detection probe. It is preferred that an ATC contain detection tag portions that have the same sequence such that they are all complementary to a single detection probe. For some multiplex detection methods, it is preferable that ATCs contain up to six detection tag portions and that the detection tag portions have different sequences such that each of the detection tag portions is complementary to a different detection probe. If the amplification target circles include, are derived from, or comprise nucleic acid molecules of interest, some or all of the detection tag portions can be sequences of interest in the nucleic acid of interest. In this way, detection can be based on the amplification of the specific sequences of interest. The detection tag portions can each be any length that supports specific and stable hybridization between the detection tags and the detection probe. For this purpose, a length of 10 to 35 nucleotides is preferred, with a detection tag portion 15 to 20 nucleotides long being most preferred.

4. Secondary Target Sequence Portions

Secondary target sequence portions are part of the spacer region of an amplification target circle. Secondary target sequence portions have sequences matching the sequence of target probes of a secondary open circle probe. These secondary target sequence portions, when amplified during rolling circle replication, result in TS-DNA having secondary target sequences that are complementary to target probes of a secondary open circle probe. If present, there can be one, two, or more than two secondary target sequence portions on an ATC. It is preferred that an ATC have one or two secondary target sequence portions. Most preferably, an ATC will have one secondary target sequence portion. Generally, it is preferred that an ATC have 50 secondary target sequence portions or less. There is no fundamental limit to the number of secondary target sequence portions that can be present on an ATC except the size of the ATC. When there are multiple secondary target sequence portions, they can have the same sequence or they can have different sequences, with each different sequence complementary to a different secondary OCP. It is preferred that an ATC contain secondary target sequence portions that have the same sequence such that they are all complementary to a single target probe portion of a secondary OCP. If the amplification target circles include, are derived from, or comprise nucleic acid molecules of interest, some or all of the secondary target sequence portions can be sequences of interest in the nucleic acid of interest. In this way, further amplification can be based on the presence of the specific sequences of interest.

The secondary target sequence portions can each be any length that supports specific and stable hybridization between the secondary target sequence and the target sequence probes of its cognate secondary OCP. For this purpose, a length of 20 to 70 nucleotides is preferred, with a secondary target sequence portion 30 to 40 nucleotides long being most preferred. As used herein, a secondary open circle probe is an open circle probe where the target probe portions match or are complementary to secondary target sequences in another open circle probe or an amplification target circle. It is contemplated that a secondary open circle probe can itself contain secondary target sequences that match or are complementary to the target probe portions of another secondary open circle probe. Secondary open circle probes related to each other in this manner are referred to herein as nested open circle probes.

5. Address Tag Portions

Address tag portions are part of an amplification target circle. The address tag portion has a sequence matching the sequence of the complementary portion of an address probe. This address tag portion, when amplified during rolling circle replication, results in TS-DNA having address tag sequences that are complementary to the complementary portion of address probes. If present, there can be one, or more than one, address tag portions on an ATC. It is preferred that an ATC have one or two address tag portions. Most preferably, an ATC will have one address tag portion. Generally, it is preferred that an ATC have 50 address tag portions or less. There is no fundamental limit to the number of address tag portions that can be present on an ATC except the size of the ATC. When there are multiple address tag portions, they can have the same sequence or they can have different sequences, with each different sequence complementary to a different address probe. It is preferred that an ATC contain address tag portions that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred. Where the ATC is formed from an OCP, the address tag portion can be part either the target probe portions or the spacer region. In this case, the address tag portion preferably overlaps all or a portion of the target probe portions, and all of any intervening gap space. Most preferably, the address tag portion overlaps all or a portion of both the left and right target probe portions.

6. Promoter Portions

Promoter portions correspond to the sequence of an RNA polymerase promoter. A promoter portion can be included in an amplification target circle so that transcripts can be generated from the ATC or TS-DNA. The sequence of any promoter can be used, but simple promoters for RNA polymerases without complex requirements are preferred. It is also preferred that the promoter is not recognized by any RNA polymerase that may be present in the sample containing the target nucleic acid sequence. Preferably, the promoter portion corresponds to the sequence of a T7 or SP6 RNA polymerase promoter. The T7 and SP6 RNA polymerases are highly specific for particular promoter sequences. Other promoter sequences specific for RNA polymerases with this characteristic would also be preferred. Because promoter sequences are generally recognized by specific RNA polymerases, the cognate polymerase for the promoter portion of the ATC should be used for transcriptional amplification. Numerous promoter sequences are known and any promoter specific for a suitable RNA polymerase can be used. The promoter portion can be located anywhere within the spacer region of an ATC and can be in either orientation.

E. DNA Polymerases

DNA polymerases can be associated with reporter binding agents and amplification target circles to form reagent compositions. DNA polymerases useful in reagent compositions and in rolling circle replication must perform rolling circle replication of primed circular templates. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of amplification target circles and ligated OCP. A 5' to 3' exonuclease activity, if present, might result in the destruction of the synthesized strand. DNA polymerases for use in the disclosed compositions and methods can also be highly processive, if desired. The suitability of a DNA polymerase for use in the disclosed compositions and methods can be readily determined by assessing its ability to carry out rolling circle replication. Useful rolling circle DNA polymerases are bacteriophage φ29 DNA polymerase (U.S. Pat. Nos. 5,198,543 and 5,001,050 to Blanco et al.), Bst DNA polymerase, VENT® DNA polymerase (Kong et al., *J. Biol. Chem.* 268:1965-1975 (1993)), ThermoSequenase™, delta Tts DNA polymerase, Bca DNA polymerase (Journal of Biochemistry 113(3):401-10, 1993 Mar.), phage M2 DNA polymerase (Matsumoto et al., *Gene* 84:247 (1989)), phage φ PRD1 DNA polymerase (Jung et al., *Proc. Natl. Acad. Sci. USA* 84:8287 (1987)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), PRD1 DNA polymerase (Zhu and Ito, *Biochim. Biophys. Acta.* 1219:267-276 (1994)), modified T7 DNA polymerase (Tabor and Richardson, *J. Biol. Chem.* 262:15330-15333 (1987); Tabor and Richardson, *J. Biol. Chem.* 264:6447-6458 (1989); Sequenase™ (U.S. Biochemicals)), and T4 DNA polymerase holoenzyme (Kaboord and Benkovic, *Curr. Biol.* 5:149-157 (1995)). Particular useful are φ29 DNA polymerase, Bst DNA polymerase, VENT® DNA polymerase, T7 DNA polymerase, ThermoSequenase™, and delta Tts DNA polymerase.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in the disclosed method include T4 gene 32 DNA binding protein (Lizardi et al., *Nature Genetics* 19(3):225-232 (1998)), BMRF1 polymerase accessory subunit (Tsurumi et al., *J. Virology* 67(12):7648-7653 (1993)), adenovirus DNA-binding protein (Zijderveld and van der Vliet, *J. Virology* 68(2):1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)), single-stranded DNA binding proteins (SSB; Rigler and Romano, *J. Biol. Chem.* 270:8910-8919 (1995)), and calf thymus helicase (Siegel et al., *J Biol. Chem.* 267:13629-13635 (1992)). Strand displacement factors can be part of reagent compositions.

The ability of a polymerase to carry out rolling circle replication can be determined by using the polymerase in a rolling circle replication assay such as those described in Fire and Xu, *Proc. Natl. Acad. Sci. USA* 92:4641-4645 (1995) and in U.S. Pat. No. 6,143,495 (Example 1).

Another type of DNA polymerase can be used if a gap-filling synthesis step is used, such as in gap-filling LM-RCA (see U.S. Pat. No. 6,143,495, Example 3). When using a DNA polymerase to fill gaps, strand displacement by the DNA polymerase is undesirable. Such DNA polymerases are referred to herein as gap-filling DNA polymerases. Unless otherwise indicated, a DNA polymerase referred to herein without specifying it as a rolling circle DNA polymerase or a gap-filling DNA polymerase, is understood to be a rolling circle DNA polymerase and not a gap-filling DNA polymerase. Useful gap-filling DNA polymerases are T7 DNA polymerase (Studier et al., *Methods Enzymol.* 185:60-89 (1990)), DEEP VENT® DNA polymerase (New England Biolabs, Beverly, Mass.), modified T7 DNA polymerase (Tabor and Richardson, *J. Biol. Chem.* 262:15330-15333 (1987); Tabor and Richardson, *J. Biol. Chem.* 264:6447-6458 (1989); Sequenase™ (U.S. Biochemicals)), and T4 DNA polymerase (Kunkel et al., *Methods Enzymol.* 154:367-382 (1987)). An especially preferred type of gap-filling DNA polymerase is the *Thermus flavus* DNA polymerase (MBR, Milwaukee, Wis.). A particularly useful gap-filling DNA polymerase is the Stoffel fragment of Taq DNA polymerase (Lawyer et al., *PCR Methods Appl.* 2(4):275-287 (1993), King et al., *J. Biol. Chem.* 269(18):13061-13064 (1994)).

The ability of a polymerase to fill gaps can be determined by performing gap-filling LM-RCA. Gap-filling LM-RCA is performed with an open circle probe that forms a gap space when hybridized to the target sequence. Ligation can only occur when the gap space is filled by the DNA polymerase. If gap-filling occurs, TS-DNA can be detected, otherwise it can be concluded that the DNA polymerase, or the reaction conditions, is not useful as a gap-filling DNA polymerase.

F. Target Molecules

The disclosed reagent compositions are designed to interact with target molecules. A target molecule is a molecule with which the specific binding molecule of a reporter binding agent can interact. In general, any compound, moiety, or component of a compound or complex can be a target molecule. All that is required is that the specific binding molecule of a reporter binding agent can interact with the target molecule. One type of target molecule, referred to as a primary target molecule, is a target molecule that is the object of labeling or detection. Another type of target molecule, referred to as a secondary target molecule, is a target molecule that is associated with another molecule or composition, referred to as a molecule of interest, such that reagent compositions can associate with the molecule of interest via the secondary target molecule. In this case, the molecules of interest can be the object of labeling or detection and the target molecule serves as a tag to mediate association of reagent compositions with molecules of interest.

Target molecules can, but need not, range in size from 100 daltons to 1,000,000 daltons. It is to be understood that the term target molecule refers to both separate molecules and compositions and to portions of molecules and compositions, such as an epitope of a protein. Target molecules may contain modifications, both naturally occurring or induced in vitro or in vivo. Induced modifications include adduct formation such as hapten attachment, multimerization, complex formation by interaction with other chemical moieties, digestion or cleavage (by, for example, protease), and metal ion attachment or removal. The disclosed method can be used to detect and/or distinguish differences in the modification state of a target molecule, such as the phosphorylation or glycosylation state of proteins. Target molecules also can be nucleic acid sequences complementary to target probe portions of an open circle probe. Such target molecules are generally referred to herein as target sequences.

Target molecules can be associated directly or indirectly with substrates, preferably in arrays. Most preferred are microarrays. Target molecules can be captured and/or immobilized. Samples that contain or that may contain target molecules can be referred to as target samples.

Secondary target molecules can be any molecule or compound that can interact with a specific binding molecule and that is, or can be, associated with a molecule of interest. Some forms of the disclosed method involve labeling and detection of analytes using secondary target molecules and reagent compositions. In general, any compound, moiety, or component of a compound or complex can be an analyte. Preferred analytes are molecules or moieties that can be coupled to, associated with, or incorporated into, molecules of interest. Many molecules and moieties are suitable for this. Examples of preferred secondary target molecules are haptens, such as streptavidin and biotin, and antibodies specific for molecules of interest.

The disclosed method can involve use of nucleic acid molecules and nucleic acid sequences as nucleic acid molecules of interest and as a source for target molecules, target sequences and nucleic acid sequences of interest. Nucleic acid molecules of interest can be, or can be used in, amplification target circles. As used herein, unless the context indicates otherwise, the term nucleic acid molecule refers to both actual molecules and to nucleic acid sequences that are part of a larger nucleic acid molecule.

1. Analytes

Analytes are useful types of primary target molecules and molecules of interest. In general, any compound, moiety, or component of a compound or complex can be an analyte. Preferred analytes are peptides, proteins, and other macromolecules such as lipids, complex carbohydrates, proteolipids, membrane fragments, and nucleic acids. Analytes can also be smaller molecules such as cofactors, metabolites, enzyme substrates, metal ions, and metal chelates. Analytes can, but need not, range in size from 100 daltons to 1,000,000 daltons. It is to be understood that the term analyte refers to both separate molecules and to portions of molecules, such as an epitope of a protein.

Analytes may contain modifications, both naturally occurring or induced in vitro or in vivo. Induced modifications include adduct formation such as hapten attachment, multimerization, complex formation by interaction with other chemical moieties, digestion or cleavage (by, for example, protease), and metal ion attachment or removal. The disclosed method can be used to detect differences in the modification state of an analyte, such as the phosphorylation or glycosylation state of proteins.

Analytes can be associated directly or indirectly with substrates, preferably in arrays. Most preferred are microarrays. Analytes can be captured and/or immobilized using analyte capture agents. Immobilized analytes can be used to capture other components used in the disclosed method such as analyte capture agents and reporter binding primers. Samples that contain or that may contain analytes can be referred to as analyte samples.

G. Molecules of Interest

Some forms of the disclosed method involve labeling or detection of molecules of interest. In general, any compound, moiety, or component of a compound or complex can be a molecule of interest. Molecules of interest can be coupled to, associated with, or have incorporated, target molecules. Preferred molecules of interest are peptides, proteins, and other macromolecules such as lipids, complex carbohydrates, proteolipids, membrane fragments, and nucleic acids. Molecules of interest can also be smaller molecules such as cofactors, metabolites, enzyme substrates, metal ions, and metal chelates. Molecules of interest can, but need not, range in size from 100 daltons to 1,000,000 daltons. It is to be understood that the term molecule of interest refers to both separate molecules and to portions of molecules, such as an epitope of a protein.

Molecules of interest may contain modifications, both naturally occurring or induced in vitro or in vivo. Induced modifications include adduct formation such as hapten attachment, multimerization, complex formation by interaction with other chemical moieties, digestion or cleavage (by, for example, protease), and metal ion attachment or removal. The disclosed method can be used to detect differences in the modification state of a molecule of interest, such as the phosphorylation or glycosylation state of proteins. Molecules of interest can be associated directly or indirectly with substrates, preferably in arrays. Most preferred are microarrays. Molecules of interest can be captured and/or immobilized using analyte capture agents.

H. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide or oligomer having sequence matching part of the sequence of an OCP or ATC. This sequence in the secondary DNA strand displacement primer is referred to as the matching portion of the secondary DNA strand displacement primer. The sequence in the OCP or ATC that matches the matching portion of the secondary DNA strand displacement primer is referred to as the secondary DNA strand displacement primer matching portion. The matching portion of a secondary DNA strand displacement primer is complementary to sequences in TS-DNA. The matching portion of a secondary DNA strand displacement primer may be complementary to any sequence in TS-DNA. However, it is preferred that it not be complementary TS-DNA sequence matching either the rolling circle replication primers or a tertiary DNA strand displacement primer, if one is being used. This prevents hybridization of the primers to each other.

Secondary DNA strand displacement primers can be specific for, or correspond to, all of the amplification target circles or open circle probes in an amplification reaction or in a set of open circle probes or set of amplification target circles in an amplification reaction. A secondary DNA strand displacement primer is specific for, or corresponds to, an open circle probe or amplification target circle when the matching portion of the secondary DNA strand displacement primer matches the primer complement portion of the open circle probe or amplification target circle. A secondary DNA strand displacement primer is not specific for, or does not correspond to, an open circle probe or amplification target circle when the matching portion of the secondary DNA strand displacement primer does not substantially match sequence in the open circle probe or amplification target circle. A matching portion does not substantially match another sequence if it has a melting temperature with the complement of the other sequence that is 10° C. lower than the melting temperature under the same conditions of a sequence fully complementary to the matching portion of the secondary DNA strand displacement primer.

A secondary DNA strand displacement primer is specific for, or corresponds to, a set of open circle probes or a set of amplification target circles when the matching portion of the secondary DNA strand displacement primer matches the primer complement portion of the open circle probes or amplification target circles in the set. A secondary DNA strand displacement primer is not specific for, or does not correspond to, a set of open circle probes or a set of amplification target circles when the matching portion of the secondary DNA strand displacement primer does not substantially match the open circle probes or amplification target circles in the set. Secondary DNA strand displacement primers can be fluorescent change primers although this is not preferred.

It is preferred that secondary DNA strand displacement primers also contain additional sequence at the 5' end of the primer that does not match any part of the OCP or ATC. This sequence is referred to as the non-matching portion of the secondary DNA strand displacement primer. The non-matching portion of the secondary DNA strand displacement primer, if present, can serve to facilitate strand displacement during DNA replication. The non-matching portion of a secondary DNA strand displacement primer may be any length, but is generally 1 to 100 nucleotides long, and preferably 4 to 8 nucleotides long. The non-matching portion can be involved in interactions that provide specialized effects. For example, the non-matching portion can comprise a quencher complement portion that can hybridize to a peptide nucleic acid quencher or peptide nucleic acid fluor or that can form an intramolecular structure. Secondary DNA strand displacement primers can also comprise fluorescent moieties or labels and quenching moieties.

The matching portion of a secondary DNA strand displacement primer can be any length that supports specific and stable hybridization between the primer and its complement. Generally this is 12 to 35 nucleotides long, but is preferably 18 to 25 nucleotides long. The matching portion of a secondary DNA strand displacement primer can be complementary to all or a portion of the target sequence. In this case, it is preferred that the 3' end nucleotides of the secondary DNA strand displacement primer are complementary to the gap sequence in the target sequence. It is most preferred that nucleotide at the 3' end of the secondary DNA strand displacement primer falls complementary to the last nucleotide in the gap sequence of the target sequence, that is, the 5' nucleotide in the gap sequence of the target sequence.

Useful secondary DNA strand displacement primers for use in the disclosed method can form an intramolecular stem structure involving one or both of the secondary DNA strand displacement primer's ends. Such secondary DNA strand displacement primers are referred to herein as hairpin secondary DNA strand displacement primers. Primers forming intramolecular stem structures, and their use in rolling circle amplification, are described in published U.S. Patent Application No. 20030022167 A1.

Another form of DNA strand displacement primer, referred to herein as a tertiary DNA strand displacement primer, is an oligonucleotide having sequence complementary to part of the sequence of an OCP or ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the OCP or ATC. However, it is preferred that it not be complementary OCP or ATC sequence matching the secondary DNA strand displacement primer. This prevents hybridization of the primers to each other. Preferably, the complementary portion of the tertiary DNA strand displacement primer has sequence complementary to a portion of the spacer portion of an OCP. The complementary portion of a tertiary DNA strand displacement primer can be any length that supports specific and stable hybridization between the primer and its complement. Generally this is 12 to 35 nucleotides long, but is preferably 18 to 25 nucleotides long. Tertiary DNA strand displacement primers can be fluorescent change primers although this is not preferred. Tertiary DNA strand displacement primers can be part of reagent compositions. Tertiary DNA strand displacement primers in reagent compositions can be annealed to amplification target circles.

Useful tertiary DNA strand displacement primers for use in the disclosed method can form an intramolecular stem structure involving one or both of the tertiary DNA strand displacement primer's ends. Such tertiary DNA strand displacement primers are referred to herein as hairpin tertiary DNA strand displacement primers.

It is preferred that tertiary DNA strand displacement primers also contain additional sequence at their 5' end that is not complementary to any part of the OCP or ATC. This sequence is referred to as the non-complementary portion of the tertiary DNA strand displacement primer. The non-complementary portion of the tertiary DNA strand displacement primer, if present, serves to facilitate strand displacement during DNA replication. The non-complementary portion of a tertiary DNA strand displacement primer may be any length, but is generally 1 to 100 nucleotides long, and preferably 4 to 8 nucleotides long. A rolling circle replication primer is a preferred form of tertiary DNA strand displacement primer. Tertiary DNA strand displacement primers can also comprise fluorescent moieties or labels and quenching moieties.

DNA strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated OCP and gap oligonucleotides that might otherwise interfere with hybridization of detection probes, address probes, and secondary OCPs to the amplified nucleic acid. DNA strand displacement primers can be used for secondary DNA strand displacement and strand displacement cascade amplification, both described below and in U.S. Pat. No. 6,143,495.

I. Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes.

Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516-2521 (1997)) and scorpion primers (Thelwell et al., Nucleic Acids Res. 28(19):3752-3761 (2000)).

Cleavage activated primers are similar to cleavage activated probes except that they are primers that are incorporated into replicated strands and are then subsequently cleaved. Little et al., Clin. Chem. 45:777-784 (1999), describe the use of cleavage activated primers.

J. Detection Labels

To aid in detection and quantitation of nucleic acids amplified using the disclosed compositions and methods, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7', 1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037 and PCT Applications WO 97/17471 and WO 97/17076.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin-or digoxygenin-labeled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal. Labels can also be the disclosed reagent compositions.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

K. Target Samples

Target samples can be derived from any source that has, or is suspected of having, target molecules. A target sample is the source of target molecules. Target samples can contain, for example, a target molecule such as particular analytes or a pool of analytes. A target sample can include natural target molecule, chemically synthesized target molecules, or both. A target sample can be, for example, a sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful target samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

Nucleic acid samples can be derived from any source that has, or is suspected of having, nucleic acids. A nucleic acid sample is the source of nucleic acid molecules and nucleic acid sequences. Nucleic acid sample can contain, for example, a target nucleic acid, for example a specific mRNA or pool of mRNA molecules. The nucleic acid sample can contain RNA or DNA or both. The nucleic acid sample in certain embodiments can also include chemically synthesized nucleic acids. The nucleic acid sample can include any nucleotide, nucleotide analog, nucleotide substitute or nucleotide conjugate.

L. Detection Probes

Detection probes are labeled oligonucleotides or oligomers having sequence complementary to detection tags on TS-DNA or transcripts of TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Useful labels are biotin and fluorescent molecules. Useful detection probes are fluorescent change probes. A particularly useful detection probe is a molecular beacon (which is a form of fluorescent change probe). Molecular beacons are detection probes labeled with fluorescent moieties where the fluorescent moieties fluoresce only when the detection probe is hybridized (Tyagi and Kramer, *Nature Biotechnology* 14:303-308 (1996)). The use of such probes eliminates the need for removal of unhybridized probes prior to label detection because the unhybridized detection probes will not produce a signal. This is especially useful in multiplex assays.

One form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is described in U.S. Pat. No. 6,143,495.

M. Address Probes

Address probes are oligonucleotides or oligomers having a sequence complementary to address tags on TS-DNA or transcripts of TS-DNA. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. Preferably, the complementary portion of an address probe is complementary to all or a portion of the target probe portions of an OCP. Most preferably, the complementary portion of an address probe is complementary to a portion of either or both of the left and right target probe portions of an OCP and all or a part of any gap oligonucleotides or gap sequence created in a gap-filling operation (see FIG. 6 of U.S. Pat. No. 6,143,495). Address probe can contain a single complementary portion or multiple complementary portions. Preferably, address probes are coupled, either directly or via a spacer molecule, to a solid-state support. Such a combination of address probe and solid-state support are a useful form of solid-state detector. Address probes can be fluorescent change probes although this is not preferred.

N. Solid Supports

Solid supports are solid-state substrates or supports with which target molecules or amplification products of the disclosed method (or other components used in, or produced by, the disclosed method) can be associated. Target molecules can be associated with solid supports directly of indirectly. Amplification products can be associated with solid supports directly or indirectly. For example, amplification products can be bound to the surface of a solid support or associated with address probes, or detection probes immobilized on solid supports. An array detector is a solid support to which multiple different address probes or detection probes have been coupled in an array, grid, or other organized pattern. Target arrays are arrays of target molecules attached to solid supports. Analyte arrays are arrays of analytes attached to a solid support.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

An array can include a plurality of components (such as target molecules, target samples, detection probes, address probes, and amplification products) immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification of amplification products. Although useful, it is not required that the solid support be a single unit or structure. Sets of components can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730(1991). A method for immobilization of 3'-amine oligonucleotides on casein-coated slides is described by Stimpson et al., *Proc. Natl. Acad. Sci. USA* 92:6379-6383 (1995). A useful method of attaching oligonucleotides to solid-state substrates is described by Guo et al., *Nucleic Acids Res.* 22:5456-5465 (1994).

Methods for immobilizing antibodies and other proteins to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209-216 and 241-242, and *Immobilized Affinity Ligands*, Craig T. Hermanson et al., eds. (Academic Press, New York, 1992). Antibodies and other proteins can be attached to a substrate by chemically cross-linking a free amino group on the antibody or protein to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Each of the components immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

O. Solid-State Detectors

Solid-state detectors are solid supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a multiplex assay, address probes specific for numerous different amplified nucleic acids (each representing a different target sequence amplified via a different set of primers) can be immobilized in an array, each in a different location. Capture and detection will occur only at those array locations corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730 (1991). A method for immobilization of 3'-amine oligonucleotides on casein-coated slides is described by Stimpson et al., *Proc. Natl. Acad. Sci. USA* 92:6379-6383 (1995). A preferred method of attaching oligonucleotides to solid-state substrates is described by Guo et al., *Nucleic Acids Res.* 22:5456-5465 (1994). Examples of nucleic acid chips and arrays, including methods of making and using such chips and arrays, are described in U.S. Pat. Nos. 6,287,768, 6,288,220, 6,287,776, 6,297,006, and 6,291,193.

Different address probes and/or detection probes can be used together as a set. The set can be used as a mixture of all or subsets of the address probes and/or detection probes used separately in separate reactions, or immobilized on a solid support. Address probes and/or detection probes used separately or as mixtures can be physically separable through, for example, association with or immobilization on a solid support.

Some solid-state detectors useful in the disclosed method have detection antibodies or analyte capture agents attached to a solid-state substrate. Such antibodies and analyte capture agents can be specific for a molecule of interest. Captured molecules of interest can then be detected by binding of a second, reporter antibody, followed by amplification. The disclosed reagent samples can be used for this purpose. Such a use of antibodies in a solid-state detector allows amplification assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209-216 and 241-242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

P. Solid-State Samples

Solid-state samples are solid supports to which target molecules or target sequences have been coupled or adhered. Target molecules or target sequences are preferably delivered in a target sample or assay sample. A preferred form of solid-state sample is an array sample. An array sample is a solid-state sample to which multiple different target samples or assay samples have been coupled or adhered in an array, grid, or other organized pattern.

Solid-state substrates for use in solid-state samples can include any solid material to which target molecules or target sequences can be coupled or adhered. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Target molecules and target sequences immobilized on a solid-state substrate allow formation of target-specific TS-DNA localized on the solid-state substrate. Such localization provides a convenient means of washing away reaction components that might interfere with subsequent detection steps, and a convenient way of assaying multiple different samples simultaneously. Diagnostic TS-DNA can be independently formed at each site where a different sample is adhered. For immobilization of target sequences or other oligonucleotide molecules to form a solid-state sample, the methods described elsewhere herein can be used. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

A useful form of solid-state substrate is a glass slide to which up to 256 separate target samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487-470 (1995). Briefly, microarrays can be fabricated on poly-L-lysine-coated microscope slides (Sigma) with an arraying machine fitted with one printing tip. The tip is loaded with 1 µl of a DNA sample (0.5 mg/ml) from, for example, 96-well microtiter plates and deposited ~0.005 µl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

Q. RNA Polymerases

Any RNA polymerase which can carry out transcription in vitro and for which promoter sequences have been identified can be used in the disclosed rolling circle transcription method. Stable RNA polymerases without complex requirements are preferred. Most preferred are T7 RNA polymerase (Davanloo et al., *Proc. Natl. Acad. Sci. USA* 81:2035-2039 (1984)) and SP6 RNA polymerase (Butler and Chamberlin, *J. Biol. Chem.* 257:5772-5778 (1982)) which are highly specific for particular promoter sequences (Schenborn and Meirendorf, *Nucleic Acids Research* 13:6223-6236 (1985)). Other RNA polymerases with this characteristic are also useful. Because promoter sequences are generally recognized by specific RNA polymerases, the OCP or ATC should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

R. Oligonucleotide Synthesis

Amplification target circles, rolling circle replication primers, detection probes, address probes, DNA strand displacement primers, open circle probes, gap oligonucleotides and any other oligonucleotides can be synthesized using established oligonucleotide synthesis methods. Methods to produce or synthesize oligonucleotides are well known. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. Nos. 6,294,664 and 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

As used herein, degenerate refers to an oligonucleotide (or oligomer) in which one or more of the base positions is occupied by more than one base, that is, a mixture of oligonucleotides (or oligomers) of defined length in which one or more positions of an individual member of the mixture is occupied by a base selected at random from among more than one possibility for that position. Such collections of oligonucleotides (or oligomers) can be readily synthesized using standard oligonucleotide synthesis instruments and software. As used herein, random refers to an oligonucleotide (or oligomer) in which each of the base positions is occupied by a base selected at random from among a complete set of possibilities, but commonly limited to, for example, the four bases adenine (A), guanine (G), cytosine (C) and thymine (T) (or uracil (U)). For example, random oligonucleotides can be composed of the four nucleotides deoxyriboadenosine monophosphate (dAMP), deoxyribocytidine monophosphate (dCMP), deoxyriboguanosine monophosphate (dGMP), or deoxyribothymidine monophosphate (dTMP). Degenerate oligonucleotides (or oligomers) where not every base position is selected at random from among a complete set of possibilities can be referred to as partially random oligonucleotides (or oligomers).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

Oligonucleotides can be synthesized, for example, on a Perseptive Biosystems 8909 Expedite Nucleic Acid Synthesis system using standard β-cyanoethyl phosphoramidite coupling chemistry on synthesis columns (Glen Research, Sterling, Va.). Oxidation of the newly formed phosphites can be carried out using, for example, the sulfurizing reagent 3H-1,2-benzothiole-3-one-1,1-idoxide (Glen Research) or the standard oxidizing reagent after the first and second phosphoramidite addition steps. The thio-phosphitylated oligonucleotides can be deprotected, for example, using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

Hexamer oligonucleotides can be synthesized on a Perseptive Biosystems 8909 Expedite Nucleic Acid Synthesis system using standard β-cyanoethyl phosphoramidite coupling chemistry on mixed dA+dC+dG+dT synthesis columns (Glen Research, Sterling, Va.). The four phosphoramidites can be mixed in equal proportions to randomize the bases at each position in the oligonucleotide. Oxidation of the newly formed phosphites can be carried out using the sulfurizing reagent 3H-1,2-benzothiole-3-one-1,1-idoxide (Glen Research) instead of the standard oxidizing reagent after the first and second phosphoramidite addition steps. The thiophosphitylated oligonucleotides can be deprotected using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

So long as their relevant function is maintained, amplification target circles, rolling circle replication primers, detection probes, address probes, DNA strand displacement primers, open circle probes, gap oligonucleotides and any other oligonucleotides can be made up of or include modified nucleotides (nucleotide analogs). Many modified nucleotides are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)n O]m CH$_3$, —O (CH$_2$)n OCH$_3$, —O(CH$_2$)n NH$_2$, —O(CH$_2$)n CH$_3$, —O(CH$_2$)n —ONH$_2$, and —O(CH$_2$)nON[(CH$_2$)n CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety and/or sugar moiety. An example of a nucleitide substitute is peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Oligonucleotides can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such oligonucleotides can be referred to as chimeric oligonucleotides.

S. Open Circle Probes

An open circle probe (OCP) is a linear DNA molecule. OCPs can be any length, but preferably contain between 50 to 1000 nucleotides, more preferably between about 60 to 150 nucleotides, and most preferably between about 70 to 100 nucleotides. The OCP has a 5' phosphate group and a 3' hydroxyl group. This allows the ends to be ligated (to each other or to other nucleic acid ends) using a ligase, coupled, or extended in a gap-filling operation. Open circle probes can be partially double-stranded. Useful open circle probes can comprise one or more primer complement portions, one or more secondary DNA strand displacement primer matching portions, and one or more detection tag portions.

Portions of the OCP can have specific functions making the OCP useful for RCA and LM-RCA. These portions are referred to as the target probe portions, the primer complement portions, the spacer region, the secondary DNA strand displacement primer matching portions, the detection tag portions, the secondary target sequence portions, the address tag portions, and the promoter portions. These portions are analogous to similarly-named portions of ATCs and their further description elsewhere herein in the context of ATCs is applicable to the analogous portion in OCPs. The target probe portions and at least one primer complement portion are required elements of an open circle probe. The primer complement portion can be part of, for example, the spacer region. Detection tag portions, secondary target sequence portions, promoter portions, and additional primer complement portions are optional and, when present, can be part of, for example, the spacer region. Address tag portions are optional and, when present, can be part of, for example, the spacer region. The primer complement portions, and the detection tag portions, the secondary target sequence portions, the address tag portions, and the promoter portions, if present, can be non-overlapping. However, various of these portions can be partially or completely overlapping if desired. OCPs can be single-stranded but may be partially double-stranded. In use, the target probe portions of an OCP should be single-stranded so that they can interact with target sequences.

Generally, an open circle probe can be a single-stranded, linear DNA molecule comprising, from 5' end to 3' end, a 5' phosphate group, a right target probe portion, a spacer region, a left target probe portion, and a 3' hydroxyl group, with a primer complement portion present as part of the spacer region. Particularly useful open circle probes can comprise a right target probe portion, a left target probe portion, one or more primer complement portions, and a secondary DNA strand displacement primer matching portion. Those segments of the spacer region that do not correspond to a specific portion of the OCP can be arbitrarily chosen sequences. For multiply-primed RCA, a plurality of primer complement portions are required. Where random or degenerate rolling circle replication primers are used, the sequence of the primer complement portions need not either be known or of a specified sequence. The open circle probe can include at least one detection tag portion when fluorescent change probes (or other detection probes) are used for detection.

It is preferred that OCPs do not have any sequences that are self-complementary. It is considered that this condition is met if there are no complementary regions greater than six nucleotides long without a mismatch or gap. It is also preferred that OCPs containing a promoter portion do not have any sequences that resemble a transcription terminator, such as a run of eight or more thymidine nucleotides. A lack of self-complementary sequences and a lack of promoter sequences is generally not required in the case of open circle probes including, derived from, or comprising nucleic acid molecules of interest. Such features will generally not be controlled for such open circle probes.

The open circle probe, when ligated and replicated, gives rise to a long DNA molecule containing multiple repeats of sequences complementary to the open circle probe. This long DNA molecule is referred to herein as tandem sequences DNA (TS-DNA). TS-DNA contains sequences complementary to the target probe portions, the primer complement portion, the spacer region, and, if present on the open circle probe, the detection tag portions, the secondary target sequence portions, the address tag portions, and the promoter portion. These sequences in the TS-DNA are referred to as target sequences (which match the original target sequence), primer sequences (which match the sequence of the rolling circle replication primer), spacer sequences (complementary to the spacer region), detection tags, secondary target sequences, address tags, and promoter sequences. The TS-DNA will also have sequence complementary to the matching portion of secondary DNA strand displacement primers. This sequence in the TS-DNA is referred to as the secondary DNA strand displacement primer complement or as the primer complement.

Preferably, the promoter portion of an OCP is immediately adjacent to the left target probe and is oriented to promote transcription toward the 3' end of the open circle probe. This orientation results in transcripts that are complementary to TS-DNA, allowing independent detection of TS-DNA and the transcripts, and prevents transcription from interfering with rolling circle replication. Open circle probes can be capable of forming an intramolecular stem structure involving one or both of the OCP's ends. Such open circle probes are referred to herein as hairpin open circle probes. Open circle probes forming intramolecular stem structures, and their use in rolling circle amplification, are described in U.S. patent application Ser. No. 09/803,713.

1. Target Probe Portions

There are two target probe portions on each OCP, one at each end of the OCP. The target probe portions can each be any length that supports specific and stable hybridization between the target probes and the target sequence. For this purpose, a length of 10 to 35 nucleotides for each target probe portion is preferred, with target probe portions 15 to 25 nucleotides long being most preferred. The target probe portion at the 3' end of the OCP is referred to as the left target probe, and the target probe portion at the 5' end of the OCP is referred to as the right target probe. These target probe portions are also referred to herein as left and right target probes or left and right probes. The target probe portions are complementary to a target nucleic acid sequence.

The target probe portions are complementary to the target sequence, such that upon hybridization the 5' end of the right target probe portion and the 3' end of the left target probe portion are base-paired to adjacent nucleotides in the target sequence, with the objective that they serve as a substrate for ligation.

In another form of open circle probe, the 5' end and the 3' end of the target probe portions may hybridize in such a way that they are separated by a gap space. In this case the 5' end and the 3' end of the OCP may only be ligated if one or more additional oligonucleotides, referred to as gap oligonucleotides, are used, or if the gap space is filled during the ligation operation. The gap oligonucleotides hybridize to the target sequence in the gap space to form a continuous probe/target hybrid. The gap space may be any length desired but is generally ten nucleotides or less. It is preferred that the gap space is between about three to ten nucleotides in length, with a gap space of four to eight nucleotides in length being most preferred. Alternatively, a gap space could be filled using a DNA polymerase during the ligation operation. When using such a gap-filling operation, a gap space of three to five nucleotides in length is most preferred. As another alternative, the gap space can be partially bridged by one or more gap oligonucleotides, with the remainder of the gap filled using DNA polymerase.

T. Gap Oligonucleotides

Gap oligonucleotides are oligonucleotides that are complementary to all or a part of that portion of a target sequence which covers a gap space between the ends of a hybridized open circle probe. Gap oligonucleotides have a phosphate group at their 5' ends and a hydroxyl group at their 3' ends. This facilitates ligation of gap oligonucleotides to open circle probes, or to other gap oligonucleotides. The gap space between the ends of a hybridized open circle probe can be filled with a single gap oligonucleotide, or it can be filled with multiple gap oligonucleotides. For example, two 3 nucleotide gap oligonucleotides can be used to fill a six nucleotide gap space, or a three nucleotide gap oligonucleotide and a four nucleotide gap oligonucleotide can be used to fill a seven nucleotide gap space. Gap oligonucleotides are particularly useful for distinguishing between closely related target sequences. For example, multiple gap oligonucleotides can be used to amplify different allelic variants of a target sequence. By placing the region of the target sequence in which the variation occurs in the gap space formed by an open circle probe, a single open circle probe can be used to amplify each of the individual variants by using an appropriate set of gap oligonucleotides.

U. DNA ligases

Any DNA ligase is suitable for use in the disclosed amplification method. Useful ligases are those that preferentially form phosphodiester bonds at nicks in double-stranded DNA. That is, ligases that fail to ligate the free ends of single-stranded DNA at a significant rate are preferred. Thermostable ligases are especially useful. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590-4592 (1978)), AMPLIGASE® (Kalin et al., *Mutat. Res.,* 283 (2):119-123 (1992); Winn-Deen et al., *Mol Cell Probes* (England) 7(3):179-186 (1993 )), Taq DNA ligase (Barany, *Proc. Natl. Acad. Sci. USA* 88:189-193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177-180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction,* American Association for the Study of Liver Diseases (Chicago, Ill., Nov. 3-7, 1995)).

The frequency of non-target-directed ligation catalyzed by a ligase can be determined as follows. LM-RCA is performed with an open circle probe and a gap oligonucleotide in the presence of a target sequence. Non-targeted-directed ligation products can then be detected by using an address probe specific for the open circle probe ligated without the gap oligonucleotide to capture TS-DNA from such ligated probes. Target directed ligation products can be detected by using an address probe specific for the open circle probe ligated with the gap oligonucleotide. By using a solid-state detector with regions containing each of these address probes, both target directed and non-target-directed ligation products can be detected and quantitated. The ratio of target-directed and non-target-directed TS-DNA produced provides a measure of the specificity of the ligation operation. Target-directed ligation can also be assessed as discussed in Barany (1991).

V. Nucleic Acid Molecules

The disclosed method can involve use of nucleic acid molecules and nucleic acid sequences as nucleic acid molecules of interest and as a source for target molecules, target sequences and nucleic acid sequences of interest. Nucleic acid molecules of interest can be, or can be used in, amplification target circles. As used herein, unless the context indicates otherwise, the term nucleic acid molecule refers to both actual molecules and to nucleic acid sequences that are part of a larger nucleic acid molecule.

Nucleic acid samples can be derived from any source that has, or is suspected of having, nucleic acids. A nucleic acid sample is the source of nucleic acid molecules and nucleic acid sequences. Nucleic acid sample can contain, for example, a target nucleic acid, for example a specific mRNA or pool of mRNA molecules. The nucleic acid sample can contain RNA or DNA or both. The nucleic acid sample in certain embodiments can also include chemically synthesized nucleic acids. The nucleic acid sample can include any nucleotide, nucleotide analog, nucleotide substitute or nucleotide conjugate.

Nucleic acid molecule and sequences can be from any nucleic acid sample of interest. The source, identity, and preparation of many such nucleic acid samples are known. It is useful if nucleic acid samples known or identified for use in amplification or detection methods are used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, a crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

Nucleic acid molecules and nucleic acid sequences that have or are sequences complementary to target probe portions of an open circle probe are also referred to as target molecules and target sequences. Examples of such target molecules, target sequences, or sources of target sequences are mRNA molecules and cDNA molecules, although any nucleic acid molecule or sequence can be used in the disclosed compositions and method. Target sequences, which can be the object of amplification, can be any nucleic acid. Target sequences can include multiple nucleic acid molecules, such as in the case of mRNA amplification, multiple sites in a nucleic acid molecule, or a single region of a nucleic acid molecule. For example, target sequences can be mRNA and cDNA.

W. Nucleic Acid Samples

Nucleic acid samples can be derived from any source that has, or is suspected of having, nucleic acids. A nucleic acid sample is the source of nucleic acid molecules and nucleic acid sequences. Nucleic acid sample can contain, for example, a target nucleic acid, for example a specific mRNA or pool of mRNA molecules. The nucleic acid sample can contain RNA or DNA or both. The nucleic acid sample in certain embodiments can also include chemically synthesized nucleic acids. The nucleic acid sample can include any nucleotide, nucleotide analog, nucleotide substitute or nucleotide conjugate.

The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

U. Analyte Capture Agents

An analyte capture agent is any compound that can interact with an analyte and allow the analyte to be immobilized or separated from other compounds and analytes. An analyte capture agent includes an analyte interaction portion. Analyte capture agents can also include a capture portion. Analyte capture agents without a capture portion preferably are immobilized on a solid support. The analyte interaction portion of an analyte capture agent is a molecule that interacts specifically with a particular molecule or moiety. The molecule or moiety that interacts specifically with an analyte interaction portion can be an analyte or another molecule that serves as an intermediate in the interaction between the analyte interaction portion and the analyte. It is to be understood that the term analyte refers to both separate molecules and to portions of molecules, such as an epitope of a protein, that interacts specifically with an analyte interaction portion. Antibodies, either member of a receptor/ligand pair, and other molecules with specific binding affinities are examples of molecules that can be used as an analyte interaction portion of an analyte capture agent. The specific binding portion of an analyte capture agent can also be any compound or composition with which an analyte can interact, such as peptides. An analyte capture agent that interacts specifically with a particular analyte is said to be specific for that analyte. For example, an analyte capture agent with an analyte interaction portion that is an antibody that binds to a particular antigen is said to be specific for that antigen. The antigen is the analyte.

Examples of molecules useful as the analyte interaction portion of analyte capture agents are antibodies, such as crude (serum) antibodies, purified antibodies, monoclonal antibodies, polyclonal antibodies, synthetic antibodies, antibody fragments (for example, Fab fragments); antibody interacting agents, such as protein A, carbohydrate binding proteins, and other interactants; protein interactants (for example avidin and its derivatives); peptides; and small chemical entities, such as enzyme substrates, cofactors, metal ions/chelates, and haptens. Antibodies may be modified or chemically treated to optimize binding to surfaces and/or targets.

Antibodies useful as the analyte interaction portion of analyte capture agents, can be obtained commercially or produced using well-established methods. For example, Johnstone and Thorpe, on pages 30-85, describe general methods useful for producing both polyclonal and monoclonal antibodies. The entire book describes many general techniques and principles for the use of antibodies in assay systems.

The capture portion of an analyte capture agent is any compound that can be associated with another compound. Preferably, a capture portion is a compound, such as a ligand or hapten, that binds to or interacts with another compound, such as ligand-binding molecule or an antibody. It is also preferred that such interaction between the capture portion and the capturing component be a specific interaction, such as between a hapten and an antibody or a ligand and a ligand-binding molecule. Examples of haptens include biotin, FITC, digoxigenin, and dinitrophenol. The capture portion can be used to separate compounds or complexes associated with the analyte capture agent from those that do not.

Capturing analytes or analyte capture agents on a substrate may be accomplished in several ways. In one embodiment, capture docks are adhered or coupled to the substrate. Capture docks are compounds or moieties that mediate adherence of an analyte by binding to, or interacting with, the capture portion on an analyte capture agent (with which the analyte is, or will be, associated). Capture docks immobilized on a substrate allow capture of the analyte on the substrate. Such capture provides a convenient means of washing away reaction components that might interfere with subsequent steps. Alternatively, analyte capture agents can be directly immobilized on a substrate. In this case, the analyte capture agent need not have a capture portion.

In one embodiment, the analyte capture agent or capture dock to be immobilized is an anti-hybrid antibody. Methods for immobilizing antibodies and other proteins to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is a heterobifunctional cross-linking agent such as N-[γ-maleimidobutyryloxy]succinimide ester (GMBS). These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209-216 and 241-242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino, carboxyl, or sulfur groups using glutaraldehyde, carbodiimides, or heterobifunctional agents such as GMBS as cross-linkers. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

One useful form of analyte capture agents are peptides. When various peptides are immobilized in an array, they can be used as "bait" for analytes. For example, an array of different peptides can be used to access whether a sample has analytes that interact with any of the peptides. Comparisons of different samples can be made by, for example, noting differences in the peptides to which analytes in the different samples become associated. In another form of the disclosed method, an array of analyte capture agents specific for analytes of interest can be used to access the presence of a whole suite of analytes in a sample.

V. Target Fingerprints

The disclosed method can identify, produce, or generate information about, for example, the presence, absence, amount, level, or condition of target molecules, target sequences, and analytes. Such information can be referred to as a target fingerprint. Target fingerprints can be used for any purpose and in any other method as appropriate for the type and quality of information involved. For example, the amount of an analyte in one sample can be compared to the amount of the same analyte in a different sample.

Informational content of, or derived from, the disclosed method can also be stored. Such information can be stored, for example, in or as computer readable media. Information generated in the disclosed method can be combined with information obtained or generated from any other source. The informational nature of target fingerprints produced using the disclosed method lends itself to combination and/or analysis using known bioinformatics systems and methods.

Target fingerprints of samples can be compared to similar target fingerprints derived from any other sample to detect similarities and differences in the samples (which is indicative of similarities and differences in the target molecules in the samples). For example, a target fingerprint of a first sample can be compared to a target fingerprint of a sample from the same type of organism as the first sample, a sample from the same type of tissue as the first sample, a sample from the same organism as the first sample, a sample obtained from the same source but at time different from that of the first sample, a sample from an organism different from that of the first sample, a sample from a type of tissue different from that of the first sample, a sample from a strain of organism different from that of the first sample, a sample from a species of organism different from that of the first sample, or a sample from a type of organism different from that of the first sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient or a different individual animal. Different organism includes a different organism of the same type or organisms of different types. A different type of organism refers to organisms of different types such as a dog and cat, a human and a mouse, or *E. coli* and Salmonella. A different type of tissue refers to tissues of different types such as liver and kidney, or skin and brain. A different strain or species of organism refers to organisms differing in their species or strain designation as those terms are understood in the art.

W. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for rolling circle amplification, the kit comprising one or more reagent compositions and one or more components or reagents for rolling circle amplification, detection of amplification products, or both. For example, the kits can include one or more reagent compositions and one or more rolling circle replication primers, one or more DNA strand displacement primers, one or more fluorescent change probes, or a combination. Another form of kit can comprise a plurality of reagent compositions. The kits also can contain, for example, nucleotides, buffers, ligase, open circle probes, gap oligonucleotides, or a combination.

X. Mixtures

Disclosed are mixtures formed by preparing the disclosed composition or performing or preparing to perform the disclosed methods. For example, disclosed are mixtures comprising a plurality of reagent compositions; a plurality of reagent compositions, and one or more DNA strand displacement primers; a plurality of reagent compositions, and one or more fluorescent change probes; a plurality of reagent compositions, one or more DNA strand displacement primers, and one or more fluorescent change probes; a plurality of reagent compositions, and tandem sequence DNA; a plurality of reagent compositions, one or more DNA strand displacement primers, one or more fluorescent change probes, and tandem sequence DNA; a plurality of reagent compositions, and secondary tandem sequence DNA; a plurality of reagent compositions, one or more DNA strand displacement primers, and secondary tandem sequence DNA; a plurality of reagent compositions, one or more fluorescent change probes, and secondary tandem sequence DNA; a plurality of reagent compositions, tandem sequence DNA, and secondary tandem sequence DNA; a plurality of reagent compositions, one or more DNA strand displacement primers, one or more fluorescent change probes, tandem sequence DNA, and secondary tandem sequence DNA; one or more reagent compositions, and one or more DNA strand displacement primers; one or more reagent compositions, and one or more fluorescent change probes; one or more reagent compositions, one or more DNA strand displacement primers, and one or more fluorescent change probes; one or more reagent compositions, and tandem sequence DNA; one or more reagent compositions, one or more DNA strand displacement primers, one or more fluorescent change probes, and tandem sequence DNA; one or more reagent compositions, and secondary tandem sequence DNA; one or more reagent compositions, one or more DNA strand displacement primers, and secondary tandem sequence DNA; one or more reagent compositions, one or more fluorescent change probes, and secondary tandem sequence DNA; one or more reagent compositions, tandem sequence DNA, and secondary tandem sequence DNA; one or more reagent compositions, one or more DNA strand displacement primers, one or more fluorescent change probes, tandem sequence DNA, and secondary tandem sequence DNA; one or more reporter binding agents, one or more amplification target circles, and DNA polymerase; one or more reporter binding agents, one or more amplification target circles, DNA polymerase, and one or more DNA strand displacement primers; one or more reporter binding agents, one or more amplification target circles, DNA polymerase, and one or more fluorescent change probes; one or more reporter binding agents, one or more amplification target circles, DNA polymerase, one or more DNA strand displacement primers, and one or more fluorescent change probes; one or more reporter binding agents, one or more amplification target circles, DNA polymerase, and tandem sequence DNA; one or more reporter binding agents, one or more amplification target circles, DNA polymerase, one or more DNA strand displacement primers, one or more fluorescent change probes, and tandem sequence DNA; one or more reporter binding agents, one or more amplification target circles, DNA polymerase, and secondary tandem sequence DNA; one or more reporter binding agents, one or more amplification target circles, DNA polymerase, one or more DNA strand displacement primers, and secondary tandem sequence DNA; one or more reporter binding agents, one or more amplification target circles, DNA polymerase, one or more fluorescent change probes, and secondary tandem sequence DNA; one or more reporter binding agents, one or more amplification target circles, DNA polymerase, tandem sequence DNA, and secondary tandem sequence DNA; one or more reporter binding agents, one or more amplification target circles, DNA polymerase, one or more DNA strand displacement primers, one or more fluorescent change probes, tandem sequence DNA, and secondary tandem sequence DNA; one or more reporter binding agents, one or more rolling circle replication primers, and DNA polymerase; one or more reporter binding agents, one or more rolling circle replication primers, DNA polymerase, and one or more DNA strand displacement primers; one or more reporter binding agents, one or more rolling circle replication primers, DNA polymerase, and one or more fluorescent change probes; one or more reporter binding agents, one or more rolling circle replication primers, DNA polymerase, one or more DNA strand displacement primers, and one or more fluorescent change probes; one or more reporter binding agents, one or more rolling circle replication primers, DNA polymerase, and tandem sequence DNA; one or more reporter binding agents, one or more rolling circle replication primers, DNA polymerase, one or more DNA strand displacement primers, one or more fluorescent change probes, and tandem sequence DNA; one or more reporter binding agents, one or more rolling circle replication primers, DNA polymerase, and secondary tandem sequence DNA; one or more reporter binding agents, one or more rolling circle replication primers, DNA polymerase, one or more DNA strand displacement primers, and secondary tandem sequence DNA; one or more reporter binding agents, one or more rolling circle replication primers, DNA polymerase, one or more fluorescent change probes, and secondary tandem sequence DNA; one or more reporter binding agents, one or more rolling circle replication primers, DNA polymerase, tandem sequence DNA, and secondary tandem sequence DNA; and one or more reporter binding agents, one or more rolling circle replication primers, DNA polymerase, one or more DNA strand displacement primers, one or more fluorescent change probes, tandem sequence DNA, and secondary tandem sequence DNA.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

Y. Systems

Disclosed are systems useful for performing, or aiding in the performance of, the disclosed method. Also disclosed are systems for producing reagent compositions. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising solid supports and reagent compositions.

Z. Data Structures and Computer Control

Disclosed are data structures used in, generated by, or generated from, the disclosed method. Data structures generally are any form of data, information, and/or objects collected, organized, stored, and/or embodied in a composition or medium. A target fingerprint stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Uses

The disclosed compositions and methods are applicable to numerous areas including, but not limited to, detection and/or analysis of target molecules, analytes, and molecules of interest, disease detection, protein detection, protein mapping, proteomics, mutation detection, gene discovery, gene mapping, and agricultural research. Particularly useful are assays to detect proteins and peptides. Other uses include, for example, detection of target molecules in cells and on target arrays arrays; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Method

Disclosed methods useful for labeling and detection of analytes. The methods involve rolling circle amplification. The methods generally make use of compositions that are associations of three components: reporter binding agents, amplification target circles, and DNA polymerase. These compositions, which can be referred to as reagent compositions, provide the main components for a rolling circle amplification reaction in a pre-assembled association, thus providing a convenient reagent for carrying out rolling circle amplification. The reporter binding agent is used to associate the reagent composition with a target molecule. This association allows amplified signal (the result of rolling circle amplification) to be associated with and/or correlated with the presence of the target molecule. Reporter binding agents generally are composed of a specific binding molecule and a rolling circle replication primer. The specific binding molecule and rolling circle replication primer are coupled, linked or otherwise associated with each other. The specific binding molecule can interact specifically with a target molecule (such as an analyte or label) and thus mediates association of the reagent composition to the target molecule.

The rolling circle replication primer is used to prime rolling circle replication of the amplification target circle. For this purpose, the rolling circle replication primer has sequence complementary to the amplification target circle. This complementarity also allows the rolling circle replication primer and amplification target circle to associate together through hybridization in the reagent composition. DNA polymerase catalyzes replication of the amplification target circle to form amplification products of rolling circle amplification. The DNA polymerase can interact with the rolling circle replication primer and amplification target circle. In the reagent composition, this interaction can take the form of a complex of polymerase, primer and template ready for replication. The interactions of the three components in the reagent compositions provide increased stability over the components individually. Thus, the reagent compositions can be assembled prior to their use in a rolling circle amplification reaction and can be stored and transported prior to use without substantial loss of activity. The compositions can reduce the difficultly of performing rolling circle amplification reactions by reducing the number of components that must be mixed at the time of the reaction and can improve consistency between rolling circle amplification reactions through the use of the same reagent composition in the reactions.

For use as a general reagent, the reagent composition can be produced and stored as a complex of the three components and in the absence of other components and reagents that may be used in an amplification reaction. For example, the specific binding molecule in the reagent composition will not be bound to the target molecule until the composition is used in an assay. The composition generally will not include any nucleotides needed for replication. The amplification target circle generally will not be amplified prior to use of the composition in an assay. However, in some forms, the reagent composition can include other components and reagents for amplification such as nucleotides, additional primers, detection probes, and labels.

In use, the reagent compositions generally will be associated with a target molecule, via the specific binding molecule of the reporter binding agent, and a signal can be generated by performing rolling circle amplification of the amplification target circle. The DNA polymerase catalyzes replication primed by the rolling circle replication primer of the reporter binding agent. Rolling circle replication refers to replication of a circular nucleic acid template (referred to as an amplification target circle; ATC) to form a long strand (referred to as tandem sequence DNA; TS-DNA) with tandem repeats of the sequence complementary to the circular template. Rolling circle amplification (RCA) refers to nucleic acid amplification reactions involving rolling circle replication and, optionally, additional types and levels of nucleic acid replication and amplification. Rolling circle amplification can produce a large amount of amplification products in a short time, thus providing a large and easily detected signal from a single amplification target circle. Rolling circle amplification refers both to rolling circle replication and to processes involving both rolling circle replication and additional forms of replication and amplification (such as replication of tandem sequence DNA). The disclosed reagent compositions are ideally suited for rolling circle replication and amplification because they include the key components of rolling circle replication: primer (the rolling circle replication primer), template (the amplification target circle), and DNA polymerase.

The disclosed compositions can be used to label and/or detect an analyte of interest. For use in labeling and/or detecting analytes, the specific binding molecule of the reagent composition can be a molecule or moiety that can interact specifically with the analyte. Antibodies are a form of specific binding molecule that can provide specific binding to a wide variety of possible analytes. In this use, the reagent composition provides a target-specific, amplifiable label for any analyte of interest. The amplified label will be tandem sequence DNA and other amplification products. The analyte can be detected by detecting the amplification products.

Some forms of the disclosed compositions can be used to detect and/or analyze any molecule, composition or structure that can be labeled with, or have incorporated, a target molecule (which, for this purpose, serves as a tag or label). Such labeled molecules can be detected and/or analyzed using forms of reagent composition that can interact with the target molecule. For this purpose, the reagent compositions can have specific binding molecules that can interact with particular moieties or molecules that are present on, or are used to label, any molecule of interest. Any molecules to be detected can be labeled with a target molecule for which the specific binding molecule in the reagent composition is specific. In this way, any molecule of interest can be associated with the reagent composition and labeled with amplification products of rolling circle amplification. For example, molecules of interest can be labeled with biotin. By using a reagent composition where the specific binding molecule is streptavidin or another biotin-specific molecule (such as an anti-biotin antibody), the reagent composition can be associated with any of the labeled molecules. This reagent composition can be used with any biotinylated target molecule. Any other suitable molecule or moiety can be in a similar manner in to biotin as a label to mediate association of reagent compositions with molecules of interest.

Also disclosed are immunoassay methods. The disclosed reagent compositions can be used as a universal reagent in immunoassays. In some immunoassays, an analyte-specific antibody can be bound to the analyte and a second antibody, specific for the type of antibody used as the analyte-specific antibody, can be used as the specific binding molecule in a reagent composition to bind the reagent composition to the analyte-specific antibody. For example, if the antigen-specific antibody is a mouse antibody, then the second antibody (that is, the specific binding molecule in the reagent composition) can be an anti-mouse antibody. Once the reagent composition is associated with the antigen-specific antibody, the amplification target circle can be amplified to produce amplification product that can be detected. An anti-mouse reagent composition such as this can be used to label and detect any analyte-or antigen-specific mouse antibody. Generalizing, any, for example, source-, class-, allotype-, or isotype-specific antibody can be used as the specific binding molecule in a reagent composition to label and detect all analyte-and antigen-specific antibodies of the relevant source, class, allotype, or isotype. This is analogous to the use of antibodies specific to a class of antibodies in sandwich immunoassays. The disclosed reagents compositions provide greater signal amplification and tighter localization of the signal than in traditional immunoassays. As used herein, a source-specific antibody is an antibody that reacts to many, most, or a substantial number of antibodies from a particular animal or organism or from a particular type of animal or organism. As used herein, a class-specific antibody is an antibody that reacts to many, most, or a substantial number of antibodies of a particular class of antibodies. As used herein, an allotype-specific antibody is an antibody that reacts to many, most, or a substantial number of antibodies of a particular allotype. As used herein, an isotype-specific antibody is an antibody that reacts to many, most, or a substantial number of antibodies of a particular isotype.

The disclosed compositions and methods can be used for real-time detection of rolling circle amplification products. Real-time detection is detection that takes place during the amplification reaction or operation. Generally, such detection can be accomplished by detecting amplification product at one or more discrete times during amplification, continuously during all or one or more portions of the amplification, or a combination of discrete times and continuous detection. Real-time detection can be aided by the use of labels or moieties that embody or produce a detectable signal that can be detected without disrupting the amplification reaction or operation. Fluorescent labels are an example of useful labels for real-time detection. A particularly useful means of obtaining real-time detection is the use of fluorescent change probes and/or primers in the amplification operation. With suitably designed fluorescent change probes and primers, fluorescent signals can be generated as amplification proceeds. In most such cases, the fluorescent signals will be in proportion to the amount of amplification product and/or amount of target sequence or target molecule.

The disclosed reagent compositions can be amplified using multiply-primed rolling circle amplification (MPRCA). Rolling circle replication can be primed at one or more sites on the amplification target circle. Multiply-primed RCA refers to RCA where replication is primed at a plurality of sites on the circular template. In this form of the method, the rolling circle replication primer in the reagent composition primes at one of the sites and one or more additional primers prime at other sites on the amplification target circle. The additional primers can be separate from the reagent composition. Multiply-primed RCA increases the sensitivity of amplification over singly-primed rolling circle amplification.

A. Use of Reagent Compositions

The disclosed methods use reagent compositions made up of reporter binding agents, amplification target circles, and DNA polymerase. The amplification target circle can be amplified as described herein using the DNA polymerase. The reporter binding agent can be made up of a specific binding molecule and a rolling circle replication primer. The rolling circle replication primer primes rolling circle replication of the amplification target circle by the DNA polymerase. Other forms of reagent compositions, as described elsewhere herein, can also be used in the methods. The affinity portion of the reporter binding agent is a specific binding molecule specific for a target molecule, such as proteins or peptides. The reporter binding agent is associated with the target molecule and detection of this interaction is mediated by rolling circle amplification. Unbound reporter binding agents can be removed by washing. Once the reagent composition is associated with a target molecule (via the reporter binding agent in the reagent composition), the associated amplification target circle can be amplified to detect the target molecule. The resulting TS-DNA is associated with the reporter binding agent, thus associating the TS-DNA to the site of the target molecule.

Reagent compositions can be used with a solid-state substrate and in combination with combinatorial multicolor coding. For this purpose, samples to be tested can be incorporated into a solid-state sample, as described elsewhere herein. The solid-state substrate can be, for example, a glass slide or a chip, and the solid-state sample can incorporate up to, for example, 256 individual target, analyte, or assay samples arranged in dots. Multiple solid-state samples can be used to either test more individual samples, or to increase the number of distinct target molecules to be detected. In the later case, each solid-state sample can have an identical set of sample dots, and the assay can be carried out using a different set of reagent compositions (having different amplification target circles) for each solid-state sample. This allows a large number of individuals and target molecules to be assayed in a single assay. By using up to six different labels, combinatorial multicolor coding allows up to 63 distinct targets to be detected on a single solid-state sample. When using multiple solid-state substrates and performing RCA with a different set of reagent compositions for each solid-state substrate, the same labels can be used with each solid-state sample (although differences between ATCs in each set may require the use of different detection probes). For example, 10 replica slides, each with 256 target sample dots, can be subjected to RCA using 10 different sets of reagent compositions (representing 10 different amplification target circles), where each set is designed for combinatorial multicolor coding of 63 targets. This results in an assay for detection of 630 different target molecules.

After rolling circle amplification, a cocktail of detection probes can be added, where the cocktail contains color combinations that are specific for each ATC. The design and combination of such detection probes for use in combinatorial multicolor coding is described elsewhere herein. The labels for combinatorial multicolor detection can be used in the manner of fluorescent change probes. It is preferred that the ATCs be designed with combinatorially coded detection tags to allow use of a single set of singly labeled detection probes. Collapsing detection probes can also be used.

B. Rolling Circle Amplification

The disclosed methods involve rolling circle amplification. Rolling circle amplification refers to nucleic acid amplification reactions where a circular nucleic acid template is replicated in a single long strand with tandem repeats of the sequence of the circular template. This first, directly produced tandem repeat strand is referred to as tandem sequence DNA (TS-DNA) and its production is referred to as rolling circle replication. Rolling circle amplification refers both to rolling circle replication and to processes involving both rolling circle replication and additional forms of amplification. For example, tandem sequence DNA can be replicated to form complementary strands referred to a secondary tandem sequence DNA. Secondary tandem sequence DNA can, in turn, be replicated, and so on. Tandem sequence DNA can also be transcribed. Rolling circle amplification involving production of only the first tandem sequence DNA (that is, the replicated strand produced by rolling circle replication) can be referred to as of linear rolling circle amplification (where "linear" refers to the general amplification kinetics of the amplification).

When rolling circle amplification is involved the rolling circle replication primer and the rolling circle template must be associated together. In the disclosed methods, this association is already present in the reagent composition used in the amplification reaction. To get replication of the amplification target circles the reagent compositions typically are incubated under conditions that promote replication of the amplification target circles, wherein replication of the amplification target circles results in the formation of tandem sequence DNA. There are numerous variations of rolling circle amplification that can be used in the disclosed methods. Some useful variations of rolling circle amplification are described in, for example, U.S. Pat. Nos. 5,563,912, 6,143, 495, and 6,316,229. In some embodiments the tandem sequence DNA can itself be replicated or otherwise amplified.

In the disclosed method, the amplification or amplification products can be detected during the amplification reaction or operation. That is, the progress of amplification or amplification products can be detected in real-time. This can be accomplished in any suitable manner, but preferably involves the use of one or more fluorescent change probes and/or one or more fluorescent change primers.

C. Amplification Operation

The basic form of amplification operation is rolling circle replication of a circular DNA molecule (that is, a circularized open circle probe or an amplification target circle). Rolling circle amplification generally requires use of one or more rolling circle replication primers, which are complementary to the primer complement portions of the ATC, and a rolling circle DNA polymerase. For use in the disclosed methods, these components (along with a specific binding molecule) are pre-associated in a reagent composition. The DNA polymerase catalyzes primer extension and strand displacement in a processive rolling circle polymerization reaction that proceeds as long as desired, generating a large DNA molecule that contains a large number of tandem copies of a sequence complementary to the amplification target circle. Some forms of the disclosed method use additional rolling circle replication primers and secondary DNA strand displacement primers in the amplification reaction.

In multiply-primed RCA, one or more rolling circle replication primers anneal at various places on an amplification target circle to generate multiple replication forks. As each strand grows, the DNA polymerase encounters an adjacent replicating strand and displaces it from the amplification target circle. The result is multiple copies of each circle being produced simultaneously. Multiply-primed RCA can be performed using a single primer (which hybridizes to multiple sites on the amplification target circle) or multiple primers (each of which can hybridize to a single site on the amplification target circle or multiple sites on the amplification target circle). Multiple primers can be a part of the reagent composition or can be added for the amplification reaction. Multiple priming (as occurs in MPRCA) can increase the yield of amplified product from RCA. Primers anneal to multiple locations on the circular template and a product of extension by polymerase is initiated from each location. In this way, multiple extensions are achieved simultaneously from a single amplification target circle.

The amplification operation also can involve detection of amplification during the amplification operation (that is, real-time detection). This can be accomplished in any suitable manner. A particularly useful means of obtaining real-time detection is the use of fluorescent change probes and/or primers in the amplification operation. With suitably designed fluorescent change probes and primers, fluorescent signals can be generated as amplification proceeds. In most such cases, the fluorescent signals will be in proportion to the amount of amplification product and/or amount of target sequence or target molecule.

In the disclosed method, detection can be during rolling circle amplification and preferably is accomplished through the use of fluorescent changes probes and/or primers. For example, rolling circle replication primers and/or secondary DNA strand displacement primers can be fluorescent change primers. Alternatively or in addition, detection probes that are fluorescent change probes can be used.

As well as rolling circle replication, the amplification operation can include additional nucleic acid replication or amplification processes. For example, TS-DNA can itself be replicated to form secondary TS-DNA. This process is referred to as secondary DNA strand displacement. The combination of rolling circle replication and secondary DNA strand displacement is referred to as linear rolling circle amplification (LRCA). The secondary TS-DNA can itself be replicated to form tertiary TS-DNA in a process referred to as tertiary DNA strand displacement. Secondary and tertiary DNA strand displacement can be performed sequentially or simultaneously. When performed simultaneously, the result is strand displacement cascade amplification. The combination of rolling circle replication and strand displacement cascade amplification is referred to as exponential rolling circle amplification (ERCA). Secondary TS-DNA, tertiary TS-DNA, or both can be amplified by transcription. Exponential rolling circle amplification is a preferred form of amplification operation.

After RCA, a round of LM-RCA can be performed on the TS-DNA produced in the first RCA. This round of LM-RCA can be performed with an open circle probe, referred to as a secondary open circle probe, having target probe portions complementary to a target sequence in the TS-DNA produced in the first round. When such new rounds of LM-RCA are performed, the amplification is referred to as nested LM-RCA. Nested L,M-RCA can also be performed on ligated OCPs or ATCs that have not been amplified. In this case, LM-RCA can be carried out using either ATCs or target-dependent ligated OCPs. This is especially useful for in situ detection. For in situ detection, the first, unamplified OCP, which is topologically locked to its target sequence, can be subjected to nested LM-RCA. By not amplifying the first OCP, it can remain hybridized to the target sequence while LM-RCA amplifies a secondary OCP topologically locked to the first OCP. Nested,LM-RCA is described in U.S. Pat. No. 6,143,495.

When an open circle probe is used to form the amplification target circle, the amplification target circle can be formed by target-mediated ligation. Where OCPs are used, the tandem sequence DNA consists of alternating target sequence and spacer sequence. Note that the spacer sequence of the TS-DNA is the complement of the sequence between the left target probe and the right target probe in the original open circle probe.

1. DNA Strand Displacement

DNA strand displacement is one way to amplify TS-DNA. Secondary DNA strand displacement is accomplished by hybridizing secondary DNA strand displacement primers to TS-DNA and allowing a DNA polymerase to synthesize DNA from these primed sites (see FIG. 11 in U.S. Pat. No. 6,143,495). Because a complement of the secondary DNA strand displacement primer occurs in each repeat of the TS-DNA, secondary DNA strand displacement can result in a high level of amplification. The product of secondary DNA strand displacement is referred to as secondary tandem sequence DNA or TS-DNA-2. Secondary DNA strand displacement can be accomplished by performing RCA to produce TS-DNA, mixing secondary DNA strand displacement primer with the TS-DNA, and incubating under conditions promoting replication of the tandem sequence DNA.

Secondary DNA strand displacement can also be carried out simultaneously with rolling circle replication. This is accomplished by mixing secondary DNA strand displacement primer with the reaction prior to or during rolling circle replication. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. The generation of TS-DNA-2 and its release into solution by strand displacement is shown diagrammatically in FIG. 11 in U.S. Pat. No. 6,143,495. For simultaneous rolling circle replication and secondary DNA strand displacement, it is preferred that the rolling circle DNA polymerase be used for both replications. This allows optimum conditions to be used and results in displacement of other strands being synthesized downstream. Secondary DNA strand displacement can follow any DNA replication operation, such as RCA, LM-RCA or nested LM-RCA.

Generally, secondary DNA strand displacement can be performed by, simultaneous with or following RCA, mixing a secondary DNA strand displacement primer with the reaction mixture and incubating under conditions that promote both hybridization between the tandem sequence DNA and the secondary DNA strand displacement primer, and replication of the tandem sequence DNA, where replication of the tandem sequence DNA results in the formation of secondary tandem sequence DNA.

When secondary DNA strand displacement is carried out in the presence of a tertiary DNA strand displacement primer (or an equivalent primer), an exponential amplification of TS-DNA sequences takes place. This special and preferred mode of DNA strand displacement is referred to as strand displacement cascade amplification (SDCA) and is a form of exponential rolling circle amplification (ERCA). In SDCA, a secondary DNA strand displacement primer primes replication of TS-DNA to form TS-DNA-2, as described above. The tertiary DNA strand displacement primer strand can then hybridize to, and prime replication of, TS-DNA-2 to form TS-DNA-3. Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. This reaction amplifies DNA at an almost exponential rate. In a useful mode of SDCA, rolling circle replication primers can serve as the tertiary DNA strand displacement primer, thus eliminating the need for a separate primer. The additional forms of tandem sequence DNA beyond secondary tandem sequence DNA are collectively referred to herein as higher order tandem sequence DNA. Higher order tandem sequence DNA encompasses TS-DNA-3, TS-DNA-4, and any other tandem sequence DNA produced from replication of secondary tandem sequence DNA or the products of such replication.

For this mode, the rolling circle replication primer and/or tertiary DNA strand displacement primer should be used at a concentration sufficiently high to obtain rapid priming on the growing TS-DNA-2 strands. To optimize the efficiency of SDCA, it is preferred that a sufficient concentration of secondary DNA strand displacement primer and tertiary DNA strand displacement primer be used to obtain sufficiently rapid priming of the growing TS-DNA strand to out compete TS-DNA for binding to its complementary TS-DNA. Optimization of primer concentrations are described in U.S. Pat. No. 6,143,495 and can be aided by analysis of hybridization kinetics (Young and Anderson, "Quantitative analysis of solution hybridization" in *Nucleic Acid Hybridization: A Practical Approach* (IRL Press, 1985) pages 47-71).

Generally, strand displacement cascade amplification can be performed by, simultaneous with, or following, RCA, mixing a secondary DNA strand displacement primer and a tertiary DNA strand displacement primer with the reaction mixture and incubating under conditions that promote hybridization between the tandem sequence DNA and the secondary DNA strand displacement primer, replication of the tandem sequence DNA—where replication of the tandem sequence DNA results in the formation of secondary tandem sequence DNA—hybridization between the secondary tandem sequence DNA and the tertiary DNA strand displacement primer, and replication of secondary tandem sequence DNA—where replication of the secondary tandem sequence DNA results in formation of tertiary tandem sequence DNA (TS-DNA-3).

Secondary and tertiary DNA strand displacement can also be carried out sequentially. Following a first round of secondary DNA strand displacement, a tertiary DNA strand displacement primer can be mixed with the secondary tandem sequence DNA and incubated under conditions that promote hybridization between the secondary tandem sequence DNA and the tertiary DNA strand displacement primer, and replication of secondary tandem sequence DNA, where replication of the secondary tandem sequence DNA results in formation of tertiary tandem sequence DNA (TS-DNA-3). This round of strand displacement replication can be referred to as tertiary DNA strand displacement. However, all rounds of strand displacement replication following rolling circle replication can also be referred to collectively as DNA strand displacement or secondary DNA strand displacement.

A modified form of secondary DNA strand displacement results in amplification of TS-DNA and is referred to as opposite strand amplification (OSA). OSA is the same as secondary DNA strand displacement except that a special form of rolling circle replication primer is used that prevents it from hybridizing to TS-DNA-2. Opposite strand amplification is described in U.S. Pat. No. 6,143,495. Opposite strand amplification can be easily accomplished using the disclosed reagents compositions having the rolling circle replication primer attached to a specific binding molecule, there will be no free rolling circle replication primers to prime replication of TS-DNA-2.

The DNA generated by DNA strand displacement can be labeled and/or detected using the same labels, labeling methods, and detection methods described for use with TS-DNA. In the disclosed method, detection generally will be during DNA strand displacement and preferably is accomplished through the use of fluorescent changes probes and/or primers. For example, secondary DNA strand displacement primers and/or tertiary DNA strand displacement primers can be fluorescent change primers. Alternatively or in addition, detection probes that are fluorescent change probes can be used.

2. Geometric Rolling Circle Amplification

RCA reactions can be carried out with either linear or geometric kinetics (Lizardi et al., 1998). Linear rolling circle amplification generally follows linear kinetics. Two useful forms of RCA with geometric kinetics are exponential multiply-primed rolling circle amplification (EMPRCA) and exponential rolling circle amplification (ERCA). In exponential multiply-primed RCA. one or more rolling circle replication primers anneal at various places on the amplification target circle to generate multiple replication forks. As each strand grows, the DNA polymerase encounters an adjacent replicating strand and displaces it from the amplification target circle. The result is multiple copies of each circle being produced simultaneously. The replicated strands are referred to as tandem sequence DNA (TS-DNA). As each TS-DNA strand is displaced from the circular template, secondary DNA strand displacement primers can anneal to, and prime replication of, the TS-DNA. Replication of the TS-DNA forms complementary strands referred to as secondary tandem sequence DNA or TS-DNA-2. As a secondary TS-DNA strand is elongated, the DNA polymerase will run into the 5' end of the next growing strand of secondary TS-DNA and will displace its 5' end. In this fashion a tandem queue of elongating DNA polymerases is formed on the TS-DNA template. As long as the rolling circle reaction continues, new primers and new DNA polymerases are added to TS-DNA at the growing end of the rolling circle.

Random or degenerate primers can be used to perform multiply-primed RCA. Such random or degenerate primers will anneal to multiple sites on the amplification target circle (resulting in production of tandem sequence DNA), as well as to multiple sites on the tandem sequence DNA (resulting in production of secondary tandem sequence DNA). The random primers can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with the primers. This can result in another round of replication resulting in TS-DNA-4 (which is equivalent to TS-DNA-2). TS-DNA-4, in turn, becomes a template for DNA replication primed by random primers. The cascade continues this manner until the reaction stops or reagents become limiting. Multiply-primed RCA is particularly useful for amplifying larger circular templates such as amplification target circles that are, or are derived from or include, nucleic acid molecules of interest. Multiply-primed RCA is described in Dean et al., Rapid Amplification of Plasmid and Phage DNA Using Phi29 DNA Polymerase and Multiply-Primed Rolling Circle Amplification, Genome Research 11:1095-1099 (2001).

Exponential multiply-primed RCA also can be achieved using specific rolling circle replication primers, secondary DNA strand displacement primers and tertiary DNA strand displacement primers. In this form of the disclosed method, rolling circle replication is primed from multiple specific primer complement portions of the circular template. As the strand grows, the DNA polymerase encounters 5' end of the strand and displaces it from the circular template. A secondary DNA strand displacement primer primes replication of TS-DNA to form a complementary strand referred to as secondary tandem sequence DNA or TS-DNA-2. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. A tertiary DNA strand displacement primer strand (which is complementary to the TS-DNA-2 strand and which can be the rolling circle replication primer) can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. In one mode of ERCA, a rolling circle replication primer serves as the tertiary DNA strand displacement primer, thus eliminating the need for a separate primer. Exponential RCA and other useful forms of RCA are described in U.S. Pat. Nos. 5,854,033, and 6,143,495.

D. Detection of Amplification Products

Products of the amplification operation can be detected using any nucleic acid detection technique. For real-time detection, the amplification products and the progress of amplification are detected during the amplification operation. Real-time detection is usefully accomplished using one or more or one or a combination of fluorescent change probes and fluorescent change primers. Other detection techniques can be used, either alone or in combination with real-timer detection and/or detection involving fluorescent change probes and primers. Many techniques are known for detecting nucleic acids. The nucleotide sequence of the amplified sequences also can be determined using any suitable technique.

1. Primary Labeling

Primary labeling consists of incorporating labeled moieties, such as fluorescent nucleotides, biotinylated nucleotides, digoxygenin-containing nucleotides, or bromodeoxyuridine, during rolling circle replication in RCA, or during transcription in RCT. For example, fluorescent labels can be incorporated into replicated nucleic acid by using fluorescently labeled primers, such as fluorescent change rolling circle replication primers. In another example, one can incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

A useful form of primary labeling is the use of fluorescent change primers in the amplification operation. Fluorescent change primers exhibit a change in fluorescence intensity or wavelength based on a change in the form or conformation of the primer and the amplified nucleic acid. Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers and scorpion primers.

Cleavage activated primers are primers where fluorescence is increased by cleavage of the primer. Generally, cleavage activated primers are incorporated into replicated strands and are then subsequently cleaved. Cleavage activated primers can include a fluorescent label and a quenching moiety in proximity such that fluorescence from the label is quenched. When the primer is clipped or digested (typically by the 5'-3' exonuclease activity of a polymerase during amplification), the quenching moiety is no longer in proximity to the fluorescent label and fluorescence increases. Little et al., Clin. Chem. 45:777-784 (1999), describe the use of cleavage activated primers.

2. Secondary Labeling

Secondary labeling consists of using suitable molecular probes, such as detection probes, to detect the amplified nucleic acids. For example, an amplification target circle may be designed to contain several repeats of a known arbitrary sequence, referred to as detection tags. The detection probes can then be hybridized to these detection tags. The detection probes may be labeled as described above with, for example, an enzyme, fluorescent moieties, or radioactive isotopes. By using three detection tags per amplification target circle, and four fluorescent moieties per each detection probe, one may obtain a total of twelve fluorescent signals for every amplification target circle repeat in the TS-DNA, yielding a total of 12,000 fluorescent moieties for every amplification target circle that is amplified by RCA. Detection probes can interact by hybridization or annealing via normal Watson-Crick base-pairing (or related alternatives) or can interact with double-stranded targets to form a triple helix. Such triplex-forming detection probes can be used in the same manner as other detection probes, such as in the form of fluorescent change probes.

A useful form of secondary labeling is the use of fluorescent change probes and primers in or following the amplification operation. Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during or following amplification), the quenching moiety is no longer in proximity to the fluorescent label and fluorescence increases. TaqMan probes are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during or after amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes. Stem quenched primers (such as peptide nucleic acid quenched primers and hairpin quenched primers) can be used as secondary labels.

3. Multiplexing and Hybridization Array Detection

RCA is easily multiplexed by using sets of different reagent compositions (having different amplification target circles), each reagent composition being associated with, for example, different target molecules, target sequences, and/or array positions. Each amplification target circle can have a different primer complement portions and/or different detection tag portions corresponding to different rolling circle replication primers and/or different detection probes. Use of different fluorescent labels with different rolling circle replication primers and/or different detection probes allows specific detection of different open circle probes (and thus, of different targets).

For multiplexing, the mixture of reagent composition(s) (having amplification target circle(s)), rolling circle replication primer(s) and fluorescent change probe(s) in the disclosed method can comprise a plurality of reagent compositions. The fluorescent change probes each can comprise a complementary portion, the amplification target circles each can comprise at least one detection tag portion, and the complementary portion of each of the fluorescent change probes matches the sequence of one or more of the detection tag portions of the amplification target circles. The mixture can comprise a plurality of fluorescent change probes, where the complementary portion of each fluorescent change probe matches the sequence of one or more of the detection tag portions of a different one of the amplification target circles. The mixture can comprise a plurality of fluorescent change probes, where the complementary portion of each fluorescent change probe matches the sequence of one or more of the detection tag portions of one or more of the amplification target circles. The mixture can comprise a plurality of fluorescent change probes, where the complementary portion of each fluorescent change probe matches the sequence of one of the detection tag portions of a different one of the amplification target circles. The mixture can comprise a plurality of fluorescent change probes, where the complementary portion of each fluorescent change probe matches the sequence of a plurality of the detection tag portions of a different one of the amplification target circles. The mixture can comprise a plurality of fluorescent change probes, where the complementary portion of each fluorescent change probe matches the sequence of a plurality of the detection tag portions of one of the amplification target circles. The mixture can comprise a plurality of fluorescent change probes, where the complementary portion of each fluorescent change probe matches the sequence of a plurality of the detection tag portions of a plurality of the amplification target circles. The mixture can comprise a plurality of fluorescent change probes, where the complementary portion of each fluorescent change probe matches the sequence of one of the detection tag portions of a plurality of the amplification target circles. The mixture can comprise a plurality of fluorescent change probes, where the complementary portion of each fluorescent change probe matches the sequence of one of the detection tag portions of one of the amplification target circles.

RCA can also be multiplexed by using sets of different open circle probes, each open circle probe carrying different target probe sequences designed for binding to unique targets and each open circle probe having a different primer complement portions and/or different detection tag portions corresponding to different rolling circle replication primers and/or different detection probes. Only those open circle probes that are able to find their targets will give rise to TS-DNA. Use of different fluorescent labels with different rolling circle replication primers and/or different detection probes allows specific detection of different open circle probes (and thus, of different targets).

The TS-DNA molecules generated by RCA are of high molecular weight and low complexity; the complexity being the length of the amplification target circle. There several ways to capture a given TS-DNA to a fixed position in a solid-state detector. One is to include within the amplification target circles a unique address tag sequence for each unique amplification target circle. TS-DNA generated from a given amplification target circle will then contain sequences corresponding to a specific address tag sequence. Another way to capture TS-DNA when open circle probes are used is to use the target sequence present on the TS-DNA as the address tag.

4. Detecting Multiple Reagent Compositions

Multiplex RCA assays are useful for detecting multiple reagent compositions (via detection of multiple amplification target circles). A single RCA assay can be used to detect the presence of one or more members of a group of any number of amplification target circles (and, thus, any number of corresponding target sequences or target molecules). By associating different amplification target circles with different target molecules (by associating the reagent compositions containing the amplification target circles with the target molecules), each different target molecule can be detected by differential detection of the various amplification target circles. This can be accomplished, for example, by designing an amplification target circle for each target molecule, where the detection tag portions and/or the primer complement portions of each amplification target circle are different. Amplification of the different ATCs can be detected based on different primer complement portion sequences by using, for example, rolling circle replication primers that are fluorescent change primers. Alternatively, the different amplification target circles can be detected based on different detection tag sequences by using, for example, detection probes that are fluorescent change probes. In this case, the primer portions of all the amplification target circles can be the same. Use of different detection tag sequences and different detection probes also allows differential detection of amplification target circles even when random or degenerate primers are used for multiply-primed RCA. Different detection probes can be used to detect the various TS-DNAs (each having specific detection tag sequences).

By associating different amplification target circles with different target molecules, such as proteins (by associating the reagent compositions containing the amplification target circles with the proteins of interest), each different target molecule can be detected by differential detection of the various target molecules. This can be accomplished, for example, by designing amplification target circles having deferent detection tag portions. Since the detection tag portions are different, amplification of the different ATCs can be detected (using, for example, rolling circle replication primers that are fluorescent change primers).

5. Combinatorial Multicolor Coding

One form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided. Combinatorial labeling can be used with fluorescent change probes and primers.

The combinations of labels establish a code for identifying different detection probes and, by extension, different target molecules to which those detection probes are associated with. This labeling scheme is referred to as Combinatorial Multicolor Coding (CMC). Such coding is described by Speicher et al., *Nature Genetics* 12:368-375 (1996). Use of CMC in connection with rolling circle amplification is described in U.S. Pat. No. 6,143,495. Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, 5 labels form 31 label combinations, and 6 labels forms 63 label combinations.

For combinatorial multicolor coding, a group of different detection probes are used as a set. Each type of detection probe in the set is labeled with a specific and unique combination of fluorescent labels. For those detection probes assigned multiple labels, the labeling can be accomplished by labeling each detection probe molecule with all of the required labels. Alternatively, pools of detection probes of a given type can each be labeled with one of the required labels. By combining the pools, the detection probes will, as a group, contain the combination of labels required for that type of detection probe. Where each detection probe is labeled with a single label, label combinations can also be generated by using OCPs or ATCs with coded combinations of detection tags complementary to the different detection probes. In this scheme, the OCPs or ATCs will contain a combination of detection tags representing the combination of labels required for a specific label code. Further illustrations are described in U.S. Pat. No. 6,143,495. Use of pools of detection probes each probe with a single label is preferred when fluorescent change probes are used.

Speicher et al. describes a set of fluors and corresponding optical filters spaced across the spectral interval 350-770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3-10 (1989), Mujumdar et al., *Cytometry* 10:11-19 (1989), Yu, *Nucleic Acids Res.* 22:3226-3232 (1994), and Waggoner, *Meth. Enzymology* 246:362-373 (1995). These fluors can all be excited with a 75W Xenon arc.

To attain selectivity, filters with bandwidths in the range of 5 to 16 nm are preferred. To increase signal discrimination; the fluors can be both excited and detected at wavelengths far from their spectral maxima. Emission bandwidths can be made as wide as possible. For low-noise detectors, such as cooled CCD cameras, restricting the excitation bandwidth has little effect on attainable signal to noise ratios. A list of preferred filters for use with the preferred fluor set is listed in Table 1 of Speicher et al. It is important to prevent infra-red light emitted by the arc lamp from reaching the detector; CCD chips are extremely sensitive in this region. For this purpose, appropriate IR blocking filters can be inserted in the image path immediately in front of the CCD window to minimize loss of image quality. Image analysis software can then be used to count and analyze the spectral signatures of fluorescent dots.

E. Transcription

Once TS-DNA is generated using RCA, further amplification can be accomplished by transcribing the TS-DNA from promoters embedded in the TS-DNA. This combined process, referred to as rolling circle replication with transcription (RCT) requires that the amplification target circle from which the TS-DNA is made have a promoter portion. The promoter portion is then amplified along with the rest of the amplification target circle resulting in a promoter embedded in each tandem repeat of the TS-DNA. Because transcription, like rolling circle amplification, is a process that can go on continuously (with re-initiation), multiple transcripts can be produced from each of the multiple promoters present in the TS-DNA. RCT effectively adds another level of amplification of amplification target circles. RCT is further described in U.S. Pat. No. 6,143,495. Amplification target circles can also be directly transcribed (that is, not in conjunction with rolling circle amplification). The amplified product will be RNA. Transcription of amplification target circles can produce a long tandem repeat transcript if the amplification target circle does not have a transcription termination sequence.

The transcripts generated in RCT or direct transcription can be labeled and/or detected using the same labels, labeling methods, and detection methods described for use with TS-DNA. Most of these labels and methods are adaptable for use with nucleic acids in general. A useful method of labeling RCT transcripts is by direct labeling of the transcripts by incorporation of labeled nucleotides, most preferably biotinylated nucleotides, during transcription. RCT transcripts can also be detected in real-time, using, for example, fluorescent change probes.

F. Ligation Operation

If an open circle probe is used in or with the disclosed method, a ligation operation will be used to circularize the open circle probe (and thus form an amplification target circle). An open circle probe, optionally in the presence of one or more gap oligonucleotides, can be incubated with a sample containing nucleic acids, under suitable hybridization conditions, and then ligated to form a covalently closed circle. The ligated open circle probe is a form of amplification target circle. This operation is similar to ligation of padlock probes described by Nilsson et al., *Science,* 265:2085-2088 (1994). The ligation operation allows subsequent amplification to be dependent on the presence of a target sequence. Suitable ligases for the ligation operation are described above. Ligation conditions are generally known. Most ligases require $Mg^{++}$. There are two main types of ligases, those that are ATP-dependent and those that are NAD-dependent. ATP or NAD, depending on the type of ligase, should be present during ligation.

The target sequence for an open circle probe can be any nucleic acid or other compound to which the target probe portions of the open circle probe can hybridize in the proper alignment. Target sequences can be found in any nucleic acid molecule from any nucleic acid sample. Thus, target sequences can be in nucleic acids in cell or tissue samples, reactions, and assays. Target sequences can also be artificial nucleic acids (or other compounds to which the target probe portions of the open circle probe can hybridize in the proper alignment). For example, nucleic acid tags can be associated with various of the disclosed compounds to be detected using open circle probes. Thus, a reporter binding agent can contain a target sequence to which an open circle probe can hybridize. In these cases, the target sequence provides a link between the target molecule being detected and the amplification of signal mediated by the open circle probe.

When RNA is to be detected, it is preferred that a reverse transcription operation be performed to make a DNA target sequence. Alternatively, an RNA target sequence can be detected directly by using a ligase that can perform ligation on a DNA:RNA hybrid substrate. A preferred ligase for this is T4 DNA ligase.

G. Gap-Filling Ligation

The gap space formed by an OCP hybridized to a target sequence is normally occupied by one or more gap oligonucleotides as described above. Such a gap space may also be filled in by a gap-filling DNA polymerase during the ligation operation. As an alternative, the gap space can be partially bridged by one or more gap oligonucleotides, with the remainder of the gap filled using DNA polymerase. This modified ligation operation is referred to herein as gap-filling ligation and is a preferred form of the ligation operation. The principles and procedure for gap-filling ligation are generally analogous to the filling and ligation performed in gap LCR (Wiedmann et al., *PCR Methods and Applications* (Cold Spring Harbor Laboratory Press, Cold Spring Harbor Laboratory, NY, 1994) pages S51-S64; Abravaya et al., *Nucleic Acids Res.,* 23(4):675-682 (1995); European Patent Application EP0439182 (1991)). In the case of LM-RCA, the gap-filling ligation operation is substituted for the normal ligation operation. Gap-filling ligation provides a means for discriminating between closely related target sequences. Gap-filling ligation can be accomplished by using a different DNA polymerase, referred to herein as a gap-filling DNA polymerase. Suitable gap-filling DNA polymerases are described above. Alternatively, DNA polymerases in general can be used to fill the gap when a stop base is used. The use of stop bases in the gap-filling operation of LCR is described in European Patent Application EP0439182. The principles of the design of gaps and the ends of flanking probes to be joined, as described in EP0439182, is generally applicable to the design of the gap spaces and the ends of target probe portions described herein. Gap-filling ligation is further described in U.S. Pat. No. 6,143,495.

H. Target Fingerprint Analysis

The disclosed method can be used to produce information that serves as a target fingerprint of a target sample. Such a target fingerprint can be used for any purpose, including, for example, comparison with target molecules in other target fingerprints. Similarly prepared target fingerprints of other target samples allow convenient detection of differences between the samples. The target fingerprints can be used both for detection of related target samples and comparison of target samples. For example, the presence or identity of specific organisms can be detected by producing a target fingerprint of the test organism and comparing the resulting target fingerprint with reference target fingerprints prepared from known organisms. Changes and differences in expression patterns can also be detected by preparing target fingerprints from different cell samples and comparing the target fingerprints.

Informational content of, or derived from, target fingerprints can be stored. Such information can be stored, for example, in or as computer readable media. Target fingerprints can contain or be made up of other information derived from the information generated in the disclosed method, and can be combined with information obtained or generated from any other source. The informational nature of target fingerprints produced using the disclosed method lends itself to combination and/or analysis using known bioinformatics systems and methods.

Target fingerprints of nucleic acid samples can be compared to a similar target fingerprint derived from any other sample to detect similarities and differences in the samples (which is indicative of similarities and differences in the target molecules in the samples). For example, a target fingerprint of a first nucleic acid sample can be compared to a target fingerprint of a sample from the same type of organism as the first target sample, a sample from the same type of tissue as the first target sample, a sample from the same organism as the first target sample, a sample obtained from the same source but at time different from that of the first target sample, a sample from an organism different from that of the first target sample, a sample from a type of tissue different from that of the first target sample, a sample from a strain of organism different from that of the first target sample, a sample from a species of organism different from that of the first target sample, or a sample from a type of organism different from that of the first target sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or E. coli and Salmonella. A different type of tissue refers to tissues of different types such as liver and kidney, or skin and brain. A different strain or species of organism refers to organisms differing in their species or strain designation as those terms are understood in the art.

I. Specific Embodiments

Disclosed are compositions comprising a reporter binding agent, an amplification target circle, and DNA polymerase; wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are compositions comprising one or more reporter binding agents, one or more amplification target circles, and one or more DNA polymerases; wherein the reporter binding agents each comprise one or more specific binding molecules and one or more rolling circle replication primers, wherein the specific binding molecule each are specific for a target molecule, wherein the specific binding molecules are not bound to the target molecule, and wherein the composition does not comprise tandem sequence DNA.

Also disclosed are compositions comprising a reporter binding agent, an amplification target circle, and DNA polymerase; wherein the reporter binding agent comprises a specific binding molecule and a rolling circle replication primer, wherein the specific binding molecule is specific for a target molecule, wherein the composition is stored separate from the target molecule, and wherein the composition does not comprise tandem sequence DNA.

Also disclosed are compositions comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, wherein the composition is stored separate from the target, and wherein the composition does not comprise tandem sequence DNA.

Also disclosed are compositions comprising a reporter binding agent, an amplification target circle, and DNA polymerase; wherein the reporter binding agent comprises a specific binding molecule and a rolling circle replication primer, wherein the specific binding molecule is specific for a target molecule, and wherein the specific binding molecule is not bound to the target molecule.

Also disclosed are compositions comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, and wherein the specific binding molecules are not bound to the target molecule.

Also disclosed are compositions comprising a reporter binding agent, an amplification target circle, and DNA polymerase; wherein the reporter binding agent comprises a specific binding molecule and a rolling circle replication primer, wherein the specific binding molecule is specific for a target molecule, and wherein the composition is stored separate from the target molecule.

Also disclosed are compositions comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, and wherein the composition is stored separate from the target.

Also disclosed are compositions comprising a reporter binding agent, an amplification target circle, and DNA polymerase; wherein the reporter binding agent comprises a specific binding molecule and a rolling circle replication primer, wherein the specific binding molecule is specific for a target molecule, and wherein the composition is stored separate from the target molecule for at least one hour, at least two hours, at least three hours, or at least one day.

Also disclosed are compositions comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, and wherein the composition is stored separate from the target molecule for at least one hour, at least two hours, at least three hours, or at least one day.

Also disclosed are compositions consisting essentially of a reporter binding agent, an amplification target circle, and DNA polymerase; wherein the reporter binding agent comprises a specific binding molecule and a rolling circle replication primer.

Also disclosed are compositions consisting essentially of one or more reporter binding agents, one or more amplification target circles, and one or more DNA polymerases; wherein the reporter binding agents each comprise one or more specific binding molecules and one or more rolling circle replication primers.

Also disclosed are compositions consisting essentially of a reporter binding agent, an amplification target circle, and DNA polymerase; wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are compositions consisting essentially of one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, wherein the specific binding molecules are not bound to the target molecule, and wherein the composition does not comprise tandem sequence DNA.

The disclosed compositions can have a variety of forms. For example, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer.

In some forms of the disclosed compositions, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed compositions, the composition can be stored at or below about 25° C. The composition can be stored at or below about 4° C. The composition can be stored at or below about −20° C. The composition can be stored at or below about −70° C. The composition can be stored at or below room temperature. The DNA polymerase can be φ29 DNA polymerase. The composition can further comprise glycerol. The composition can further comprise from about 20% glycerol to about 50% glycerol. The amplification target circle can comprise a single-stranded, circular DNA molecule comprising a primer complement portion, wherein the primer complement portion can be complementary to the rolling circle replication primer.

Disclosed are methods of making a composition for rolling circle amplification, where the method comprises annealing an amplification target circle to a rolling circle replication primer, wherein a reporter binding agent comprises the rolling circle replication primer and a specific binding molecule, and incubating the reporter binding agent and amplification target circle with DNA polymerase, wherein the specific binding molecule is specific for a target molecule, wherein the specific binding molecule is not bound to the target molecule, and wherein the composition does not comprise tandem sequence DNA.

Also disclosed are methods of making a composition for rolling circle amplification, where the method comprises incubating an amplification target circle and a rolling circle replication primer under conditions that promote association of the amplification target circle with the rolling circle replication primer, wherein a reporter binding agent comprises the rolling circle replication primer and a specific binding molecule, and incubating the reporter binding agent and amplification target circle with DNA polymerase under conditions that promote association of the DNA polymerase with the reporter binding agent, wherein the specific binding molecule is specific for a target molecule, wherein the specific binding molecule is not bound to the target molecule, and wherein the composition does not comprise tandem sequence DNA.

The disclosed methods can have a variety of forms. For example, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer. The reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same.

In some forms of the disclosed methods, the rolling circle replication primers can be different. The amplification target circles can be associated with a plurality of the rolling circle replication primers, and the amplification target circles can be different. An amplification target circle can be associated with each of the rolling circle replication primers, and a different amplification target circle is associated with each different rolling circle replication primer. The reporter binding agent can comprise three or more rolling circle replication primers. The reporter binding agent can comprise two or three rolling circle replication primers.

In some forms, the disclosed methods can further comprise storing the composition at or below about 25° C. The method can further comprise storing the composition at or below about 4° C. The composition can be stored at or below about −20° C. The method can further comprise storing the composition at or below about −70° C. The composition can be stored at or below room temperature. The amplification target circle can be annealed to the rolling circle replication primer in the presence of from about 50 mM to about 150 mM salt. The concentration of reporter binding agent during annealing of the amplification target circle and the rolling circle replication primer can be about 50 nM or higher. The concentration of the amplification target circle during annealing can be from about 1 to about 3 times the concentration the reporter binding agent.

In some forms of the disclosed methods, the amplification target circle can be annealed to the rolling circle replication primer for from about 20 minutes to about 60 minutes at from about 35° C. to about 40° C. The amplification target circle can be annealed to the rolling circle replication primer for from about 30 minutes to about 45 minutes at about 37° C. The reporter binding agent and amplification target circle can be incubated with the DNA polymerase substantially in the absence of $Mg^{2+}$. The concentration of the DNA polymerase during incubation can be from about 2 to about 6 times the concentration the amplification target circle. The concentration of the DNA polymerase during incubation can be from about 3 to about 5 times the concentration the rolling circle replication primer. The reporter binding agent and amplification target circle can be incubated with the DNA polymerase for from about 10 minutes to about 20 minutes at from about 30° C. to about 34° C. The reporter binding agent and amplification target circle can be incubated with the DNA polymerase for about 15 minutes at about 31° C. The reporter binding agent and amplification target circle can be incubated with the DNA polymerase at from about 25° C. to about 33° C. The reporter binding agent and amplification target circle can be incubated with the DNA polymerase at about 3 1° C. The DNA polymerase can be 100 29 DNA polymerase. The composition can further comprise glycerol. The composition can further comprise from about 20% glycerol to about 50% glycerol.

In some forms of the disclosed methods, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer.

In some forms of the disclosed methods, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed methods, the composition can be stored at or below about 25° C. The composition can be stored at or below about 4° C. The composition can be stored at or below about −20° C. The composition can be stored at or below about −70° C. The composition can be stored at or below room temperature. The DNA polymerase can be 100 29 DNA polymerase. The composition can further comprise glycerol. The composition can further comprise from about 20% glycerol to about 50% glycerol. The amplification target circle can comprise a single-stranded, circular DNA molecule comprising a primer complement portion, wherein the primer complement portion can be complementary to the rolling circle replication primer.

Disclosed are methods comprising labeling a molecule of interest; wherein the molecule of interest is labeled by associating a target molecule with the molecule of interest, associating a composition with the target molecule, and generating a signal by performing rolling circle amplification of the composition, wherein the composition comprises a reporter binding agent, an amplification target circle, and DNA polymerase, wherein the reporter binding agent comprises a specific binding molecule and a rolling circle replication primer, wherein the specific binding molecule is specific for the target molecule, wherein the specific binding molecule is not bound to the target molecule prior to association of the composition with the target molecule, and wherein the composition does not comprise tandem sequence DNA prior to association of the composition with the target molecule.

Also disclosed are methods of labeling a molecule of interest, the method comprising associating a target molecule with the molecule of interest, associating a composition with the target molecule, and generating a signal by performing rolling circle amplification of the composition; wherein the composition comprises a reporter binding agent, an amplification target circle, and DNA polymerase, wherein the reporter binding agent comprises a specific binding molecule and a rolling circle replication primer, wherein the specific binding molecule is specific for the target molecule, wherein the specific binding molecule is not bound to the target molecule prior to association of the composition with the target molecule, and wherein the composition does not comprise tandem sequence DNA prior to association of the composition with the target molecule.

The disclosed methods can have a variety of forms. For example, following associating the target molecule with the molecule of interest, the molecule of interest can be separated from other molecules. Following associating the composition with the target molecule, the target molecule can be separated from other molecules. A sample can comprise the molecule of interest, wherein, following associating the target molecule with the molecule of interest, the molecule of interest can be separated from other molecules in the sample. The target molecule can comprise biotin, the specific binding molecule can comprise an antibody, and the antibody can be an antibody specific for biotin. The specific binding molecule can comprise an antibody, the target molecule can comprise a second antibody, the second antibody can be an animal immunoglobulin, and the antibody of the reporter binding agent can be specific for immunoglobulins from the same type of animal of which the second antibody is an immunoglobulin. The antibody of the reporter binding agent can be specific for the allotype corresponding to the second antibody. The antibody of the reporter binding agent can be specific for the isotype corresponding to the second antibody.

In some forms of the disclosed methods, the target molecule can be coupled to a second specific binding molecule. The second specific binding molecule can be specific for the molecule of interest. The second specific binding molecule can be specific for a second target molecule, and the second target molecule can be associated with the molecule of interest. The molecule of interest can comprise a peptide, protein, lipid, carbohydrate, complex carbohydrate, proteolipid, antibody, membrane fragment, nucleic acid, cofactor, metabolite, enzyme substrate, metal ion, or metal chelate.

In some forms of the disclosed methods, the molecule of interest can be associated with a solid support. The solid support can comprise acrylamide, agarose, cellulose, nitrocellulose, glass, gold, polystyrene, polyethylene vinyl acetate, polypropylene, polymethacrylate, polyethylene, polyethylene oxide, polysilicate, polycarbonate, teflon, fluorocarbon, nylon, silicon rubber, polyanhydride, polyglycolic acid, polylactic acid, polyorthoester, functionalized silane, polypropylfumerate, collagen, glycosaminoglycan, polyamino acid, or a combination. The solid support can comprise a thin film, membrane, bead, bottle, dish, fiber, optical fiber, woven fiber, chip, compact disk, shaped polymer, particle, microparticle, or a combination.

In some forms of the disclosed methods, the solid support can comprise a plurality of molecules of interest. Each molecule of interest can be immobilized on the solid support in a different predefined region of the solid support. The distance between the different predefined regions of the solid support can be fixed. The solid support can comprise thin film, membrane, bead, bottle, dish, fiber, optical fiber, woven fiber, chip, compact disk, shaped polymer, particle, microparticle, or a combination. The distance between at least two of the different predefined regions of the solid support can be variable. The molecules of interest can be immobilized to the solid support at a density exceeding 400 different molecules of interest per cubic centimeter. The solid support can comprise at least 1,000 different molecules of interest immobilized on the solid support. The solid support can comprise at least 10,000 different molecules of interest immobilized on the solid support. The solid support can comprise at least 100,000 different molecules of interest immobilized on the solid support. The solid support can comprise at least 1,000,000 different molecules of interest immobilized on the solid support. Each of the different predefined regions can be physically separated from each other of the different regions. The solid support can comprise a plurality of beads, microparticles, or a combination. The solid support can comprise thin film, membrane, bead, bottle, dish, fiber, optical fiber, woven fiber, chip, compact disk, shaped polymer, particle, microparticle, or a combination.

In some forms of the disclosed methods, the solid support can comprise acrylamide, agarose, cellulose, nitrocellulose, glass, gold, polystyrene, polyethylene vinyl acetate, polypropylene, polymethacrylate, polyethylene, polyethylene oxide, polysilicate, polycarbonate, teflon, fluorocarbon, nylon, silicon rubber, polyanhydride, polyglycolic acid, polylactic acid, polyorthoester, functionalized silane, polypropylfumerate, collagen, glycosaminoglycan, polyamino acid, or a combination. The solid support can be porous. The molecules of interest in the different predefined regions can be at least 20% pure. The molecules of interest in the different predefined regions can be at least 50% pure. The molecules of interest in the different predefined regions can be at least 80% pure. The molecules of interest in the different predefined regions can be at least 90% pure. Following associating the molecule of interest with the solid support, the molecule of interest can be separated from other molecules. A sample can comprise the molecule of interest, wherein, following associating the molecule of interest with the solid support, the molecule of interest can be separated from other molecules in the sample.

In some forms of the disclosed methods, the molecule of interest can comprise a protein of interest. The protein of interest can be immobilized on a solid support. The protein of interest can be immobilized on a solid support prior to associating the composition with the target molecule. The target molecule can be associated with the molecule of interest prior to immobilizing the protein of interest on the solid support. The target molecule can be associated with the molecule of interest after the protein of interest is immobilized on the solid support. The protein of interest can be immobilized on a solid support prior to associating the target molecule with the molecule of interest. A plurality of other proteins can be immobilized on the solid support.

In some forms of the disclosed methods, one or more other compositions can be associated with target molecules associated with one or more of the other proteins, wherein one or more other signals can be generated by performing rolling circle amplification of one or more of the other compositions, wherein the other compositions each can comprise a reporter binding agent, an amplification target circle, and DNA polymerase, wherein the reporter binding agent can comprise a specific binding molecule and a rolling circle replication primer, wherein the specific binding molecule can be specific for the target molecule, wherein the specific binding molecule need not be bound to the target molecule prior to association of the composition with the target molecule, and wherein the composition does not comprise tandem sequence DNA prior to association of the composition with the target molecule. The target molecules all can be the same. The target molecules can all different. At least two of the target molecules all can be different. The protein of interest can comprise a cell surface marker. The cell surface marker can be on a cell. The cell can be immobilized on a solid support. The cell can be separated from other cells by fluorescent activated cell sorting, wherein rolling circle amplification can result in an amplification product comprising a fluorescent label, wherein the fluorescent activated cell sorting can be accomplished using the fluorescent label of the amplification product. The cell can be separated from other cells, counted, or both, by flow cytometry.

In some forms of the disclosed methods, rolling circle amplification can result in an amplification product comprising a fluorescent label. A bead can comprise the fluorescent label, wherein the molecule of interest can be separated from other molecules by fluorescent activated cell sorting, wherein the fluorescent activated cell sorting can be accomplished using the fluorescent label of the bead. The molecule of interest can be separated from other molecules, counted, or both, by flow cytometry. A bead can comprise the fluorescent label. The association of the composition with the target molecule can be performed as part of or in conjunction with a cytometric bead assay, immuno-histochemistry, flow cytometry, immuno-fluorescence microscopy, in situ hybridization, fluorescence in situ hybridization, multiparametric fluorescence in situ hybridization, or a combination.

Disclosed are methods comprising labeling a target molecule; wherein the target molecule is labeled by associating a composition with the target molecule, and generating a signal by performing rolling circle amplification of the composition, wherein the composition comprises a reporter binding agent, an amplification target circle, and DNA polymerase, wherein the reporter binding agent comprises a specific binding molecule and a rolling circle replication primer, wherein the specific binding molecule is specific for the target molecule, wherein the specific binding molecule is not bound to the target molecule prior to association of the composition with the target molecule, and wherein the composition does not comprise tandem sequence DNA prior to association of the composition with the target molecule.

Also disclosed are methods of labeling a target molecule, the method comprising associating a composition with the target molecule, and generating a signal by performing rolling circle amplification of the composition; wherein the composition comprises a reporter binding agent, an amplification target circle, and DNA polymerase, wherein the reporter binding agent comprises a specific binding molecule and a rolling circle replication primer, wherein the specific binding molecule is specific for the target molecule, wherein the specific binding molecule is not bound to the target molecule prior to association of the composition with the target molecule, and wherein the composition does not comprise tandem sequence DNA prior to association of the composition with the target molecule.

In some forms of the disclosed methods, following associating the composition with the target molecule, the target molecule can be separated from other molecules. A sample can comprise the target molecule, wherein, following associating the composition with the target molecule, the target molecule can be separated from other molecules in the sample. The target molecule can comprise a peptide, protein, lipid, carbohydrate, complex carbohydrate, proteolipid, antibody, membrane fragment, nucleic acid, cofactor, metabolite, enzyme substrate, metal ion, or metal chelate. The target molecule can be associated with a solid support. The solid support can comprise acrylamide, agarose, cellulose, nitrocellulose, glass, gold, polystyrene, polyethylene vinyl acetate, polypropylene, polymethacrylate, polyethylene, polyethylene oxide, polysilicate, polycarbonate, teflon, fluorocarbon, nylon, silicon rubber, polyanhydride, polyglycolic acid, polylactic acid, polyorthoester, functionalized silane, polypropylfumerate, collagen, glycosaminoglycan, polyamino acid, or a combination.

In some forms of the disclosed methods, the solid support can comprise a plurality of target molecules. Each target molecule can be immobilized on the solid support in a different predefined region of the solid support. The distance between the different predefined regions of the solid support can be fixed. The solid support can comprise thin film, membrane, bead, bottle, dish, fiber, optical fiber, woven fiber, chip, compact disk, shaped polymer, particle, microparticle, or a combination. The distance between at least two of the different predefined regions of the solid support can be variable. The target molecules can be immobilized to the solid support at a density exceeding 400 different target molecules per cubic centimeter. The solid support can comprise at least 1,000 different target molecules immobilized on the solid support. The solid support can comprise at least 10,000 different target molecules immobilized on the solid support. The solid support can comprise at least 100,000 different target molecules immobilized on the solid support. The solid support can comprise at least 1,000,000 different target molecules immobilized on the solid support.

In some forms of the disclosed methods, each of the different predefined regions can be physically separated from each other of the different regions. The solid support can comprise a plurality of beads, microparticles, or a combination. The solid support can comprise thin film, membrane, bead, bottle, dish, fiber, optical fiber, woven fiber, chip, compact disk, shaped polymer, particle, microparticle, or a combination. The solid support can comprise acrylamide, agarose, cellulose, nitrocellulose, glass, gold, polystyrene, polyethylene vinyl acetate, polypropylene, polymethacrylate, polyethylene, polyethylene oxide, polysilicate, polycarbonate, teflon, fluorocarbon, nylon, silicon rubber, polyanhydride, polyglycolic acid, polylactic acid, polyorthoester, functionalized silane, polypropylfumerate, collagen, glycosaminoglycan, polyamino acid, or a combination. The solid support can be porous. The target molecules in the different predefined regions can be at least 20% pure. The target molecules in the different predefined regions can be at least 50% pure. The target molecules in the different predefined regions can be at least 80% pure. The target molecules in the different predefined regions can be at least 90% pure. Following associating the target molecule with the solid support, the target molecule can be separated from other molecules. A sample can comprise the target molecule, wherein, following associating the target molecule with the solid support, the target molecule can be separated from other molecules in the sample.

In some forms of the disclosed methods, the target molecule can comprise a protein of interest. The protein of interest can be immobilized on a solid support. The protein of interest can be immobilized on a solid support prior to associating the composition with the target molecule. A plurality of other proteins can be immobilized on the solid support. One or more other compositions can be associated with one or more of the other proteins, wherein one or more other signals can be generated by performing rolling circle amplification of one or more of the other compositions, wherein the other compositions each can comprise a reporter binding agent, an amplification target circle, and DNA polymerase, wherein the reporter binding agent can comprise a specific binding molecule and a rolling circle replication primer, wherein the specific binding molecule can be specific for the target molecule, wherein the specific binding molecule need not be bound to the target molecule prior to association of the composition with the target molecule, wherein the composition does not comprise tandem sequence DNA prior to association of the composition with the target molecule.

In some forms of the disclosed methods, the protein of interest can comprise a cell surface marker. The cell surface marker can be on a cell. The cell can be immobilized on a solid support. The cell can be separated from other cells by fluorescent activated cell sorting, wherein rolling circle amplification can result in an amplification product comprising a fluorescent label, wherein the fluorescent activated cell sorting can be accomplished using the fluorescent label of the amplification product. The cell can be separated from other cells, counted, or both, by flow cytometry. Rolling circle amplification can result in an amplification product comprising a fluorescent label. A bead can comprise the fluorescent label, wherein the target molecule can be separated from other molecules by fluorescent activated cell sorting, wherein the fluorescent activated cell sorting can be accomplished using the fluorescent label of the bead. The target molecule can be separated from other molecules, counted, or both, by flow cytometry. A bead can comprise the fluorescent label. The association of the composition with the target molecule can be performed as part of or in conjunction with a cytometric bead assay, immuno-histochemistry, flow cytometry, immuno-fluorescence microscopy, in situ hybridization, fluorescence in situ hybridization, multiparametric fluorescence in situ hybridization, or a combination.

Disclosed are methods for detecting one or more analytes, the method comprising (a) bringing into contact one or more analyte samples and one or more compositions and incubating the analyte samples and the compositions under conditions that promote interaction of the specific binding molecules and analytes, wherein each composition comprises a reporter binding agent, an amplification target circle, and DNA polymerase; and (b) incubating the compositions under conditions that promote replication of the amplification target circles, wherein replication of the amplification target circles results in the formation of tandem sequence DNA, and wherein detection of tandem sequence DNA indicates the presence of the corresponding analytes. Wherein the reporter binding agent comprises a specific binding molecule and a rolling circle replication primer, wherein the specific binding molecule is specific for a target molecule, wherein the specific binding molecule is not bound to the target molecule prior to association of the composition with the target molecule, wherein the composition does not comprise tandem sequence DNA prior to association of the composition with the target molecule, wherein each target molecule either comprises an analyte or is associated with an analyte, and wherein each specific binding molecule interacts with an analyte directly or indirectly.

In some forms of the disclosed methods, the analyte samples can include one or more first analyte samples and one or more second analyte samples, wherein the compositions can include one or more first compositions and one or more second compositions, the method can further comprise, following step (a) and prior to step (b), mixing one or more of the first analyte samples and one or more of the second analyte samples, wherein for each first composition there can be a matching second composition, wherein the specific binding molecules of the first composition can interact with the same analyte as the specific binding molecules of the matching second composition, wherein the rolling circle replication primer of each different composition can be different, wherein each different rolling circle replication primer can prime replication of a different one of the amplification target circles, wherein each different amplification target circle can produce a different tandem sequence DNA, wherein the presence or absence of the same analyte in different analyte samples can be indicated by the presence or absence of corresponding tandem sequence DNA.

In some forms of the disclosed methods, the analytes can be immobilized on a solid support, wherein the tandem sequence DNA corresponding to one of the analytes and produced in association with a first composition can be in the same location on the solid support as tandem sequence DNA corresponding to the same analyte and produced in association with the matching second composition, wherein the presence or absence of the same analyte in different analyte samples can be indicated by the presence or absence of corresponding tandem sequence DNA.

In some forms of the disclosed methods, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise, a whole antibody or an antibody fragment. The amplification target circle can be associated with the rolling circle replication primer. The DNA polymerase can be associated with the amplification target circle and the rolling circle replication primer.

In some forms of the disclosed methods, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed methods, the composition can be stored at or below about 25° C. The composition can be stored at or below about 4° C. The composition can be stored at or below about −20° C. The composition can be stored at or below about −70° C. The composition can be stored at or below room temperature. The DNA polymerase can be φ29 DNA polymerase. The composition can further comprise glycerol. The composition can further comprise from about 20% glycerol to about 50% glycerol. The amplification target circle can comprise a single-stranded, circular DNA molecule comprising a primer complement portion, wherein the primer complement portion can be complementary to the rolling circle replication primer.

Disclosed are RCA reagents comprising a reporter binding agent, an amplification target circle, and DNA polymerase; wherein the reporter binding agent comprises a specific binding molecule and a rolling circle replication primer.

Also disclosed are RCA reagents comprising one or more reporter binding agents, one or more amplification target circles, and one or more DNA polymerases; wherein the reporter binding agents each comprise one or more specific binding molecules and one or more rolling circle replication primers.

Also disclosed are reagents comprising a reporter binding agent, an amplification target circle, and DNA polymerase; wherein the reporter binding agent comprises a specific binding molecule and a rolling circle replication primer, wherein the specific binding molecule is specific for a target molecule, wherein the specific binding molecule is not bound to the target molecule, and wherein the reagent does not comprise tandem sequence DNA.

Also disclosed are reagents comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, wherein the specific binding molecules are not bound to the target molecule, and wherein the reagent does not comprise tandem sequence DNA.

The disclosed reagents can have a variety of forms. For example, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer.

In some forms of the disclosed reagents, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed reagents, the reagent can be stored at or below about 25° C. The reagent can be stored at or below about 4° C. The reagent can be stored at or below about −20° C. The reagent can be stored at or below about −70° C. The reagent can be stored at or below room temperature. The DNA polymerase can be φ29 DNA polymerase. The reagent can further comprise glycerol. The reagent can further comprise from about 20% glycerol to about 50% glycerol. The amplification target circle can comprise a single-stranded, circular DNA molecule comprising a primer complement portion, wherein the primer complement portion can be complementary to the rolling circle replication primer.

Disclosed are mixtures comprising a reporter binding agent, an amplification target circle, and DNA polymerase; wherein the reporter binding agent comprises a specific binding molecule and a rolling circle replication primer, wherein the specific binding molecule is specific for a target molecule, wherein the specific binding molecule is not bound to the target molecule, and wherein the mixture does not comprise tandem sequence DNA.

Also disclosed are mixtures comprising one or more reporter binding agents, one or more amplification target circles, and one or more DNA polymerases; wherein the reporter binding agents each comprise one or more specific binding molecules and one or more rolling circle replication primers, wherein the specific binding molecules each are specific for a target molecule, wherein the specific binding molecules are not bound to the target molecule, and wherein the mixture does not comprise tandem sequence DNA.

The disclosed mixtures can have a variety of forms. For example, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer.

In some forms of the disclosed mixtures, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed mixtures, the mixture can be stored at or below about 25° C. The mixture can be stored at or below about 4° C. The mixture can be stored at or below about −20° C. The mixture can be stored at or below about −70° C. The mixture can be stored at or below room temperature. The DNA polymerase can be 100 29 DNA polymerase. The mixture can further comprise glycerol. The mixture can further comprise from about 20% glycerol to about 50% glycerol. The amplification target circle can comprise a single-stranded, circular DNA molecule comprising a primer complement portion, wherein the primer complement portion can be complementary to the rolling circle replication primer.

Disclosed are kits comprising a composition and a buffer for rolling circle amplification; wherein the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are kits comprising a composition and one or more nucleotide triphosphates; wherein the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are kits comprising a composition and one or more detection probes; wherein the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are kits comprising a composition and one or more DNA strand displacement primers; wherein the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

Also disclosed are kits comprising a composition and one or more target molecules; wherein the composition comprises a reporter binding agent, an amplification target circle, and DNA polymerase, wherein the reporter binding agent comprises a specific binding molecule and a rolling circle replication primer, wherein the specific binding molecule is specific for a target molecule, wherein the specific binding molecule is not bound to the target molecule, and wherein the composition does not comprise tandem sequence DNA.

In some forms of the disclosed kits, the kit can further comprise nucleotide triphosphates. The kit can further comprise a solid support, wherein the solid support can comprise one or more second specific binding molecules, wherein each second specific binding molecule can be specific for a molecule of interest. The kit can further comprise one or more third specific binding molecules, wherein each third specific binding molecule can be specific for one of the molecules of interest, wherein the third specific binding molecule can be the target molecule, wherein the third specific binding molecule can be an animal immunoglobulin, wherein the specific binding molecule of the reporter binding agent can comprise an antibody specific for immunoglobulins from the same type of animal of which the third specific binding molecule can be an immunoglobulin. The target molecule can be one of the molecules of interest. The kit can further comprise a solid support, wherein the solid support can comprise a second specific binding molecule, wherein the second specific binding molecule can be specific for a molecule of interest. The kit can further comprise a third specific binding molecule, wherein the third specific binding molecule can be specific for the molecule of interest, wherein the third specific binding molecule can comprise the target molecule, wherein the third specific binding molecule can be an animal immunoglobulin, wherein the specific binding molecule of the reporter binding agent can comprise an antibody specific for immunoglobulins from the same type of animal of which the third specific binding molecule is an immunoglobulin. The target molecule can comprise the molecule of interest.

The compositions in the disclosed kits can have a variety of forms. For example, the reporter binding agent, the amplification target circle, and the DNA polymerase can be associated with each other. The reporter binding agent, the amplification target circle, and the DNA polymerase can be associated via non-covalent interactions. The specific binding molecule can comprise an antibody. The antibody can comprise a whole antibody or an antibody fragment. The amplification target circle can be associated with the rolling circle replication primer. The DNA polymerase can be associated with the amplification target circle and the rolling circle replication primer.

In some forms of the disclosed kits, the reporter binding agent can comprise a plurality of rolling circle replication primers. The reporter binding agent need not comprise a plurality of specific binding molecules. The amplification target circles can be associated with a plurality of the rolling circle replication primers. The rolling circle replication primers can be the same. The rolling circle replication primers can be different. The amplification target circles can be associated with a plurality of the rolling circle replication primers, and the amplification target circles can be different. An amplification target circle can be associated with each of the rolling circle replication primers, and a different amplification target circle can be associated with each different rolling circle replication primer. The reporter binding agent can comprise three or more rolling circle replication primers. The reporter binding agent can comprise two or three rolling circle replication primers.

In some forms of the disclosed kits, the composition can be stored at or below about 25° C. The composition can be stored at or below about 4° C. The composition can be stored at or below about −20° C. The composition can be stored at or below about −70° C. The composition can be stored at or below room temperature. The DNA polymerase can be φ29 DNA polymerase. The composition can further comprise glycerol. The composition can further comprise from about 20% glycerol to about 50% glycerol. The amplification target circle can comprise a single-stranded, circular DNA molecule comprising a primer complement portion, wherein the primer complement portion can be complementary to the rolling circle replication primer.

EXAMPLE

A. Example: Rolling Circle Amplification of RCA Reagents

This example demonstrates the use of an embodiment of the disclosed reagent compositions in rolling circle amplification and analysis of the effect of storage of the reagents on amplification. The RCA reagents were made up of anti-biotin antibody conjugated to a rolling circle replication primer with an amplification target circle hybridized to the rolling circle replication primer and φ29 DNA polymerase bound to the primer and circle. The reagent was prepared by first annealing the amplification target circle to the rolling circle replication primer on the antibody conjugate and then binding the DNA polymerase to the amplification target circle/antibody conjugate. Annealing was performed in 50 mM TRIS-HCl, pH 7.8, 10 mM $(NH_4)_2SO_4$, 100 µg/ml bovine serum albumin and at a concentration of 100 nM antibody conjugate and 150 nM amplification target circle. Annealing was performed for 45 minutes at 37° C. The resulting amplification target circle/antibody conjugate is stable for several months at 4° C. or lower. The amplification target circle/antibody conjugate was then mixed with φ29 DNA polymerase (50 mM final concentration) in 50 mM TRIS-HCl, pH 7.8, 10 mM $(NH_4)_2SO_4$, 100 µg/ml bovine serum albumin and incubated for 20 minutes at 31° C. Note that the reagent composition is produced in the absence of $Mg^{2+}$. The resulting reagent can be stored at −80° C. in 50% glycerol.

In this example, the reagent was stored at different temperatures for different lengths of time. Specifically, the reagent was stored at room temperature, 4° C., −20° C., or −80° C. for 0 hours (that is, freshly-prepared reagent), 2 days, 3 days, or 5 days. None of the reagents contained glycerol except the reagent stored at −20° C., which had 50% glycerol. The reagents were then used in RCA reactions to determine their activity. For the reactions, the reagent to be tested was bound to biotinylated Luminex beads and then brought into contact with a reaction mix including dNTPs, buffer, and BrdUTP. The RCA reaction was carried out in 50 mM TRIS-HCl, pH 7.8, 10 mM $(NH_4)_2SO_4$, 10 mM MgCl2, 100 µM each of dCTP, dGTP, and dATP, 90 µM dTTP, 10 µM BdUTP, 100 µg/ml bovine serum albumin and incubated for 45 minutes at 31° C. The amount of DNA produced in the reactions was determined by binding anti-BrdU antibody conjugated with phycoerythrin (BrdU-PE) and measuring fluorescence. The results are shown in FIG. 1. The percent activity refers to the activity of the reagent being tested versus the results using fresh reagent. As can be seen, reagent stored at room temperature quickly lost 20% of its activity and declined to 40% activity after 3 days in storage. Reagent stored at both 4° C. and −20° C. retained 90% or greater activity for storage up to three days and declined to above 80% activity after five days of storage. Reagent stored at −80 ° C. exhibited an immediate decline to 70% activity but retained this activity over 5 days of storage. This drop was likely a result of freezing since the reagent had no glycerol. When the reagent is stored in 50% glycerol this initial drop in activity is eliminated and the reagent retains greater than 80% activity over at least 10 days at −80° C.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a primer" includes a plurality of such primers, reference to "the primer" is a reference to one or more primers and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are specifically incorporated by reference. Nothing herein is to be construed as an admission that the present invention is not entitled to antedate such disclosure by virtue of prior invention.

Those skilled in the art will recognize, or be able to ascertain using no more than routine experimentation, many equivalents to the specific embodiments of the method and compositions described herein. Such equivalents are intended to be encompassed by the following claims.

We claim:

1. A composition comprising a reporter binding agent, an amplification target circle, and DNA polymerase,
   wherein the reporter binding agent comprises a specific binding molecule and a rolling circle replication primer,
   wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, and wherein the composition is not in an assay or reaction.

2. The composition of claim 1 wherein the reporter binding agent, the amplification target circle, and the DNA polymerase are associated via non-covalent interactions.

3. The composition of claim 1 wherein the specific binding molecule comprises an antibody.

4. The composition of claim 3 wherein the antibody comprises a whole antibody or an antibody fragment.

5. The composition of claim 1 wherein the reporter binding agent comprises a plurality of rolling circle replication primers.

6. The composition of claim 5 wherein the reporter binding agent does not comprise a plurality of specific binding molecules.

7. The composition of claim 5 wherein the amplification target circles are associated with a plurality of the rolling circle replication primers.

8. The composition of claim 7 wherein the rolling circle replication primers are the same.

9. The composition of claim 5 wherein the rolling circle replication primers are the same.

10. The composition of claim 5 wherein the rolling circle replication primers are different.

11. The composition of claim 10 wherein the amplification target circles are associated with a plurality of the rolling circle replication primers, wherein the amplification target circles are different.

12. The composition of claim 10 wherein an amplification target circle is associated with each of the rolling circle replication primers, wherein a different amplification target circle is associated with each different rolling circle replication primer.

13. The composition of claim 5 wherein the reporter binding agent comprises three or more rolling circle replication primers.

14. The composition of claim 5 wherein the reporter binding agent comprises two or three rolling circle replication primers.

15. The composition of claim 1 wherein the composition is stored at or below about 25° C.

16. The composition of claim 15 wherein the composition is stored at or below about 4° C.

17. The composition of claim 16 wherein the composition is stored at or below about −20° C.

18. The composition of claim 17 wherein the composition is stored at or below about −70° C.

19. The composition of claim 1 wherein the composition is stored at or below room temperature.

20. The composition of claim 1 wherein the DNA polymerase is φ29 DNA polymerase.

21. The composition of claim 1 further comprising glycerol.

22. The composition of claim 1 further comprising from about 20% glycerol to about 50% glycerol.

23. The composition of claim 1 wherein the amplification target circle comprises a single-stranded, circular DNA molecule comprising a primer complement portion, wherein the primer complement portion is complementary to the rolling circle replication primer.

24. A kit comprising a composition and a buffer for rolling circle amplification,
   wherein the composition comprises a reporter binding agent, an amplification target circle, and DNA polymerase,
   wherein the reporter binding agent comprises a specific binding molecule and a rolling circle replication primer,
   wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase directly associated with each other and form a complex, wherein the composition is not in an assay or reaction.

25. The kit of claim 24 further comprising nucleotide triphosphates.

26. The kit of claim 24 further comprising a solid support, wherein the solid support comprises one or more second specific binding molecules, wherein each second specific binding molecule is specific for a molecule of interest.

27. The kit of claim 26 further comprising one or more third specific binding molecules, wherein each third specific binding molecule is specific for one of the molecules of interest, wherein the third specific binding molecule is the target molecule, wherein the third specific binding molecule is an animal immunoglobulin, wherein the specific binding molecule of the reporter binding agent comprises an antibody specific for immunoglobulins from the same type of animal of which the third specific binding molecule is an immunoglobulin.

28. The kit of claim 26 wherein the target molecule is one of the molecules of interest.

29. The kit of claim 24 further comprising a solid support, wherein the solid support comprises a second specific binding molecule, wherein the second specific binding molecule is specific for a molecule of interest.

30. The kit of claim 29 further comprising a third specific binding molecule, wherein the third specific binding molecule is specific for the molecule of interest, wherein the third specific binding molecule comprises the target molecule, wherein the third specific binding molecule is an animal immunoglobulin, wherein the specific binding molecule of the reporter binding agent comprises an antibody specific for immunoglobulins from the same type of animal of which the third specific binding molecule is an immunoglobulin.

31. The kit of claim 29 wherein the target molecule comprises the molecule of interest.

32. The composition of claim 1, wherein the composition is stored prior to use of the composition in an assay or reaction.

33. The composition of claim 32, wherein the composition is stored 1 day or longer prior to use of the composition in an assay or reaction.

34. The composition of claim 33, wherein the composition is stored 5 days or longer prior to use of the composition in an assay or reaction.

35. The composition of claim 34, wherein the composition is stored 10 days or longer prior to use of the composition in an assay or reaction.

36. The composition of claim 35, wherein the composition is stored 1 month or longer prior to use of the composition in an assay or reaction.

37. The composition of claim 1, wherein the composition is stored prior to use of the composition to bind a target molecule and before the amplification target circle is amplified to produce tandem sequence DNA.

38. The composition of claim 37, wherein the composition is stored 1 day or longer prior to use of the composition to bind a target molecule and before the amplification target circle is amplified to produce tandem sequence DNA.

39. The composition of claim 38, wherein the composition is stored 5 days or longer prior to use of the composition to bind a target molecule and before the amplification target circle is amplified to produce tandem sequence DNA.

40. The composition of claim 39, wherein the composition is stored 10 days or longer prior to use of the composition to bind a target molecule and before the amplification target circle is amplified to produce tandem sequence DNA.

41. The composition of claim 40, wherein the composition is stored 1 month or longer prior to use of the composition to bind a target molecule and before the amplification target circle is amplified to produce tandem sequence DNA.

42. The composition of claim 1, wherein the composition is stored prior to use of the composition in an amplification assay or amplification reaction.

43. The composition of claim 1, wherein the composition has not been brought into contact with an analyte sample.

44. The composition of claim 1, wherein the composition does not include any nucleotides needed for replication.

45. The composition of claim 1 further comprising from about 10% glycerol to about 60% glycerol.

46. The composition of claim 1 further comprising from about 10% glycerol to about 50% glycerol.

47. The kit of claim 24, wherein the composition is stored prior to use of the composition in an assay or reaction.

48. The kit of claim 47, wherein the composition is stored 1 day or longer prior to use of the composition in an assay or reaction.

49. The kit of claim 48, wherein the composition is stored 5 days or longer prior to use of the composition in an assay or reaction.

50. The kit of claim 49, wherein the composition is stored 10 days or longer prior to use of the composition in an assay or reaction.

51. The kit of claim 50, wherein the composition is stored 1 month or longer prior to use of the composition in an assay or reaction.

52. The kit of claim 24, wherein the composition is stored prior to use of the composition to bind a target molecule and before the amplification target circle is amplified to produce tandem sequence DNA.

53. The kit of claim 52, wherein the composition is stored 1 day or longer prior to use of the composition to bind a target molecule and before the amplification target circle is amplified to produce tandem sequence DNA.

54. The kit of claim 53, wherein the composition is stored 5 days or longer prior to use of the composition to bind a target molecule and before the amplification target circle is amplified to produce tandem sequence DNA.

55. The kit of claim 54, wherein the composition is stored 10 days or longer prior to use of the composition to bind a target molecule and before the amplification target circle is amplified to produce tandem sequence DNA.

56. The kit of claim 55, wherein the composition is stored 1 month or longer prior to use of the composition to bind a target molecule and before the amplification target circle is amplified to produce tandem sequence DNA.

57. The kit of claim 24, wherein the composition is stored prior to use of the composition in an amplification assay or amplification reaction.

58. The kit of claim 24, wherein the composition has not been brought into contact with an analyte sample.

59. The kit of claim 24, wherein the composition does not include any nucleotides needed for replication.

60. The kit of claim 24 further comprising from about 10% glycerol to about 60% glycerol.

61. The kit of claim 24 further comprising from about 10% glycerol to about 50% glycerol.

62. A composition comprising a reporter binding agent, an amplification target circle, and DNA polymerase,
wherein the reporter binding agent comprises a specific binding molecule and a rolling circle replication primer,
wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, wherein the composition is stored at or below about 25° C. for 1 day or longer prior to use of the composition in an assay or reaction.

63. A composition comprising a reporter binding agent, an amplification target circle, and DNA polymerase,
wherein the reporter binding agent comprises a specific binding molecule and a rolling circle replication primer,
wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, wherein the composition is stored at or below about 4° C. for 10 days or longer prior to use of the composition in an assay or reaction.

64. A composition comprising a reporter binding agent, an amplification target circle, and DNA polymerase,
wherein the reporter binding agent comprises a specific binding molecule and a rolling circle replication primer, wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, wherein the composition is stored at or below about −20° C. for 1 month or longer prior to use of the composition in an assay or reaction.

65. A kit comprising a composition and a buffer for rolling circle amplification,
  wherein the composition comprises a reporter binding agent, an amplification target circle, and DNA polymerase,
  wherein the reporter binding agent comprises a specific binding molecule and a rolling circle replication primer,
  wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each other and form a complex, wherein the composition is stored at or below about 25° C. for 1 day or longer prior to use of the composition in an assay or reaction.

66. A kit comprising a composition and a buffer for rolling circle amplification,
  wherein the composition comprises a reporter binding agent, an amplification target circle, and DNA polymerase,
  wherein the reporter binding agent comprises a specific binding molecule and a rolling circle replication primer,
  wherein the specific binding molecule is specific for a target molecule, wherein the specific binding molecule is not bound to the target molecule, wherein the composition does not comprise tandem sequence DNA, wherein the reporter binding agent, the amplification target circle, and the DNA polymerase are directly associated with each and form a complex, wherein the composition is stored at or below about 4° C. for 10 days or longer prior to use of the composition in an assay or reaction.

* * * * *